United States Patent
Johnston

(10) Patent No.: US 10,155,936 B2
(45) Date of Patent: Dec. 18, 2018

(54) PARKIN LIGASE ACTIVATION METHODS AND COMPOSITIONS

(71) Applicant: An2H Discovery Limited, Dublin (IE)

(72) Inventor: Jennifer Johnston, Mill Valley, CA (US)

(73) Assignee: AN2H DISCOVERY LIMITED, Dublin (IE)

( * ) Notice: Subject to any disclaimer, the term of this patent is extended or adjusted under 35 U.S.C. 154(b) by 0 days.

(21) Appl. No.: 14/961,285

(22) Filed: Dec. 7, 2015

(65) Prior Publication Data

US 2016/0160205 A1    Jun. 9, 2016

Related U.S. Application Data

(60) Provisional application No. 62/237,400, filed on Oct. 5, 2015, provisional application No. 62/222,008, filed on Sep. 22, 2015, provisional application No. 62/087,972, filed on Dec. 5, 2014.

(51) Int. Cl.
| | |
|---|---|
| *C12N 9/00* | (2006.01) |
| *A61K 31/4196* | (2006.01) |
| *A61K 31/519* | (2006.01) |
| *A61K 38/00* | (2006.01) |

(52) U.S. Cl.
CPC ............ *C12N 9/93* (2013.01); *A61K 31/4196* (2013.01); *A61K 31/519* (2013.01); *A61K 38/00* (2013.01); *C07K 2319/42* (2013.01); *C07K 2319/95* (2013.01); *C12Y 603/02019* (2013.01); *G01N 2800/28* (2013.01)

(58) Field of Classification Search
CPC .... C12N 9/93; A61K 31/4196; A61K 31/519; A61K 38/00; C07K 2319/42; C07K 2319/95; C12Y 603/02019; G01N 2800/28
See application file for complete search history.

(56) References Cited

U.S. PATENT DOCUMENTS

| | | | |
|---|---|---|---|
| 5,817,675 | A | 10/1998 | Whitefield |
| 8,592,584 | B2 | 11/2013 | Hergenrother et al. |
| 8,778,945 | B2 | 7/2014 | Hergenrother et al. |
| 8,916,705 | B2 | 12/2014 | Hergenrother |
| 9,102,661 | B2 | 8/2015 | Hergenrother et al. |
| 2010/0184765 | A1 | 7/2010 | Huang et al. |
| 2012/0149744 | A1 | 6/2012 | Welsh et al. |
| 2012/0295891 | A1 | 11/2012 | Van Brandt et al. |
| 2013/0137707 | A1 | 5/2013 | Cox et al. |
| 2014/0073609 | A1 | 3/2014 | Hergenrother et al. |
| 2014/0378536 | A1 | 12/2014 | Dawson et al. |
| 2015/0017264 | A1 | 1/2015 | Hergenrother et al. |
| 2015/0099759 | A1 | 4/2015 | Hergenrother et al. |
| 2015/0210659 | A1 | 7/2015 | Chen et al. |
| 2015/0210717 | A1 | 7/2015 | Gunes et al. |
| 2015/0231132 | A1 | 8/2015 | Hergenrother |

FOREIGN PATENT DOCUMENTS

| | | |
|---|---|---|
| KR | 20100015088 A | 2/2010 |
| WO | WO 2010/091382 A1 | 8/2010 |
| WO | WO 2013/124407 A1 | 8/2013 |
| WO | WO 2013/131089 A2 | 9/2013 |
| WO | WO 2014/022858 A1 | 2/2014 |
| WO | WO 2014/041125 A1 | 3/2014 |
| WO | WO 2016/012896 A1 | 1/2016 |
| WO | WO 2016/090371 A2 | 6/2016 |

OTHER PUBLICATIONS

Regnstrom et al (PLOS One, 2013, 8(7), e66879, 1-12).*
RN850242-99-8 (Year: 2005).*
Akif et al., "High-resolution crystal structures of *Drosophila melanogaster* angiotensin-converting enzyme in complex with novel inhibitors and antihypertensive drugs." Journal of Molecular Biology (2010); 400(3): 502-517.
Anwander et al., "Volatile Donor-Functionalized Alkoxy Derivatives of Lutetium and Their Structural Characterization." Inorg. Chem. (1997); 36(16): 3545-3552.
Boriack-Sjodin et al., "Structural analysis of inhibitor binding to human carbonic anhydrase II." Protein Science (1998); 7(12): 2483-2489.
Bottomley et al., "Structural and functional analysis of the human HDAC4 catalytic domain reveals a regulatory structural zinc-binding domain." Journal of Biological Chemistry (2008); 283(39): 26694-26704.
Bourguet et al., "Pharmacomodulation of Broad Spectrum Matrix Metalloproteinase Inhibitors Towards Regulation of Gelatinases." INTECH Open Access Publisher, 2012; 29 pages.
Brandstetter et al., "The 1.8-Å crystal structure of a matrix metalloproteinase 8-barbiturate inhibitor complex reveals a previously unobserved mechanism for collagenase substrate recognition." Journal of Biological Chemistry (2001); 276(20): 17405-17412.
Bressi et al., "Exploration of the HDAC2 foot pocket: Synthesis and SAR of substituted N-(2-aminophenyl) benzamides." Bioorganic & Medicinal Chemistry Letters (2010); 20(10): 3142-3145.
Briganti et al., "Carbonic anhydrase activators: X-ray crystallographic and spectroscopic investigations for the interaction of isozymes I and II with histamine." Biochemistry (1997); 36(34): 10384-10392.
Browner et al., "Matrilysin-inhibitor complexes: common themes among metalloproteases." Biochemistry (1995); 34(20): 6602-6610.
Cappalonga et al., "Structural comparison of sulfodiimine and sulfonamide inhibitors in their complexes with zinc enzymes." Journal of Biological Chemistry (1992); 267(27): 19192-19197.
Carta et al., "Dithiocarbamates strongly inhibit carbonic anhydrases and show antiglaucoma action in vivo." Journal of Medicinal Chemistry (2012); 55(4): 1721-1730.

(Continued)

*Primary Examiner* — Rachael E Bredefeld
*Assistant Examiner* — Ibrahim D Bori
(74) *Attorney, Agent, or Firm* — Cooley LLP

(57) ABSTRACT

The present invention is directed to methods and compositions for activating a Parkin ligase by administering to a subject in need thereof a therapeutically effective amount of a compound that disrupts at least one Parkin ligase zinc finger. The present invention is also directed to methods of treating and/or reducing the incidence of diseases or conditions related to the activation of Parkin ligase.

14 Claims, 6 Drawing Sheets

Specification includes a Sequence Listing.

(56) References Cited

OTHER PUBLICATIONS

Dunten et al., "X-ray structure of a novel matrix metalloproteinase inhibitor complexed to stromelysin." Protein Science (2001); 10(5): 923-926.
Fernández et al., "The X-Ray Structure of Carboxypeptidase A Inhibited by a Thiirane Mechanism-Based Inhibitor." Chemical Biology & Drug Design (2010); 75(1): 29-34.
Finzel et al., "Structural characterizations of nonpeptidic thiadiazole inhibitors of matrix metalloproteinases reveal the basis for stromelysin selectivity." Protein Science (1998); 7(10): 2118-2126.
Hadjuk et al., "NMR-based modification of matrix metalloproteinase inhibitors with improved bioavailability." Journal of Medicinal Chemistry (2002); 45(26): 5628-5639.
International Patent Application No. PCT/US2015/064305, Search Report and Written Opinion dated May 27, 2016.
Kim and Lipschomb, "Comparison of the structures of three carboxypeptidase A-phosphonate complexes determined by X-ray crystallography." Biochemistry (1991); 30(33): 8171-8180.
Kitada et al., "Mutations in the parkin gene cause autosomal recessive juvenile parkinsonism." Nature (1998); 392(6676): 605-608.
Lloyd et al., "Crystal structure of human carbonic anhydrase II at 1.95 Å resolution in complex with 667-coumate, a novel anti-cancer agent." Biochemical Journal (2005); 385(3): 715-720.
Matsumine et al., "A microdeletion of D6S305 in a family of autosomal recessive juvenile parkinsonism (PARK2)." Genomics (1998); 49(1): 143-146.
Monzingo and Matthews, "Binding of N-carboxymethyl dipeptide inhibitors to thermolysin determined by X-ray crystallography: a novel class of transition-state analogs for zinc peptidases." Biochemistry (1984); 23(24): 5724-5729.
Nogrady, Thomas, Medicinal Chemistry A Biochemical Approach, Medicinal Chemistry A Biochemical Approach, Oxford University Press, New York (1985); pp. 388-392, 9 pages.
Park et al., "Sulfamide-based inhibitors for carboxypeptidase A. Novel type transition state analogue inhibitors for zinc proteases." Journal of Medicinal Chemistry (2002); 45(24): 5295-5302.
Pavlovsky et al., "X-ray structure of human stromelysin catalytic domain complexed with nonpeptide inhibitors: implications for inhibitor selectivity." Protein Science (1999); 8(07): 1455-1462.
Popovic et al., "Ubiquitination in disease pathogenesis and treatment." Nature Medicine (2014); 20(11): 1242-1253.
Prachayasittikul et al., "8-Hydroxyquinolines: a review of their metal chelating properties and medicinal applications." Drug Design, Development and Therapy (2013); 7: 1157-1178.
Puerta and Cohen, "Examination of novel zinc-binding groups for use in matrix metalloproteinase inhibitors." Inorganic Chemistry (2003); 42(11): 3423-3430.
Puerta et al., "Heterocyclic zinc-binding groups for use in next-generation matrix metalloproteinase inhibitors: potency, toxicity, and reactivity." JBIC Journal of Biological Inorganic Chemistry (2006); 11(2): 131-138.
Rao, B.G., "Recent developments in the design of specific matrix metalloproteinase inhibitors aided by structural and computational studies." Current Pharmaceutical Design (2005); 11(3): 295-322.
Rice et al., "Evaluation of selected chemotypes in coupled cellular and molecular target-based screens identifies novel HIV-1 zinc finger inhibitors." Journal of Medicinal Chemistry (1996); 39(19): 3606-3616.
Schröder et al., "Structure-based design and synthesis of potent matrix metalloproteinase inhibitors derived from a 6 H-1, 3, 4-thiadiazine scaffold." Journal of Medicinal Chemistry (2001); 44(20): 3231-3243.
Scozzafava and Supuran, "Carbonic Anhydrase and Matrix Metalloproteinase Inhibitors: Sulfonated Amino Acid Hydroxamates with Mmp Inhibitory Properties Act as Efficient inhibitors of CA Isozymes I, II, and IV, and N-Hydroxysulfonamides Inhibit Both These Zinc Enzymes." Journal of Medicinal Chemistry (2000); 43(20): 3677-3687.
Shimura et al., "Familial Parkinson disease gene product, parkin, is a ubiquitin-protein ligase." Nature Genetics (2000); 25(3): 302-305.
Tronrud et al., "Crystallographic structural analysis of phosphoramidates as inhibitors and transition-state analogs of thermolysin." European Journal of Biochemistry (1986); 157(2): 261-268.
Veeriah et al., "Somatic mutations of the Parkinson's disease-associated gene PARK2 in glioblastoma and other human malignancies." Nature Genetics (2010); 42(1): 77-82.
Wang and Maldonado, "The ubiquitin-proteasome system and its role in inflammatory and autoimmune diseases." Cell Mol Immunol (2006); 3(4): 255-261.
Wang et al., "Characterization of alpha-nitromethyl ketone as a new zinc-binding group based on structural analysis of its complex with carboxypeptidase A." Bioorg Med Chem Lett. (2009); 19(17): 5009-5011.
Wang et al., "Design and synthesis of novel inhibitors of gelatinase B." Bioorganic & Medicinal Chemistry Letters (2002); 12(16): 2201-2204.
Wang et al., "ERK-mediated phosphorylation of TFAM downregulates mitochondrial transcription: Implications for Parkinson's disease." Mitochondrion (2014), 17: 132-140.
Wang et al., "Optical 2-benzyl-5-hydroxy-4-oxopentanoic acids against carboxypeptidase A: Synthesis, kinetic evaluation and X-ray crystallographic study." Chinese Chemical Letters (2010); 21: 159-162.
Wang et al., "Suppression of breast cancer by chemical modulation of vulnerable zinc fingers in estrogen receptor." Nature Medicine (2004); 10(1): 40-47.
Watermeyer et al., "Probing the Basis of Domain-Dependent Inhibition Using Novel Ketone Inhibitors of Angiotensin-Converting Enzyme." Biochemistry (2008); 47(22): 5942-5950.
Yu et al., "Clioquinol targets zinc to lysosomes in human cancer cells." Biochemical Journal (2009); 417(1): 133-139.
Chernyshev et al., "Acyl and sulfonyl derivatives of 3, 5-diamino-1-R-1, 2, 4-triazoles." Chemistry of Heterocyclic Compounds (2005); 41.9: 1139-1146.
Park et al., "Identification of novel inhibitors of extracellular signal-regulated kinase 2 based on the structure-based virtual screening." Bioorganic & Medicinal Chemistry Letters (2008); 18(20): 5372-5376.
PCT/US2015/064305, International Preliminary Report on Patentability dated Jun. 6, 2017, 7 pages.
Ikeuchi et al., "Attenuation of proteolysis-mediated cyclin E regulation by alternatively spliced Parkin in human colorectal cancers." Int. J. Cancer (2009); 125(9): 2029-2035.
PCT/US2017/035994, International Search Report and Written Opinion dated Oct. 20, 2017, 16 pages.
PCT/US2017/035933, International Search Report and Written Opinion dated Oct. 23, 2017, 15 pages.
Riley et al., "Structure and function of Parkin E3 ubiquitin ligase reveals aspects of RING and HECT ligases." Nat Commun. (2013); 4: 1982.

\* cited by examiner

PARKIN LIGASE ACTIVATION METHODS AND COMPOSITIONS

CROSS REFERENCE TO RELATED APPLICATIONS

This application claims the priority benefit of U.S. Provisional Application No. 62/237,400, filed Oct. 5, 2015, U.S. Provisional Application No. 62/222,008, filed Sep. 22, 2015, and U.S. Provisional Application No. 62/087,972, filed Dec. 5, 2014, the disclosures of which are incorporated by reference herein in their entirety.

FIELD OF THE INVENTION

The present invention relates to methods of activating Parkin ligase by disrupting zinc finger domains for therapeutic benefit.

BACKGROUND OF THE INVENTION

Ubiquitin-Proteasome Pathway System (UPS) is a critical pathway that regulates key regulator proteins and degrades misfolded or abnormal proteins. UPS is central to multiple cellular processes, and if defective or imbalanced, it leads to pathogenesis of a variety of diseases. Posttranslational modification of proteins by ubiquitin is a fundamental cellular mechanism that regulates protein stability and activity and underlies a multitude of functions, from almost every aspect of biology. The covalent attachment of ubiquitin to specific protein substrates is achieved through the action of E3 ubiquitin ligases. These ligases comprise over 500 different proteins and are categorized into multiple classes defined by the structural element of their E3 functional activity. Specifically, both HECT and RING ligases transfer an activated ubiquitin from a thioester to the e-amino acid group of a lysine residue on a substrate; however, HECT ligases have an active site cysteine that forms an intermediate thioester bond with ubiquitin, while RING ligases function as a scaffold to allow direct ubiquitin transfer from the E2 to substrate. Recent evidence suggests that a subfamily of RING ligases, the RING-between-RING (RBR) family, may contain a catalytic cysteine residue 1,2 in addition to a canonical RING domain. (Riley et al. 2013. *Nat Commun.* 4:1982, "Riley et al."), which is herein incorporated by reference in its entirety.

Deubiquitinating proteins and ubiquitin-specific proteases (DUBs and USPs) and E3 Ligases play a vital role in the UPS. These proteins are supported by flexible Zinc Finger (ZnF) domains which stabilize the binding of ubiquitin (Ub) for specialized functions.

Parkin is a RING-between-RING E3 ligase that functions in the covalent attachment of ubiquitin to specific substrates, and mutations in Parkin are linked to Parkinson's disease, cancer and mycobacterial infection. The individual RING domains for Parkin have been the subject of much debate, in regards to the specific residues that coordinate Zn ions, as well as their relationship to canonical RING crossbrace structures defining classical E2-binding domains. R0 is a novel domain structure, but is more similar to Zn-finger domains than to E3 RING domains (Riley et al. 2013. *Nat Commun.* 4:1982)

While many drug discovery programs focus on the UPS, few have been successful due to the lack of selectivity and direct access to enzymatic protein active sites. The present invention is directed towards a novel approach of disrupting Zn-finger domains that provide a therapeutic benefit for various diseases and disorders, including oncology and neurology disorders.

SUMMARY OF THE INVENTION

The present invention relates to modulating the structures and/or functions of ligases in the UPS by binding to zinc ions and/or cysteine residues in their ZnF domains, for therapeutic benefit. This mechanism is distinct from binding to the active sites of ligases, which receive the tail of Ub. The present invention is directed to a method for activating Parkin ligase by coordination of small molecules to zinc ions in Parkin ZnF domains, or by chemical reactions of small molecules with cysteine residues in Parkin ZnF domains. The coordination of small molecules to zinc ions may or may not remove the zinc ions from the ZnF domains. The chemical reactions of small molecules with cysteine residues may be reversible or irreversible.

Specific embodiments of the present invention include methods of activating a Parkin ligase. In a specific embodiment, the Parkin ligase may be activated by administering to a subject a therapeutically effective amount of a compound that disrupts at least one Parkin ligase zinc finger. In another specific embodiment, the compound can coordinate with a Zn ion, and/or bind or react with a cysteine. In a specific embodiment, the compound may react with the thiol group in the cysteine.

In another embodiment, the activated Parkin ligase suppresses one or more tumors. In another specific embodiment, the activated Parkin ligase provides dopamine neuron protection.

Compounds that can coordinate to a Zn ion include, but are not limited to, a monodentate, bidentate, or tridentate ligand. Compounds that can react with the thiol group in the cysteine residue include, but are not limited to an alkylator, oxidant, Michael acceptor, another unsaturated structure, or a disulfide.

In certain embodiments, the compound eliminates damaged mitochondria, increases cell viability during cellular stress, decreases tumor transformation and/or mitigates alpha-synuclein in cells. In certain embodiments, the subject has been diagnosed with cancer. In certain embodiments, cancer is glioblastoma, small cell lung carcinoma, breast cancer or prostate cancer.

In some embodiments, the patient has been diagnosed with a neuro-degenerative disease.

In particular embodiments, the neurodegenerative disease is Parkinson's disease, dementia, Amyotrophic lateral sclerosis (ALS) or Huntington's disease. In further embodiments, the dementia is dementia with Lewy bodies (DLB), multiple system atrophy (MSA) or Progressive supranuclear palsy (PSP).

In other embodiments of the present invention, the compound substantially disrupts the structure of at least one zinc finger in the Parkin ligase. In certain embodiments, at least one zinc finger is selected from one or more of the group consisting of the domains defined by R0 amino acids 141-216, IBR amino acids 328-377, and R2 amino acids 415-465. In a specific embodiment, the amino acid residues of at least one zinc finger corresponds to or aligns within one or more domains selected from the group consisting R0 amino acids 141-216, IBR amino acids 328-377, and R2 amino acids 415-465 of human Parkin Ligase. In further embodiments, the zinc finger comprises four cysteine residues. In a specific embodiment, the compound may be a zinc chelator.

In another specific embodiment, the compound can bind or react with one or more cysteine residues. In another specific embodiment, the compound can bind or react with one or more cysteine residues selected from the group consisting of C59 and C377 of human Parkin Ligase.

In one embodiment, the compound may substantially disrupt a structure of at least one zinc finger in the Parkin ligase. In another embodiment, the zinc finger in the Parkin ligase may be located within one or more domains selected from the group consisting of R0 amino acids 141-216, IBR amino acids 328-377, and R2 amino acids 415-465 of human Parkin Ligase. In another specific embodiment the zinc finger that is substantially disrupted is located in IBR amino acids 328-377 of the Parkin ligase.

In another embodiment, the compound may act synergistically with Phospho Ubiquitin (pUB) in activating the Parkin ligase.

In certain embodiments, Parkin ligase activation alters ubiquitination.

In another embodiment, activating the Parkin ligase treats or reduces the incidence of one or more diseases or ailments selected from the group consisting of Alzheimer's Dementia, Parkinson's disease, Huntington Disease, Amyotrophic Lateral Sclerosis (ALS), Freidreich's ataxia, Spinocerebellar Ataxia, Multiple Systems Atrophy, PSP, Tauopathy, Diffuse Lewy Body Disease, Lewy Body dementia, any disorder characterized by abnormal accumulation of α-synuclein, disorders of the aging process, stroke, bacterial infection, viral infection, Mitochondrial related disease, mental retardation, deafness, blindness, diabetes, obesity, cardiovascular disease, multiple sclerosis, Sjogrens syndrome, lupus, glaucoma, including pseudoexfoliation glaucoma, Leber's Hereditary Optic Neuropathy, and rheumatoid arthritis.

In a specific embodiment, the bacterial infection is Mycobacterium infection. In another specific embodiment, the viral infection is Hepatitis C infection. In another specific embodiment, the Mitochondrial related disease is selected from one or more of the group consisting of Alpers Disease, Barth Syndrome/LIC (Lethal Infantile Cardiomyopathy), Beta-oxidation Defects, Carnitine-Acyl-Carnitine Deficiency, Carnitine Deficiency, Creatine Deficiency Syndromes, Co-Enzyme Q10 Deficiency, Complex I Deficiency, Complex II Deficiency, Complex III Deficiency, Complex IV Deficiency/COX Deficiency, Complex V Deficiency, CPEO, CPT I Deficiency, CPT II Deficiency, KSS, Lactic Acidosis, LBSL—Leukodystrophy, LCAD, LCHAD, Leigh Disease or Syndrome, Luft Disease, MAD/Glutaric Aciduria Type II, MCAD, MELAS, MERRF, MIRAS, Mitochondrial Cytopathy, Mitochondrial DNA Depletion, Mitochondrial Encephalopathy, Mitochondrial Myopathy, MNGIE, NARP, Pearson Syndrome, Pyruvate Carboxylase Deficiency, Pyruvate Dehydrogenase Deficiency, POLG Mutations, Respiratory Chain related disease, SCAD, SCHAD, and VLCAD.

Another embodiment of the invention includes methods of treating and/or reducing the incidence of cancer. A specific embodiment includes administering to a subject in need thereof a therapeutically effective amount of a compound that disrupts at least one Parkin ligase zinc finger and induces Parkin ligase activity, wherein the compound can coordinate with a Zn ion and/or react with a thiol group in a cysteine. In another specific embodiment, activating the Parkin ligase suppresses one or more tumors. In another embodiment, the compound eliminates damaged mitochondria, increases cell viability during cellular stress, decreases tumor transformation and/or mitigates α-synuclein in cells. In another embodiment, the cancer is glioblastoma, small cell lung carcinoma, breast cancer or prostate cancer.

Another embodiment of the present invention includes methods for treating and/or reducing the incidence of Parkinson's disease. A specific embodiment for treating and/or reducing the incidence of Parkinson's disease includes administering to a subject in need thereof a therapeutically effective amount of a compound that disrupts at least one Parkin ligase zinc finger and induces Parkin ligase activity, wherein the compound can coordinate with a Zn ion and/or react with a thiol group in a cysteine.

In some embodiments, Parkin ligase activation alters ubiquitination, as defined by the ability of Parkin to modify a substrate protein by covalent attachment of ubiquitin, a substrate protein being Parkin itself, or another protein such as Mitofusion 1 or 2, FBW7, or other publicly reported substrates of Parkin ligase.

Another embodiment of the present invention includes pharmaceutical formulations. In a specific embodiment, the pharmaceutical formulations activate Parkin ligase. In another specific embodiment, the pharmaceutical formulations may comprise an effective amount of a compound or its salt thereof that disrupts at least one Parkin ligase zinc finger, and a pharmaceutically acceptable carrier, wherein the compound or its salt thereof can coordinate a Zn ion, and/or react with the thiol group in a cysteine. In another specific embodiment, the compound can bind or react with one or more cysteine residues selected from the group consisting of C59 and C377 of human Parkin Ligase. In a specific embodiment, the pharmaceutical composition is in a formulation selected from the group consisting of a solid, powder, liquid and a gel.

DETAILED DESCRIPTION

Figure 1:
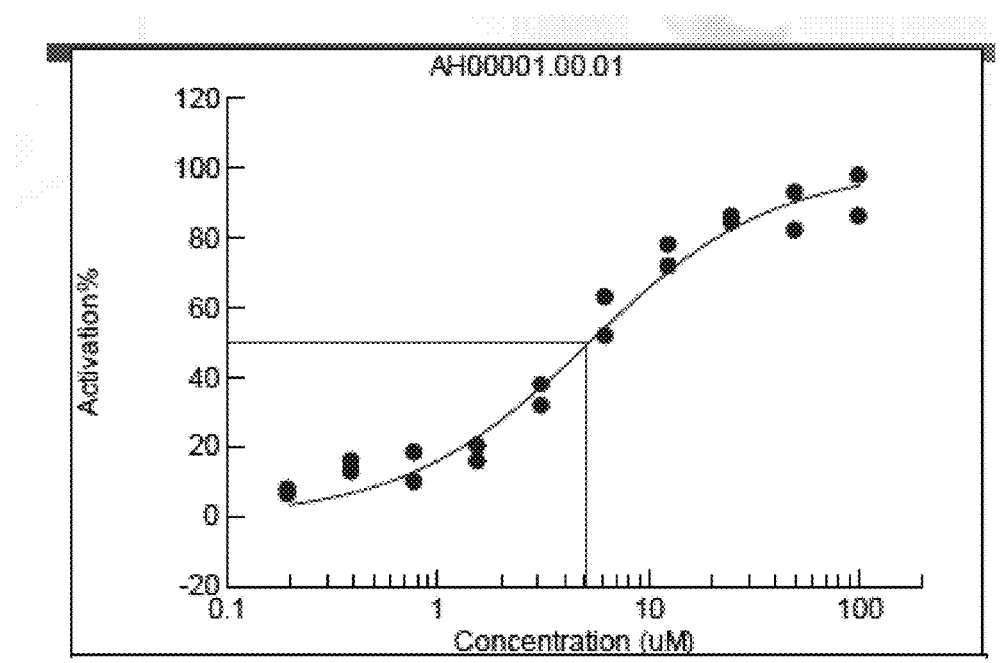
FIG. 1 indicates that N,N'-(1-phenyl-1H-1,2,4-triazole-3,5-diyl)dibenzamide, a chelator compound (identified as AH001 or compound 76 in Table 2) increases the Parkin Ligase reaction with the Activity-based Ubiquitin vinyl sulfone probe.

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Definitions

Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

The term "treating" means one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

An "effective amount" means the amount of a formulation according to the invention that, when administered to a patient for treating a state, disorder or condition is sufficient to effect such treatment. The "effective amount" will vary depending on the active ingredient, the state, disorder, or condition to be treated and its severity, and the age, weight, physical condition and responsiveness of the mammal to be treated.

The term "therapeutically effective" applied to dose or amount refers to that quantity of a compound or pharmaceutical formulation that is sufficient to result in a desired clinical benefit after administration to a patient in need thereof.

All weight percentages (i.e., "% by weight" and "wt. %" and w/w) referenced herein, unless otherwise indicated, are measured relative to the total weight of the pharmaceutical composition.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof As used herein, the "alignment" of two or more protein/amino acid sequences may be performed using the alignment program ClustalW2, available at the ebi website. The following default parameters may be used for Pairwise alignment: Protein Weight Matrix=Gonnet; Gap Open=10; Gap Extension=0.1.

"Ubiquitin Proteasome Pathway System (UPS)" as used herein relates to the ubiquitin proteasome pathway, conserved from yeast to mammals, and is required for the targeted degradation of most short-lived proteins in the eukaryotic cell. Targets include cell cycle regulatory proteins, whose timely destruction is vital for controlled cell division, as well as proteins unable to fold properly within the endoplasmic reticulum. Ubiquitin modification is an ATP-dependent process carried out by three classes of enzymes. A "ubiquitin activating enzyme" (E1) forms a thio-ester bond with ubiquitin, a highly conserved 76-amino acid protein. This reaction allows subsequent binding of ubiquitin to a "ubiquitin conjugating enzyme" (E2), followed by the formation of an isopeptide bond between the carboxy-terminus of ubiquitin and a lysine residue on the substrate protein. The latter reaction requires a "ubiquitin ligase" (E3). E3 ligases can be single- or multi-subunit enzymes. In some cases, the ubiquitin-binding and substrate binding domains reside on separate polypeptides brought together by adaptor proteins or culling. Numerous E3 ligases provide specificity in that each can modify only a subset of substrate proteins. Further specificity is achieved by post-translational modification of substrate proteins, including, but not limited to, phosphorylation. Effects of monoubiquitination include changes in subcellular localization. However, multiple ubiquitination cycles resulting in a polyubiquitin chain are required for targeting a protein to the proteasome for degradation. The multisubunit 26S proteasome recognizes, unfolds, and degrades polyubiquitinated substrates into small peptides. The reaction occurs within the cylindrical core of the proteasome complex, and peptide bond hydrolysis employs a core threonine residue as the catalytic nucleophile. It has been shown that an additional layer of complexity, in the form of multiubiquitin chain receptors, may lie between the polyubiquitination and degradation steps. These receptors react with a subset of polyubiquitinated substrates, aiding in their recognition by the 26S proteasome, and thereby promoting their degradation. This pathway is not only important in cellular homeostasis, but also in human disease. Because ubiquitin/proteasome-dependent degradation is often employed in control of the cell division cycle and cell growth, researchers have found that proteasome inhibitors hold some promise of being developed into potential cancer therapeutic agents.

Protein degradation through the ubiquitin-proteasome system is the major pathway of non-lysosomal proteolysis of intracellular proteins. It plays important roles in a variety of fundamental cellular processes such as regulation of cell cycle progression, division, development and differentiation, apoptosis, cell trafficking, and modulation of the immune and inflammatory responses. The central element of this system is the covalent linkage of ubiquitin to targeted proteins, which are then recognized by the 26S proteasome, an adenosine triphosphate-dependent, multi-catalytic protease. Damaged, oxidized, or misfolded proteins as well as regulatory proteins that control many critical cellular functions are among the targets of this degradation process. Aberration of this system leads to the dysregulation of cellular homeostasis and the development of multiple diseases (Wang et al. *Cell Mol Immunol.* 2006 August; 3(4): 255-61).

"Parkin Ligase" or "Parkin" as used herein relates to a protein which in humans is encoded by the PARK2 gene. (Kitada T, Asakawa S, Hattori N, Matsumine H, Yamamura Y, Minoshima S, Yokochi M, Mizuno Y, Shimizu N (April 1998). "Mutations in the parkin gene cause autosomal recessive juvenile parkinsonism". *Nature* 392 (6676): 605-608. doi:10.1038/33416. PMID 9560156. Matsumine H, Yamamura Y, Hattori N, Kobayashi T, Kitada T, Yoritaka A, Mizuno Y (April 1998). "A microdeletion of D6S305 in a family of autosomal recessive juvenile parkinsonism (PARK2)". *Genomics* 49 (1): 143-146. doi:10.1006/geno.1997.5196. PMID 9570960. The protein is a component of a multiprotein E3 ubiquitin ligase complex which in turn is part of the ubiquitin-proteasome system that mediates the targeting of proteins for degradation. Mutations in the PARK2 gene are known to cause a familial form of Parkinson's disease known as autosomal recessive juvenile Parkinson's disease (AR-JP).

"Ligase" as used herein, is an enzyme that can catalyze the joining of two or more compounds or biomolecules by bonding them together with a new chemical bond. The "ligation" of the two usually with accompanying hydrolysis of a small chemical group dependent to one of the larger compounds or biomolecules, or the enzyme catalyzing the linking together of two compounds, e.g., enzymes that catalyze joining of groups C—O, C—S, C—N, etc. Ubiquitin-protein (E3) ligases are a large family of highly diverse enzymes selecting proteins for ubiquitination.

"Ub Ligases" are involved in disease pathogenesis for oncology, inflammation & infectious disease. E3 ligase belonging to the RING-between-RING (RBR) family of E3 ligases containing both canonical RING domains and a catalytic cysteine residue usually restricted to HECT E3 ligases; termed 'RING/HECT hybrid' enzymes. Mutations in Parkin linked to Parkinson's disease, cancer and mycobacterial infection. Parkin is recognized as a neuroprotective protein with a role in mitochondrial integrity. Human genetic data implicate loss of Parkin activity as a mechanism for pathogenesis of Parkinson's Disease (PD).

"Zinc Finger (ZnF) Domain" as used herein relates to a protein structure characterized by coordinating zinc ions to stabilize the functional activity. ZnF stabilize the binding of Ub, Deubiquitinating Enzymes (DUBs), and Ligases (E3) in the UPS.

"Ligands" as used herein bind to metal via one or more atoms in the ligand, and are often termed as chelating ligands. A ligand that binds through two sites is classified as bidentate, and three sites as tridentate. The "bite angle" refers to the angle between the two bonds of a bidentate chelate. Chelating ligands are commonly formed by linking donor groups via organic linkers. A classic bidentate ligand is ethylenediamine, which is derived by the linking of two ammonia groups with an ethylene (—CH2CH2-) linker. A classic example of a polydentate ligand is the hexadentate chelating agent EDTA, which is able to bond through six sites, completely surrounding some metals. The binding affinity of a chelating system depends on the chelating angle or bite angle. Many ligands are capable of binding metal ions through multiple sites, usually because the ligands have lone pairs on more than one atom. Some ligands can bond to a metal center through the same atom but with a different number of lone pairs. The bond order of the metal ligand bond can be in part distinguished through the metal ligand bond angle (M-X—R). This bond angle is often referred to as being linear or bent with further discussion concerning the degree to which the angle is bent. For example, an imido ligand in the ionic form has three lone pairs. One lone pair is used as a sigma X donor, the other two lone pairs are available as L type pi donors. If both lone pairs are used in pi bonds then the M-N—R geometry is linear. However, if one or both these lone pairs is non-bonding then the M-N—R bond is bent and the extent of the bend speaks to how much pi bonding there may be. It was found that few heteroatoms, such as nitrogen, oxygen, and sulfur atoms, interacted with zinc, ideal distances between the zinc and these heteroatoms were identified. Whereas carboxylates bound to the zinc via both monodentate and bidentate interactions, the hydroxamates bound dominantly in a bidentate manner. These results aid in the design of new inhibitors with the potential to interact with zinc in the target protein. Virtually every molecule and every ion can serve as a ligand for (or "coordinate to") metals. Monodentate ligands include virtually all anions and all simple Lewis bases. Thus, the halides and pseudohalides are important anionic ligands whereas ammonia, carbon monoxide, and water are particularly common charge-neutral ligands. Simple organic species are also very common, be they anionic ($RO^-$ and $RCO_2^-$) or neutral ($R_2O$, $R_2S$, $R_{3-x}NH_x$, and $R_3P$). Complexes of polydentate ligands are called chelate complexes. They tend to be more stable than complexes derived from monodentate ligands. This enhanced stability, the chelate effect, is usually attributed to effects of entropy, which favors the displacement of many ligands by one polydentate ligand. When the chelating ligand forms a large ring that at least partially surrounds the central atom and bonds to it, leaving the central atom at the center of a large ring. The more rigid and the higher its denticity, the more inert will be the macrocyclic complex.

"Chelator" as used herein relates to a binding agent that suppresses chemical activity by forming a chelate (a coordination compound in which a metal atom or ion is bound to a ligand at two or more points on the ligand, so as to form, for example, a heterocyclic ring containing a metal atom).

"Chelation" as used herein relates to a particular way that ions and molecules bind metal ions. According to the International Union of Pure and Applied Chemistry (IUPAC), chelation involves the formation or presence of two or more separate coordinate bonds between a polydentate (multiple bonded) ligand and a single central atom. Usually these ligands are organic compounds, and are called chelants, chelators, chelating agents, or sequestering agents.

"Electrophile" as used herein relates to species that is attracted to an electron rich center. In chemistry, an electrophile is a reagent attracted to electrons. It participates in a chemical reaction by accepting an electron pair in order to bond to a nucleophile. Because electrophiles accept electrons, they are Lewis acids. Most electrophiles are positively charged, have an atom that carries a partial positive charge, or have an atom that does not have an octet of electrons.

The following description includes information that may be useful in understanding the present invention. It is not an admission that any of the information provided herein is prior art or relevant to the presently claimed inventions, or that any publication specifically or implicitly referenced is prior art.

Ubiquitin-protein (E3) ligases are a large family of enzymes that select various proteins for ubiquitination. These ubiquitin ligases, called "Ub ligases" are known to have a role in various diseases and conditions, including but not limited to, cancer, inflammation and infectious diseases.

One specific Ub ligase is Parkin ligase. Parkin ligase is a component of a multiprotein "E3" ubiquitin ligase complex, which in turn is part of the ubiquitin-proteasome system that mediates the targeting of proteins for degradation. Although the specific function of Parkin ligase is not known, mutations in Parkin ligase are linked to various diseases, such as Parkinson's disease, cancer and mycobacterial infection. Parkin ligase is thus an attractive target for therapeutic intervention.

Further, there are various known methods for regulating ligases known in the art. Many ligases, particularly ligases involved in the Ubiquitin-Proteasome Pathway System (UPS), are known to have Zinc Finger (ZnF) domains that stabilize critical protein binding regions in that ligase.

ZnF domains coordinate zinc ions and this coordination stabilizes functional activity of the protein. The functional activity provided by proteins with ZnF domains can include the regulation of important cellular signaling pathways, such as recognizing ubiquitins, regulation of DNA, such as transcription and repair, and acting as cellular redox sensors. The binding of zinc to ZnF domains, or simply just regulating how zinc interacts with the ZnF domains, are essential to ligases involved in the UPS.

Parkin ligase is known to have one or more ZnF domains. The present invention focuses on two different strategies for modulating ZnF domains in Parkin ligase. One strategy of the present invention includes using chelating compounds that bind to the ZnF domains and thus disallow the binding of zinc, or cause the dissociation of zinc, such as Zn, or $Zn^{2+}$, from the ZnF domain.

Another strategy of the present invention includes using compounds that bind or react with a cysteine amino acid residue in the ZnF domain. One or more cysteine residues (and sometimes with the assistance of histidine residues) are essential in ZnF domains for binding to and/or coordinating to the zinc ion. The zinc ion (usually $Zn^{2+}$) can coordinate with multiple cysteine or histidine residues. The more cysteine residues there are in the domain, the more flexible is the ZnF domain. Ligases, such as Parkin ligase are thought to have multiple cysteine residues coordinated with zinc in their ZnF domains. This flexibility in the ZnF domains of Parkin ligase is thought allow the domain to be reversible, and is thus is one possible mechanism for regulating Parkin ligase.

The present invention thus relates to the use of one or more agents or one or more compounds with electrophilic, chelation or both electrophilic and chelation properties that can interact with the zinc ion and/or the cysteine residue(s) in a Parkin ligase and thus modulate Parkin ligase's activity. Specifically, it is believed that not allowing a zinc ion to coordinate in at least one of Parkin ligase's ZnF domains induces its activity. The present invention is thus directed to a method for activating Parkin ligase by the chelation of Zn followed by its removal from the ZnF domain, or through electrophilic attack at the cysteine amino acid(s) that holds the Zn in place.

Accordingly, in one embodiment of the present invention, the methods of activating a Parkin ligase include administering to a subject in need thereof a therapeutically effective amount of one or more compounds that disrupt at least one Parkin ligase zinc finger. In another embodiment, the methods of activating a Parkin ligase include administering to a subject two or more compounds that disrupt at least one Parkin ligase zinc finger.

In a specific embodiment, the compounds of the present invention may be an electrophile or a chelator. In another embodiment, the compounds of the present invention may be able to function as both an electrophile and as a chelator. For example, the compounds of the present invention can include multiple functional groups wherein a functional group has chelating properties and a functional group that has electrophilic properties.

In another specific embodiment, the compound is selected from one or more of the group consisting of the compounds in Table 1 and Table 2 or a salt or ester thereof. Although not bound to a specific theory, it is believed that at least some of the compounds in Table 1 or Table 2 may be chelators, electrophiles or both. For example, it is believed that compounds 76 and 97 from Table 2 act as a chelator, but compound 113 of Table 2 acts as a thiol-reactive electrophile. In another example, compounds from Table 1 or Table 2 can act as both an electrophile and as a nucleophile. It is believed, for example, that compounds 91 and 107 of Table 2 are both chelators, but can possibly also act as thiol-reactive electrophiles. Accordingly, in another specific embodiment, the compounds of the present invention are an electrophile, chelator or both an electrophile and a chelator selected from one or more of the group consisting of the compounds in Table 1 and Table 2 or a salt or ester thereof.

In another embodiment, the compounds in Table 1 and Table 2 or a salt or ester thereof bind and active Parkin ligase. For example, compounds N,N'-(1-phenyl-1H-1,2,4-triazole-3,5-diyl)dibenzamide (AH001), a chelator compound and 6-benzyl-2,5-dimethyl-3-phenylpyrazolo[1,5-a]pyrimidine-7-thiol (AH007), an electrophile and chelator compound, both independently increase the Parkin Ligase reaction with the Activity-based Ubiquitin vinyl sulfone probe. See Examples 2-3. Therefore, both chelators and/or electrophiles can bind and activate Parkin ligase.

In another embodiment, the compound can be 2-(4-benzylpiperazin-1-yl)-N-[(2-hydroxy-3-prop-2-enyl-phenyl)methylideneamino]acetamide (also referred to as Pac-1) or a salt or ester thereof. Although not bound to a specific theory, the structure of Pac-1, provided as compound 114 in Table 2 below, is believed to be a chelator and may also have the ability to increase the Parkin Ligase reaction. In another embodiment, Pac-1, or a salt or thereof, may also be an electrophile and/or be both a chelator and an electrophile.

In another embodiment, the compound may be a derivative or analogue of Pac-1. In a specific embodiment, the compound may be a compound as described in PCT Application Publication Nos. WO2010/091382, WO2013/131089, WO2013/124407, WO2014/022858, U.S. Application Publication Nos. US2015/0210659, US2015/0231132, US2014/0073609, US20150017264, US2015/0099759, U.S. Pat. No. 8,916,705, U.S. Pat. No. 9,102,661, U.S. Pat. No. 8,592,584, and U.S. Pat. No. 8,778,945, the disclosures of which are incorporated by reference herein in their entirety.

In a specific example, Activity-based probe assays and mass spectrometry analysis indicate that some candidate compounds in Table 1 and/or Table 2 can bind or react with multiple cysteine residues in human Parkin ligase. For example, mass spectrometry analysis shows that AH007 binds to at least cysteine residue 59 (C59) and cysteine residue 377 (C377) of Parkin ligase.

Accordingly, in a specific embodiment, methods of activating a Parkin ligase include administering to a subject in need thereof a therapeutically effective amount of one or more compounds that disrupt at least one Parkin ligase zinc finger. In a specific embodiment, the one or more compounds are selected from Table 1 and/or Table 2, or a salt or ester thereof. In another embodiment the compound may be a chelator, an electrophile or both a chelator and an electrophile.

In another embodiment, the one or more compounds can coordinate with a Zn ion, and/or bind or react with one or more cysteine residues. In a specific embodiment the Zn ion may be either a $Zn^+$ or a $Zn^{2+}$ ion. In another embodiment, the compound can coordinate to a Zn ion is a monodentate, bidentate, or tridentate ligand.

In another embodiment, the compound can bind and/or react with a thiol group in more than one cysteine residues. In another embodiment, the compound can bind and/or react with a thiol group in two cysteine residues. In another embodiment, the compound can bind and/or react with a thiol group in three cysteine residues. In another embodiment, the compound can bind and/or react with a thiol group in four cysteine residues. In another specific embodiment, the compound can bind or react with one or more cysteine residues in one or more domains selected from the group consisting amino acids 141-225, amino acids 238-293, amino acids 313-377, and amino acids 418-449 of human Parkin Ligase. See O60260 at the uniport website.

In another specific embodiment, the compound can bind or react with one or more cysteine residues selected from the group consisting of C182, C258 and C377 of human Parkin Ligase. In another specific embodiment, the compound can bind or react with one or more cysteine residues selected from the group consisting of C59 and C377 of human Parkin Ligase. In a specific embodiment, the compound can react with C377 of human Parkin Ligase. In another specific embodiment, the compound is AH007.

In another embodiment, the compound can bind or react with one or more cysteine residues selected from one or more residues of a parkin ligase, parkin ligase derivative, or parkin ligase homologue that correspond to or align with C182, C258 and/or C377 of human Parkin Ligase. In another embodiment, the compound can bind or react with one or more cysteine residues selected from one or more residues of a parkin ligase, parkin ligase derivative, or parkin ligase homologue that correspond to or align with C59 and/or C377 of human Parkin Ligase. In another specific embodiment, the compound is AH007.

It is also believed that the IBR domain may play a key role in regulating Parkin activity. It is believed that the R0 domain includes at least one ZnF domain that as discussed above, could be involved in one possible mechanism for regulating Parkin ligase. Accordingly, in a specific embodiment, the structure of at least one ZnF domain located in the IBR domain (amino acids 328-377) may be substantially disrupted by the administration of a compound to a subject in need thereof. In another embodiment, one or more compounds selected from Table 1 and/or Table 2, or a salt or ester thereof, may substantially disrupt the structure of at least one ZnF domain located in the IBR domain (amino acids 328-377).

In another embodiment, the compound can bind and/or react with a cysteine residue, including any histidine residue(s) in or near the ZnF domain.

In another embodiment, the compounds may substantially disrupt the structure of at least one zinc finger (or ZnF domain) in the Parkin ligase. In another embodiment, the compounds of the present invention may disrupt one or more ZnF domains in Parkin ligase.

Riley et al. describes a human Parkin ligase of 465 amino acids that includes multiple functional areas with Zn coordination residues (amino acid sequence provided in Table 3 (SEQ ID NO:1) and identified in the ncbi website (See sequence NM_004562.2). Riley et al. discusses 4 domains designated as R0, R1, IBR and R2. R0, R1 and R2 which were previously designated as RING domains. Riley et al., however questions whether the R0, IBR and R2 domains are actual, or traditional RING domains: "R0 is a novel domain structure, but is more similar to Zn-finger domains than to E3 RING domains" Riley et al. also states that neither IBR or the R2 domains resemble the canonical RING domain motif, as they do not have a cross-brace structure as normally associated with RING domains. Furthermore, analysis of the R0, IBR and R2 domains indicates possible vulnerabilities in their zinc centers. Thus, the R0, IBR and R2 domains look like ideal domain candidates for regulating the activity of Parkin Ligase. The R0, IBR and R2 domains refer to amino acids 141-216, amino acids 328-377, and amino acids 415-465 of human Parkin Ligase, respectively.

Accordingly, in a specific embodiment, the at least one zinc finger that may be substantially disrupted correspond to or align with one or more domains selected from the group consisting amino acids 141-216, amino acids 328-377, and amino acids 415-465 of human Parkin Ligase. In another specific embodiment, the amino acids from the at least one zinc finger may overlap in an alignment with one or more of the R0, IBR and R2 domains from human Parkin Ligase.

In another specific embodiment, the at least one zinc finger that may be substantially disrupted correspond to or align with one or more domains selected from the group consisting amino acids 141-225, amino acids 238-293, amino acids 313-377, and amino acids 418-449 of human Parkin Ligase. See O60260 at the uniport website.

In a specific embodiment, at least one of the zinc fingers in the Parkin ligase comprises, one, two, three or four cysteine residues. In another embodiment, the disruption of at least one zinc finger induces the activity of the Parkin ligase. In another embodiment, at least one of the zinc fingers in the Parkin ligase comprises, one, two, three or four cysteine residues from amino acids 141-225, amino acids 238-293, amino acids 313-377, and amino acids 418-449 of human Parkin Ligase. For example, in a specific embodiment, a compound can react and thus disrupt one or more zinc fingers by binding or reacting to one or more cysteine residues selected from the group consisting of C182, C258 and C377 of human Parkin Ligase.

The methods of the present invention also include activating auto-ubiquitinization of a Parkin ligase by administering to a subject in need thereof a therapeutically effective amount of one or more compounds. In a specific embodiment, the one or more compounds disrupt at least one Parkin ligase zinc finger. In another example, the compounds in Table 1 and/or Table 2 may be used to activate auto-ubiquitinization of Parkin ligase. In another embodiment, the compounds in Table 1 and/or Table 2 may be used in addition with other compounds to activate auto-ubiquitinization of Parkin ligase. For example, Phospho Ubiquitin (pUB), an endogenous cellular regulator of Parkin, can be added to Parkin ligase which can activate Parkin ligase and its auto-ubiquitinization. In one embodiment, one or more compounds in Table 1 and/or Table 2, or salts and esters therof, may be administered to a subject in need thereof that acts synergistically with Phospho Ubiquitin (pUB) in activating the Parkin ligase. See, e.g., Example 5. In another embodiment, one or more compounds may be administered with pUB to synergistically increase the activation of Parkin ligase and/or its auto-ubiquitinization. In another embodiment the compound may be a chelator and/or an electrophile. In a specific embodiment, the one or more compounds are selected from Table 1 and/or Table 2, or a salt or ester thereof.

In another specific embodiment, the activation of the Parkin ligase treats or reduces the incidence of one or more diseases or ailments selected from the group consisting of Alzheimer's Dementia, Parkinson's disease, Huntington Disease, Amyotrophic Lateral Sclerosis (ALS), Freidreich's ataxia, Spinocerebellar Ataxia, Multiple Systems Atrophy, PSP, Tauopathy, Diffuse Lewy Body Disease, Lewy Body dementia, any disorder characterized by abnormal accumulation of α-synuclein, disorders of the aging process, stroke, bacterial infection, viral infection, Mitochondrial related disease, mental retardation, deafness, blindness, diabetes, obesity, cardiovascular disease, multiple sclerosis, Sjogrens syndrome, lupus, glaucoma, including pseudoexfoliation glaucoma, Leber's Hereditary Optic Neuropathy, and rheumatoid arthritis.

In a specific embodiment, the bacterial infection is Mycobacterium infection. In another specific embodiment the viral infection is HIV, Hepatitis B infection or Hepatitis C infection. Another embodiment of the present invention includes methods of treating and/or reducing the incidence of cancer, specifically comprising administering to a subject in need thereof a therapeutically effective amount of one or more compounds that disrupt at least one Parkin ligase zinc finger and induces Parkin ligase activity. In a specific embodiment, the activated Parkin ligase suppresses the growth of one or more tumors and/or prevents metastasis of one or more tumors.

In another embodiment the cancer may be selected from one or more of the group consisting of Acute Lymphoblastic Leukemia, Acute Myeloid Leukemia, Adrenocortical Carcinoma, AIDS-Related Cancers, Kaposi Sarcoma, Lymphoma, Anal Cancer, Appendix Cancer, Astrocytomas, Childhood Atypical Teratoid/Rhabdoid Tumor, Basal Cell Carcinoma, Skin Cancer (Nonmelanoma), Childhood Bile Duct Cancer, Extrahepatic Bladder Cancer, Bone Cancer, Ewing Sarcoma Family of Tumors, Osteosarcoma and Malignant Fibrous Histiocytoma, Brain Stem Glioma, Brain Tumors, Embryonal Tumors, Germ Cell Tumors, Craniopharyngioma, Ependymoma, Bronchial Tumors, Burkitt Lymphoma (Non-Hodgkin Lymphoma), Carcinoid Tumor, Gastrointestinal Carcinoma of Unknown Primary, Cardiac (Heart) Tumors, Lymphoma, Primary, Cervical Cancer, Childhood Cancers, Chordoma, Chronic Lymphocytic Leukemia, Chronic Myelogenous Leukemia, Chronic Myeloproliferative Neoplasms Colon Cancer, Colorectal Cancer, Cutaneous T-Cell Lymphoma, Ductal Carcinoma In Situ, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Intraocular Melanoma, Retinoblastoma, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors, Extragonadal Cancer, Ovarian Cancer, Testicular Cancer, Gestational Trophoblastic Disease, Glioma, Brain Stem Cancer, Hairy Cell Leukemia, Head and Neck Cancer, Heart Cancer, Hepatocellular (Liver) Cancer, Histiocytosis, Langerhans Cell Cancer, Hodgkin Lymphoma, Hypopharyngeal Cancer, Intraocular Melanoma, Islet Cell Tumors, Pancreatic Neuroendocrine Tumors, Kaposi Sarcoma, Kidney Cancer, Renal Cell Cancer, Wilms Tumor and Other Childhood Kidney Tumors, Langerhans Cell Histiocytosis, Laryngeal Cancer, Leukemia, Chronic Lymphocytic Cancer, Chronic Myelogenous Cancer, Hairy Cell Cancer, Lip and Oral Cavity Cancer, Liver Cancer (Primary), Lobular Carcinoma In Situ (LCIS), Lung Cancer, Non-Small Cell Cancer, Small Cell Cancer, Lymphoma, Cutaneous T-Cell (Mycosis Fungoides and Sézary Syndrome), Hodgkin Cancer, Non-Hodgkin Cancer, Macroglobulinemia, Waldenström, Male Breast Cancer, Malignant Fibrous Histiocytoma of Bone and Osteosarcoma, Melanoma, Intraocular (Eye) Cancer, Merkel Cell Carcinoma, Mesothelioma, Malignant, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic, Myeloid Leukemia, Acute, Myeloma Multiple, Chronic Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and Oropharyngeal Cancer, Osteosarcoma and Malignant Fibrous Histiocytoma of Bone, Epithelial Cancer, Low Malignant Potential Tumor, Pancreatic Cancer, Pancreatic Neuroendocrine Tumors (Islet Cell Tumors), Papillomatosis, Paraganglioma, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System Lymphoma, Rectal Cancer, Renal Cell (Kidney) Cancer, Retinoblastoma, Rhabdomyosarcoma, Salivary Gland Cancer, Sarcoma, Ewing Cancer, Kaposi Cancer, Osteosarcoma (Bone Cancer), Soft Tissue Cancer, Uterine Cancer, Sézary Syndrome, Skin Cancer, Childhood Melanoma, Merkel Cell Carcinoma, Nonmelanoma, Small Cell Lung Cancer, Small Intestine Cancer, Soft Tissue Sarcoma, Squamous Cell Carcinoma, Skin Cancer (Nonmelanoma), Childhood Squamous Neck Cancer with Occult Primary, Metastatic Cancer, Stomach (Gastric) Cancer, T-Cell Lymphoma, Cutaneous Cancer, Testicular Cancer, Throat Cancer, Thymoma and Thymic Carcinoma, Thyroid Cancer, Transitional Cell Cancer of the Renal Pelvis and Ureter, Unknown Primary, Carcinoma of Childhood, Unusual Cancers of Childhood, Urethral Cancer, Uterine Cancer, Endometrial Cancer, Uterine Sarcoma, Vaginal Cancer, Vulvar Cancer, Waldenström Macroglobulinemia, Wilms Tumor, and Women's Cancers.

In a specific embodiment, the cancer is glioblastoma, small cell lung carcinoma, breast cancer and/or prostate cancer. In another embodiment, the administration of the Parkin ligase suppresses one or more tumors in the subject.

In another specific embodiment, the compound eliminates damaged mitochondria, increases cell viability during cellular stress, decreases tumor transformation and/or mitigates alpha-synuclein in cells.

In another embodiment, the methods of the present invention include treating and/or reducing the incidence of Parkinson's disease, specifically by administering to a subject in need thereof a therapeutically effective amount of one or more compounds that disrupt at least one Parkin ligase zinc finger and induces Parkin ligase activity, wherein the compound can coordinate with a Zn ion and/or react with a thiol group in a cysteine(s). In another embodiment, the one or more compounds eliminate damaged mitochondria, increases cell viability during cellular stress and/or mitigates alpha-synuclein in cells. "Somatic Mutations of the Parkinson's disease-associated gene PARK2 in glioblastoma and other human malignancies" (*Nature Genetics* January 2010 42(1)77-82).

In another embodiment, the Parkin ligase activation alters ubiquitination. Specifically, the alteration of ubiquitination is caused by the ability of Parkin to modify a substrate protein by covalent attachment of Ubiquitin, a substrate protein being Parkin itself, or another protein such as Mitofusion 1 or 2, FBW7, or other publicly reported substrates of Parkin ligase.

In a specific embodiment, the methods of the present invention include treating and/or reducing the incidence of cancer, comprising administering to a subject in need thereof a therapeutically effective amount of a compound that disrupts at least one Parkin ligase zinc finger and induces Parkin ligase activity, wherein the compound can coordinate with a zinc ion and/or bind or react with a cysteine. In a specific embodiment, the compound is from Table 1 or Table 2 or a salt or ester thereof. In a specific embodiment, the Parkin ligase suppresses the growth of one or more tumors and/or prevents metastasis of one or more tumors. In another embodiment, the compound eliminates damaged mitochondria, increases cell viability during cellular stress, decreases tumor transformation and/or mitigates alpha-synuclein in cells. In another embodiment, the cancer is glioblastoma, small cell lung carcinoma, breast cancer or prostate cancer.

In another embodiment, the compound for treating and/or reducing the incidence of cancer can coordinate to a Zn ion as a monodentate, bidentate, or tridentate ligand. In another embodiment, the compound for treating and/or reducing the incidence of cancer can coordinate to a Zn ion substantially which disrupts the structure of at least one zinc finger in the Parkin ligase. In another embodiment, the amino acid residues of at least one zinc finger corresponds to or aligns with one or more amino acid domains selected from the group consisting R0 amino acids 141-216, IBR amino acids 328-377, and R2 amino acids 415-465 of human Parkin Ligase. In another embodiment, the compound substantially disrupts the structure of at least one zinc finger located in the IBR domain (amino acids 328-377). In another embodiment, the zinc finger comprises four cysteine residues. In another embodiment, the Parkin ligase activation alters ubiquitination. In another embodiment, the compound binds or reacts with the thiol group in a cysteine. In another embodiment, the cysteine is selected from one or more of the group consisting of C59 and C377 of human Parkin ligase. In another embodiment, the cysteine is C377 of human Parkin ligase. In another embodiment, the compound the compound is AH001 and/or AH007.

In another embodiment, the compound for treating and/or reducing the incidence of cancer is an alkylator, oxidant, Michael acceptor, another unsaturated structure, and/or has a disulfide. In a specific embodiment, this compound also substantially disrupts the structure of at least one zinc finger in the Parkin ligase. In another embodiment, the amino acid residues of the at least one zinc finger corresponds to or aligns with one or more amino acid domains selected from the group consisting R0 amino acids 141-216, IBR amino acids 328-377, and R2 amino acids 415-465 of human Parkin Ligase. In another embodiment, the zinc finger comprises four cysteine residues.

In a specific embodiment, the methods of the present invention include treating and/or reducing the incidence of Parkinson's disease, comprising administering to a subject in need thereof a therapeutically effective amount of a compound that disrupts at least one Parkin ligase zinc finger and induces Parkin ligase activity, wherein the compound can coordinate with a zinc ion and/or bind or react with a cysteine. In a specific embodiment, the compound is from Table 1 or Table 2 or a salt or ester thereof. In a specific embodiment, the compound eliminates damaged mitochondria, increases cell viability during cellular stress and/or mitigates alpha-synuclein in cells. In another embodiment, the compound that can coordinate to a zinc ion is a monodentate, bidentate, or tridentate ligand. In another embodiment, the amino acid residues of at least one zinc finger corresponds to or aligns with one or more amino acid domains selected from the group consisting R0 amino acids 141-216, IBR amino acids 328-377, and R2 amino acids 415-465 of human Parkin Ligase. In another embodiment, the compound substantially disrupts the structure of at least one zinc finger located in the IBR domain (amino acids 328-377). In another embodiment, the zinc finger comprises four cysteine residues. In another embodiment, the Parkin ligase activation alters ubiquitination. In another embodiment, the compound binds or reacts with the thiol group in a cysteine. In another embodiment, the cysteine is selected from one or more of the group consisting of C59 and C377 of human Parkin ligase. In another embodiment, the cysteine is C377 of human Parkin ligase. In another embodiment, the compound the compound is AH001 and/or AH007.

In another embodiment, the Parkin ligase activation alters ubiquitination wherein the alteration of ubiquitination is caused by the ability of Parkin to modify a substrate protein by covalent attachment of Ubiquitin, a substrate protein being Parkin itself, or another protein such as Mitofusion 1 or 2, FBW7, or other publicly reported substrates of Parkin ligase. In a specific embodiment, a compound induces Parkin ligase activation. In another embodiment, the compound is from Table 1 or Table 2 or a salt or ester thereof. In another embodiment, the compound is an alkylator, oxidant, Michael acceptor, another unsaturated structure, or has a disulfide. In another embodiment, the compound substantially disrupts the structure of at least one zinc finger in the Parkin ligase. In another embodiment, the amino acid residues of at least one zinc finger corresponds to or aligns with one or more amino acid domains selected from the group consisting R0 amino acids 141-216, IBR amino acids 328-377, and R2 amino acids 415-465 of human Parkin Ligase. In another embodiment, the compound substantially disrupts the structure of at least one zinc finger located in the IBR domain (amino acids 328-377). In another embodiment, the zinc finger comprises four cysteine residues. In another embodiment, the Parkin ligase activation alters ubiquitination. In another embodiment, the compound binds or reacts with the thiol group in a cysteine. In another embodiment, the cysteine is selected from one or more of the group consisting of C59 and C377 of human Parkin ligase. In another embodiment, the cysteine is C377 of human Parkin ligase. In another embodiment, the compound the compound is AH001 and/or AH007.

While proteins are built-up to cater for the structural and biochemical requirements of the cell, they are also broken-down in a highly-regulated process serving more purposes than just destruction and space management. Proteins have different half-lives, determined by the nature of the amino acids present at their N-termini. Some will be long-lived, while other will rapidly be degraded. Proteolysis not only enables the cell to dispose of misfolded or damaged proteins, but also to fine-tune the concentration of essential proteins within the cell, such as the proteins involved in the cell cycle. This rapid, highly specific degradation can be achieved through the addition of one to several ubiquitin molecules to a target protein. The process is called ubiquitination.

Ubiquitination is crucial for a plethora of physiological processes, including cell survival and differentiation and innate and adaptive immunity. In recent years, considerable progress has been made in the understanding of the molecular action of ubiquitin in signaling pathways and how alterations in the ubiquitin system lead to the development of distinct human diseases. It has been shown that ubiquitination plays a role in the onset and progression of cancer, metabolic syndromes, neurodegenerative diseases, autoimmunity, inflammatory disorders, infection and muscle dystrophies (Popovic et al. *Nature Medicine* 20, 1242-1253 (2014)).

Some embodiments of the present invention relate to methods of treating, preventing, or ameliorating one or more symptoms of diseases or disorders associated with but not limited to solid tumors, such as glioma (oligodenrogliomas, mixed gliomas and glioblastomas), lung cancer, breast cancer, prostate cancer, ovarian cancer, and Warburg effect in tumors (restoration of Parkin activity to prevent Warburg effect). Human genetic and pathology data support Parkin protein as a high value target. If there is not enough activated Parkin, then cell death and loss of dopamine neurons occurs. ("Familial Parkinson Disease Gene Product, Parkin, Is a Ubiquitin-Protein Ligase" Nature Genetics 25, 302-305, 1 Jul. 2000).

Further embodiments of the present invention relate to methods of treating, preventing, or ameliorating one or more symptoms associated with neurological diseases or disorders including but not limited to Alzheimer's Dementia, Parkinson's disease, Huntington Disease, Amyotrophic Lateral Sclerosis (ALS), Freidreich's ataxia, Spinocerebellar Ataxia, Multiple Systems Atrophy, PSP, Tauopathy, Diffuse Lewy Body Disease, Lewy Body dementia, any disorder characterized by abnormal accumulation of α-synuclein, disorders of the aging process, and stroke.

Other embodiments of the present invention relate to methods of treating, preventing, or ameliorating one or more symptoms associated with but not limited to mental retardation, deafness, blindness, diabetes, obesity, cardiovascular disease, and autoimmune diseases such as multiple sclerosis, Sjogrens syndrome, lupus, glaucoma, including pseudoexfoliation glaucoma, Leber's Hereditary Optic Neuropathy, and rheumatoid arthritis.

Further embodiments of the present invention of the present invention relate to methods of treating, preventing, or ameliorating one or more symptoms associated with but not limited to Mitochondrial Related Diseases or Capsules as follows:

Alpers Disease
Barth Syndrome/LIC (Lethal Infantile Cardiomyopathy)
Beta-oxidation Defects
Carnitine-Acyl-Carnitine Deficiency
Carnitine Deficiency
Creatine Deficiency Syndromes
Co-Enzyme Q10 Deficiency
Complex I Deficiency
Complex II Deficiency
Complex III Deficiency
Complex IV Deficiency/COX Deficiency
Complex V Deficiency
CPEO
CPT I Deficiency
CPT II Deficiency
KSS
Lactic Acidosis
LBSL—Leukodystrohpy
LCAD
LCHAD
Leigh Disease or Syndrome
Luft Disease
MAD/Glutaric Aciduria Type II
MCAD
MELAS
MERRF
MIRAS
Mitochondrial Cytopathy
Mitochondrial DNA Depletion
Mitochondrial Encephalopathy
Mitochondrial Myopathy
MNGIE
NARP
Pearson Syndrome
Pyruvate Carboxylase Deficiency
Pyruvate Dehydrogenase Deficiency
POLG Mutations
Respiratory Chain
SCAD
SCHAD
VLCAD.

Increased Parkin activity eliminates damaged mitochondria (red) and increases cell viability during cellular stress, decreasing tumor transformation and mitigating α-synuclein in cells. Multiple diverse Parkin activating compounds were identified that remove zinc from Parkin. Activation after ZnF unfolding is similar to other known ZnF proteins.

The present invention also includes pharmaceutical compositions for activating a Parkin ligase in a subject. In a specific embodiment, the pharmaceutical compositions comprise one or more compounds or the salts thereof that disrupt at least one Parkin ligase zinc finger. In a specific embodiment, the one or more compounds or the salts thereof can coordinate with a Zn ion, and/or react with at least one thiol group in a cysteine. In a specific embodiment, the pharmaceutical compositions may comprise one or more compounds selected from the group consisting of the compounds in Table 1 and Table 2.

In another embodiment, the compounds, methods and pharmaceutical compositions in the present invention may be from one or more of following drug classes: 8-hydroxyquinolines; alpha-hydroxyketone; aminomethyl benzimidazoles; aminomethyl indoles; barbiturates; benzisothiazolones, carboxylate, dithiobisbenzamides, dithiocarbamates, formamides, hydrazides, hydroxamates, hydroxypyridinones/hydroxypyranones, hydroxysulfonamides, imidazoles, ketone hydrates, N-acyl ortho-phenylenediamines, N-hydroxyureas, O-substituted phosphamates, phosphamates, phosphones, sulfamates, sulfamides, sulfodiimines, sulfonamides, thiadiazines, thiadiazolothiones, and thiols. For example, the following list in Table 1 is representative, but not an exhaustive list of potential compounds that may be used in the present invention.

TABLE 1

Examples of potential compounds

| No | Class | Structure | IUPAC names | Common Name(s) | References |
|---|---|---|---|---|---|
| 1 | 8-hydroxyquinolines | 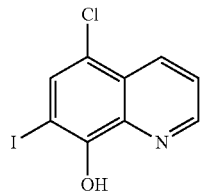 [SMILES: Oc1c(I)cc(Cl)c2cccnc12] | 5-chloro-7-iodoquinolin-8-ol | clioquinol 5-chloro-7-iodo-8-hydroxyquinoline | Biochem. J. 2009, 417, 133. |

TABLE 1-continued

Examples of potential compounds

| No | Class | Structure | IUPAC names | Common Name(s) | References |
|---|---|---|---|---|---|
| 2 | 8-hydroxyquinolines | 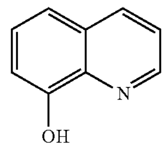 [SMILES: Oc1cccc2cccnc12] | Quinolin-8-ol | 8-hydroxy-quinoline | Drug Design, Development and Therapy 2013, 7, 1157. |
| 3 | 8-hydroxyquinolines | 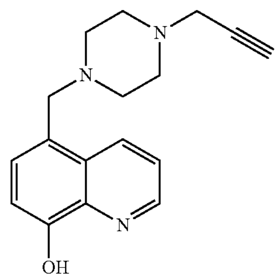 [SMILES: C#CCN1CCN(Cc2ccc(O)c3ncccc23)CC1] | 5-((4-(prop-2-yn-1-yl)piperazin-1-yl)methyl)quinolin-8-ol | HLA-20 | Drug Design, Development and Therapy 2013, 7, 1157. |
| 4 | 8-hydroxyquinolines | 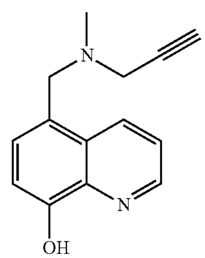 [SMILES: C#CCN(C)Cc1ccc(O)c2ncccc12] | 5-((methyl(prop-2-yn-1-yl)amino)methyl)quinolin-8-ol | M30 | Drug Design, Development and Therapy 2013, 7, 1157. |
| 5 | 8-hydroxyquinolines | 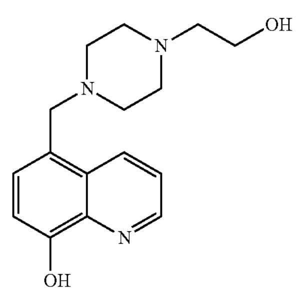 [SMILES: OCCN1CCN(Cc2ccc(O)c3ncccc23)CC1] | 5-((4-(2-hydroxyethyl)piperazin-1-yl)methyl)quinolin-8-ol | VK-28 | Drug Design, Development and Therapy 2013, 7, 1157. |
| 6 | 8-hydroxyquinolines | 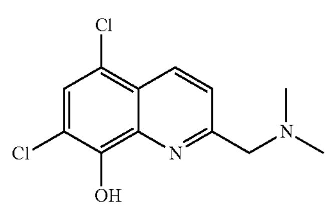 [SMILES: CN(C)Cc1ccc2c(Cl)cc(Cl)c(O)c2n1] | 5,7-dichloro-2-((dimethylamino)methyl)quinolin-8-ol | PBT2 | Drug Design, Development and Therapy 2013, 7, 1157. |
| 7 | 8-hydroxyquinolines | 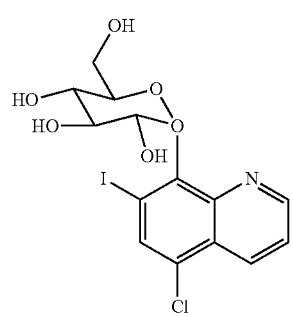 | (3S,4S,5S,6R)-2-(5-chloro-7-iodoquinolin-8-yl)-6-(hydroxymethyl)-1,2l3-dioxane-3,4,5-triol | GluCQ | Drug Design, Development and Therapy 2013, 7, 1157. |

TABLE 1-continued

Examples of potential compounds

| No | Class | Structure | IUPAC names | Common Name(s) | References |
|---|---|---|---|---|---|
| 8 | 8-hydroxyquinolines | 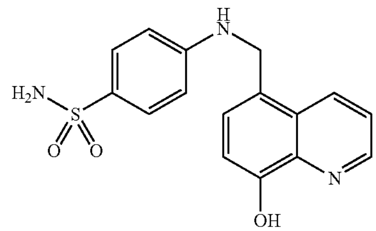 [SMILES: NS(=O)(=O)c1ccc(NCc2ccc(O)c3ncccc23)cc1] | 4-(((8-hydroxyquinolin-5-yl)methyl)amino)benzenesulfonamide | HQMABS | *Drug Design, Development and Therapy* 2013, 7, 1157. |
| 9 | 8-hydroxyquinolines | 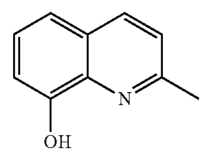 | 2-methylquinolin-8-ol | 8-hydroxyquinaldine | *Drug Design, Development and Therapy* 2013, 7, 1157. |
| 10 | alpha-hydroxyketone | 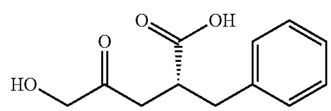 [SMILES: O=C(CO)C[C@@H](Cc1ccccc1)C(=O)O] | (2r)-2-benzyl-5-hydroxy-4-oxopentanoic acid | | *Chin. Chem. Lett.* 2010, 21, 159 |
| 11 | aminomethyl benzimidazoles | 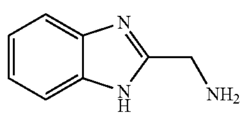 [SMILES: NCc1nc2ccccc2[nH]1] | (1H-benzo[d]imidazol-2-yl)methanamine | | *Bioorg. Med. Chem. Lett.* 2002, 12, 2201 |
| 12 | aminomethyl benzimidazoles | 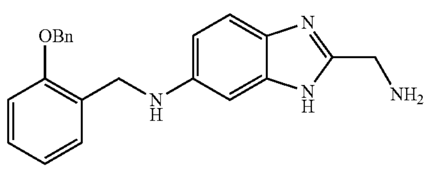 [SMILES: NCc1nc2ccc(NCc3ccccc3OCc3ccccc3)cc2[nH]1] | 2-(aminomethyl)-N-(2-(benzyloxy)benzyl)-1H-benzo[d]imidazol-6-amine | | *Bioorg. Med. Chem. Lett.* 2002, 12, 2201 |
| 13 | aminomethyl benzimidazoles | 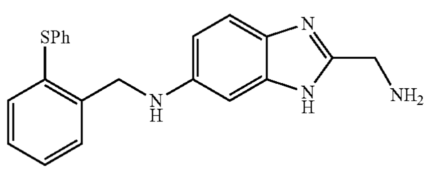 | 2-(aminomethyl)-N-(2-(phenylthio)benzyl)-1H-benzo[d]imidazol-6-amine | | *Bioorg. Med. Chem. Lett.* 2002, 12, 2201 |
| 14 | aminomethyl benzimidazoles | 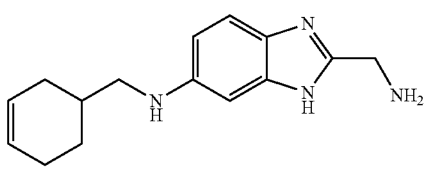 [SMILES: NCc1nc2ccc(NCC3CC=CCC3)cc2[nH]1] | 2-(aminomethyl)-N-(cyclohex-3-en-1-ylmethyl)-1H-benzo[d]imidazol-6-amine | | *Bioorg. Med. Chem. Lett.* 2002, 12, 2201 |
| 15 | aminomethyl benzimidazoles | 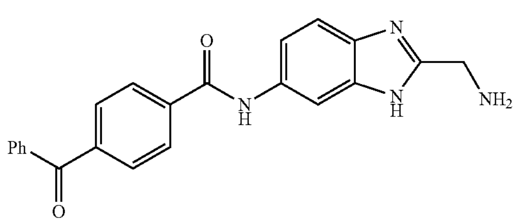 [SMILES: NCc1nc2ccc(NC(=O)c3ccc(C(=O)c4ccccc4)cc3)cc2[nH]1] | N-(2-(aminomethyl)-1H-benzo[d]imidazol-6-yl)-4-benzoylbenzamide | | *Bioorg. Med. Chem. Lett.* 2002, 12, 2201 |

TABLE 1-continued

Examples of potential compounds

| No | Class | Structure | IUPAC names | Common Name(s) | References |
|---|---|---|---|---|---|
| 16 | aminomethyl benzimidazoles | 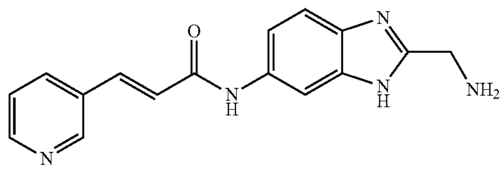 [SMILES: NCc1nc2ccc(NC(=O)/C=C/c3cccnc3)cc2[nH]1] | (E)-N-(2-(aminomethyl)-1H-benzo[d]imidazol-6-yl)-3-(pyridin-3-yl)acrylamide | | Bioorg. Med. Chem. Lett. 2002, 12, 2201 |
| 17 | aminomethyl benzimidazoles | | (E)-N-(2-(aminomethyl)-1H-benzo[d]imidazol-6-yl)-3-(2,6-difluorophenyl)acrylamide | | Bioorg. Med. Chem. Lett. 2002, 12, 2201 |
| 18 | aminomethyl benzimidazoles | 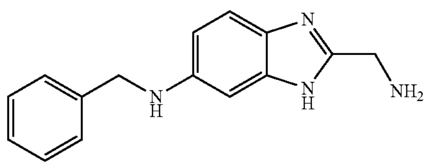 [SMILES: NCc1nc2ccc(NCc3ccccc3)cc2[nH]1] | 2-(aminomethyl)-N-benzyl-1H-benzo[d]imidazol-6-amine | | Bioorg. Med. Chem. Lett. 2002, 12, 2201 |
| 19 | aminomethyl benzimidazoles | 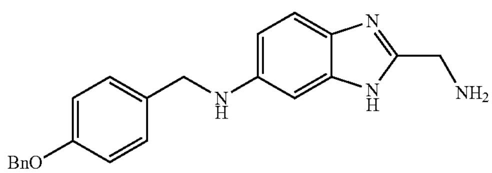 [SMILES: NCc1nc2ccc(NCc3ccc(OCc4ccccc4)cc3)cc2[nH]1] | 2-(aminomethyl)-N-(4-(benzyloxy)benzyl)-1H-benzo[d]imidazol-6-amine | | Bioorg. Med. Chem. Lett. 2002, 12, 2201 |
| 20 | aminomethyl benzimidazoles | 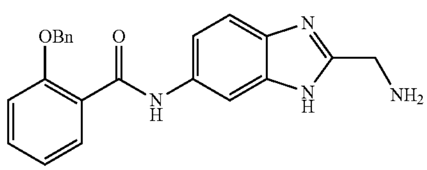 [SMILES: NCc1nc2ccc(NC(=O)c3ccccc3OCc3ccccc3)cc2[nH]1] | N-(2-(aminomethyl)-1H-benzo[d]imidazol-6-yl)-2-(benzyloxy)benzamide | | Bioorg. Med. Chem. Lett. 2002, 12, 2201 |
| 21 | aminomethyl benzimidazoles | 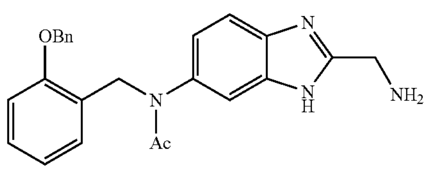 [SMILES: CC(=O)N(Cc1ccccc1OCc1ccccc1)c1ccc2nc(CN)[nH]c2c1] | N-(2-(aminomethyl)-1H-benzo[d]imidazol-6-yl)-N-(2-(benzyloxy)benzyl)acetamide | | Bioorg. Med. Chem. Lett. 2002, 12, 2201 |
| 22 | aminomethyl indoles | 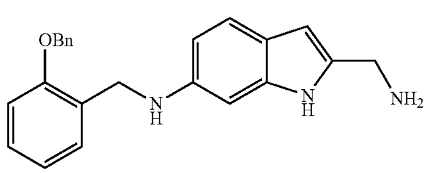 [SMILES: NCc1cc2ccc(NCc3ccccc3OCc3ccccc3)cc2[nH]1] | 2-(aminomethyl)-N-(2-(benzyloxy)benzyl)-1H-indol-6-amine | | Bioorg. Med. Chem. Lett. 2002, 12, 2201 |
| 23 | barbiturates | 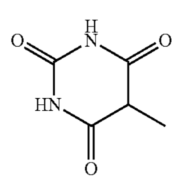 | 5-methylpyrimidine-2,4,6(1H,3H,5H)-trione | | J. Biol. Chem. 2001, 276, 17405. Protein Sci. 2001, 10, 923. Curr. Pharm. Des. 2005, 11, 295. |

TABLE 1-continued

Examples of potential compounds

| No | Class | Structure | IUPAC names | Common Name(s) | References |
|---|---|---|---|---|---|
| 24 | barbiturates | 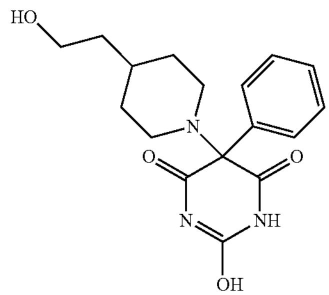 [SMILES: O=C1N=C(O)NC(=O)C1(c1ccccc1)N1CCC(CCO)CC1] | 2-hydroxy-5-[4-(2-hydroxy-ethyl)-piperidin-1-yl]-5-phenyl-1h-pyrimidine-4,6-dione | | *J. Biol. Chem.* 2001, 276, 17405 |
| 25 | benzisothiazolones | 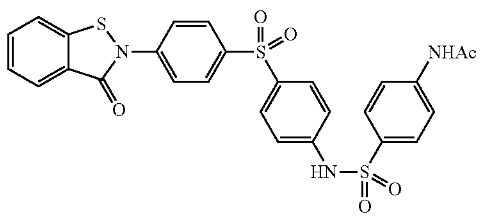 [SMILES: CC(=O)Nc1ccc(S(=O)(=O)Nc2ccc(S(=O)(=O)c3ccc(-n4sc5ccccc5c4=O)cc3)cc2)cc1] | N-(4-(N-(4-((4-(3-oxobenzo[d]isothiazol-2(3H)-yl)phenyl)sulfonyl)phenyl)sulfamoyl)phenyl)acetamide | BITA | *Nature Medicine* 2004, 10(1), 40. |
| 26 | carboxylate | 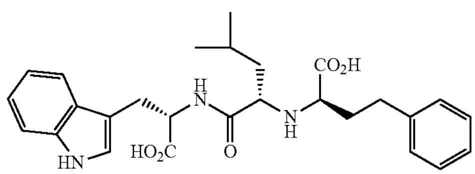 [SMILES: CC(C)C[C@H](N[C@H](CCc1ccccc1)C(=O)O)C(=O)N[C@@H](Cc1c[nH]c2ccccc12)C(=O)O] | N-[(1r)-1-carboxy-3-phenylpropyl]-1-leucyl-1-tryptophan | | *Biochemistry* 1984, 23, 5724 |
| 27 | dithiobisbenzamides | 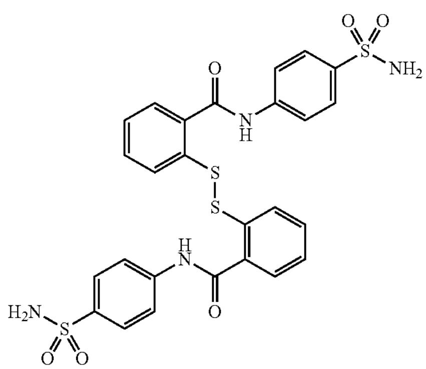 [SMILES: NS(=O)(=O)c1ccc(NC(=O)c2ccccc2SSc2ccccc2C(=O)Nc2ccc(S(N)(=O)=O)cc2)cc1] | 2,2'-disulfanediylbis(N-(4-sulfamoylphenyl)benzamide) | DIBA NSC 654077 | *J. Med. Chem.* 1996, 39, 3606. *Nature Medicine* 2004, 10, 40. |
| 28 | dithiocarbamates | 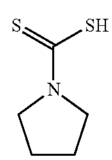 | Pyrrolidine-1-carbodithioic acid | 1-Pyrrolidine-carbodithioic acid PyDT | |
| 29 | dithiocarbamates | 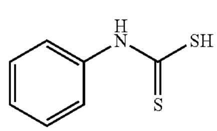 | Phenyl-carbamodithioic acid | | *J. Med. Chem.* 2012, 55, 1721. |
| 30 | dithiocarbamates | 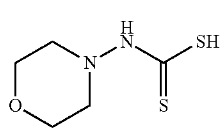 | Morpholino-carbamodithioic acid | | *J. Med. Chem.* 2012, 55, 1721. |

TABLE 1-continued

Examples of potential compounds

| No | Class | Structure | IUPAC names | Common Name(s) | References |
|---|---|---|---|---|---|
| 31 | dithiocarbamates | 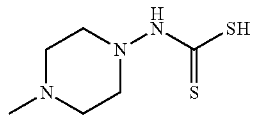 | (4-methylpiperazin-1-yl)carbamodithioic acid | N-(4-methyl-1-piperazinyl)carbamodithioic acid | J. Med. Chem. 2012, 55, 1721. |
| 32 | dithiocarbamates | 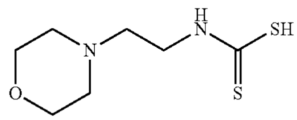 [SMILES: S=C(S)NCCN1CCOCC1] | (2-morpholinoethyl)carbamodithioic acid | | J. Med. Chem. 2012, 55, 1721. |
| 33 | dithiocarbamates | 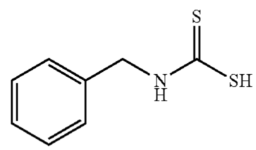 [SMILES: S=C(S)NCc1ccccc1] | Benzyl-carbamodithioic acid | | J. Med. Chem. 2012, 55, 1721. |
| 34 | dithiocarbamates | 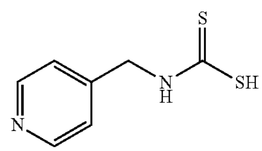 [SMILES: S=C(S)NCc1ccncc1] | (Pyridin-4-ylmethyl)carbamodithioic acid | | J. Med. Chem. 2012, 55, 1721. |
| 35 | dithiocarbamates | 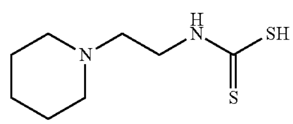 [SMILES: S=C(S)NCCN1CCCCC1] | (2-(piperidin-1-yl)ethyl)carbamodithioic acid | | J. Med. Chem. 2012, 55, 1721. |
| 36 | dithiocarbamates | 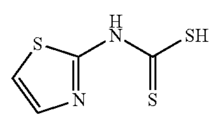 | Thiazol-2-ylcarbamodithioic acid | | J. Med. Chem. 2012, 55, 1721. |
| 37 | dithiocarbamates | 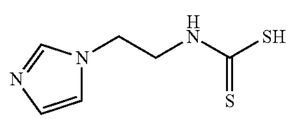 [SMILES: S=C(S)NCCn1ccnc1] | (2-(1H-imidazol-1-yl)ethyl)carbamodithioic acid | | J. Med. Chem. 2012, 55, 1721. |
| 38 | dithiocarbamates | 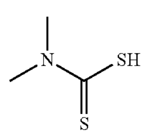 | Dimethyl-carbamodithioic acid | | J. Med. Chem. 2012, 55, 1721. |
| 39 | dithiocarbamates | 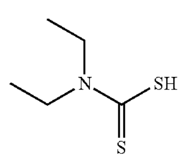 | Diethyl-carbamodithioic acid | | J. Med. Chem. 2012, 55, 1721. |
| 40 | dithiocarbamates | 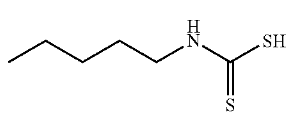 | Pentyl-carbamodithioic acid | | J. Med. Chem. 2012, 55, 1721. |
| 41 | dithiocarbamates | 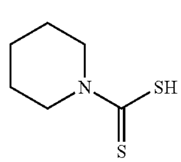 | Piperidine-1-carbodithioic acid | | J. Med. Chem. 2012, 55, 1721. |

TABLE 1-continued

Examples of potential compounds

| No | Class | Structure | IUPAC names | Common Name(s) | References |
|---|---|---|---|---|---|
| 42 | dithiocarbamates | 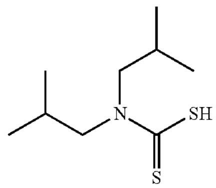 | Diisobutyl-carbamodithioic acid | | J. Med. Chem. 2012, 55, 1721. |
| 43 | dithiocarbamates | 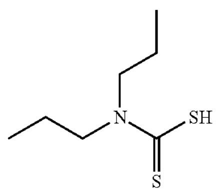 | Dipropyl-carbamodithioic acid | | J. Med. Chem. 2012, 55, 1721. |
| 44 | dithiocarbamates | 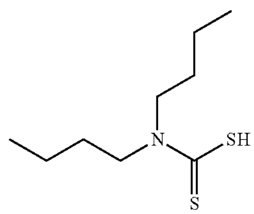 | Dibutyl-carbamodithioic acid | | J. Med. Chem. 2012, 55, 1721. |
| 45 | dithiocarbamates | 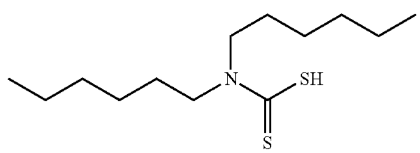 [SMILES: CCCCCCN(CCCCCC)C(=S)S] | Dihexyl-carbamodithioic acid | | J. Med. Chem. 2012, 55, 1721. |
| 46 | dithiocarbamates | 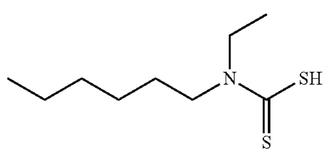 | Ethyl(hexyl) carbamodithioic acid | | J. Med. Chem. 2012, 55, 1721. |
| 47 | dithiocarbamates | 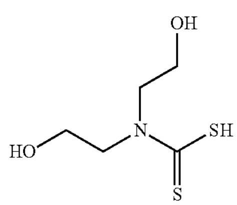 | Bis(2-hydroxyethyl) carbamodithioic acid | | J. Med. Chem. 2012, 55, 1721. |
| 48 | dithiocarbamates | 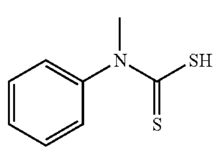 | Methyl(phenyl) carbamodithioic acid | | J. Med. Chem. 2012, 55, 1721. |
| 49 | dithiocarbamates | 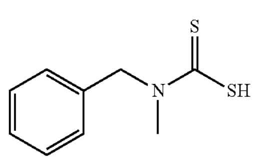 | Benzyl(methyl) carbamodithioic acid | | J. Med. Chem. 2012, 55, 1721. |

TABLE 1-continued

Examples of potential compounds

| No | Class | Structure | IUPAC names | Common Name(s) | References |
|---|---|---|---|---|---|
| 50 | dithiocarbamates | 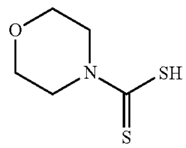 | Morpholine-4-carbodithioic acid | | J. Med. Chem. 2012, 55, 1721. |
| 51 | dithiocarbamates | 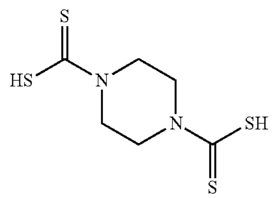 [SMILES: S=C(S)N1CCN(C(=S)S)CC1] | Piperazine-1,4-bis(carbodithioic acid | | J. Med. Chem. 2012, 55, 1721. |
| 52 | dithiocarbamates | 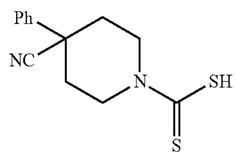 [SMILES: N#CC1(c2ccccc2)CCN(C(=S)S)CC1] | 4-cyano-4-phenylpiperidine-1-carbodithioic acid | | J. Med. Chem. 2012, 55, 1721. |
| 53 | formamide | 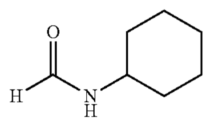 | Cyclohexyl-formamide | | Biochemistry 1997, 36, 3552 |
| 54 | hydrazides | 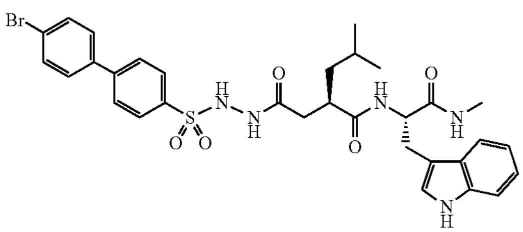 [SMILES: CNC(=O)[C@H](Cc1c[nH]c2ccccc12)NC(=O)[C@@H](CC(=O)NNS(=O)(=O)c1ccc(-c2ccc(Br)cc2)cc1)CC(C)C] | (R)-N-((S)-3-(1H-indol-3-yl)-1-(methylamino)-1-oxopropan-2-yl)-2-(2-(2-((4'-bromo-[1,1'-biphenyl]-4-yl)sulfonyl)hydrazinyl)-2-oxoethyl)-4-methylpentanamide | | Bourguet, E. et al. (2012). Pharmacomodulation of Broad Spectrum Matrix Metalloproteinase Ingibitors Towards Regulation of Gelatinases, Enzyme Inhibition and Bioapplications, Sharma,R. (Ed.), pp. 57-84 |
| 55 | hydroxamates | 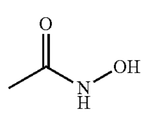 | N-hydroxyacetamide | acetohydroxamic acid | Curr. Pharma. Des. 2005, 11, 295 |
| 56 | hydroxamates | 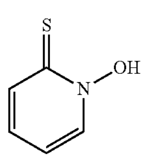 | 1-hydroxypyridine-2(1H)-thione | | J. Biol. Inorg. Chem. 2006, 11, 131. Inorg. Chem. 2003, 42, 3423 |

TABLE 1-continued

Examples of potential compounds

| No | Class | Structure | IUPAC names | Common Name(s) | References |
|---|---|---|---|---|---|
| 57 | hydroxamates | 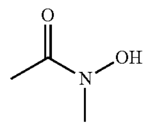 | N-hydroxy-N-methylacetamide | | *Curr. Pharma. Des.* 2005, 11, 295 |
| 58 | hydroxamates | 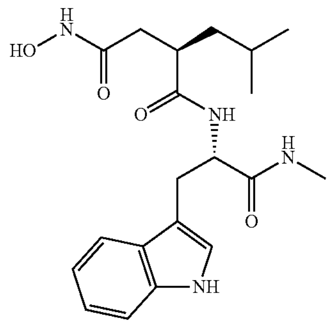 [SMILES: CNC(=O)[C@H](Cc1c[nH]c2ccccc12)NC(=O)[C@@H](CC(=O)NO)CC(C)C] | (R)-N1-((S)-3-(1H-indol-3-yl)-1-(methylamino)-1-oxopropan-2-yl)-N4-hydroxy-2-isobutyl-succinamide | Galardin | |
| 59 | hydroxamates | 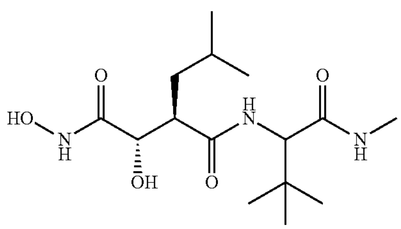 [SMILES: CNC(=O)C(NC(=O)[C@H](CC(C)C)[C@H](O)C(=O)NO)C(C)(C)C] | (2R,3S)-N1-((S)-3,3-dimethyl-1-(methylamino)-1-oxobutan-2-yl)-N4,3-dihydroxy-2-isobutyl-succinamide | marimastat | |
| 60 | hydroxamates | 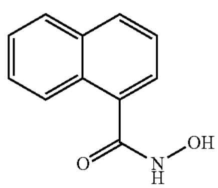 [SMILES: O=C(NO)c1cccc2ccccc12] | N-hydroxy-1-naphthamide | naphthyl hydroxamate | *J. Med. Chem.* 2002, 45, 5628. |
| 61 | hydroxamates | 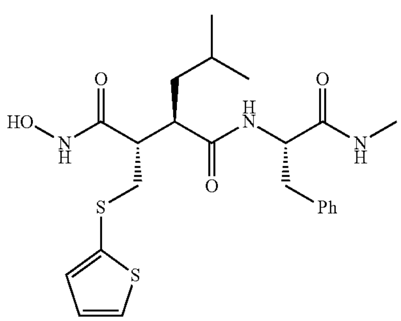 [SMILES: CNC(=O)[C@H](Cc1ccccc1)NC(=O)[C@H](CC(C)C)[C@H](CSc1cccs1)C(=O)NO] | (2S,3R)-N1-hydroxy-3-isobutyl-N4-((S)-1-(methylamino)-1-oxo-3-phenylpropan-2-yl)-2-((thiophen-2-ylthio)methyl)succinamide | batimastat | |
| 62 | hydroxypyridinones/ hydroxypyranones | 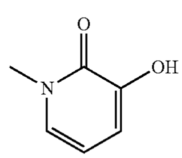 | 3-hydroxy-1-methylpyridin-2(1H)-one | | *J. Biol. Inorg. Chem.* 2006, 11, 131. *Inorg. Chem.* 2003, 42, 3423 |

TABLE 1-continued

Examples of potential compounds

| No | Class | Structure | IUPAC names | Common Name(s) | References |
|---|---|---|---|---|---|
| 63 | hydroxypyridinones/ hydroxypyranones | 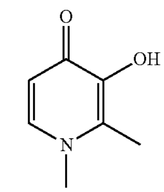 | 3-hydroxy-1,2-dimethylpyridin-4(1H)-one | | J. Biol. Inorg. Chem. 2006, 11, 131. Inorg. Chem. 2003, 42, 3423 |
| 64 | hydroxypyridinones/ hydroxypyranones | 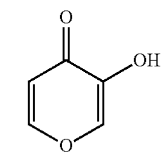 | 3-hydroxy-4H-pyran-4-one | | J. Biol. Inorg. Chem. 2006, 11, 131. Inorg. Chem. 2003, 42, 3423 |
| 65 | hydroxypyridinones/ hydroxypyranones | 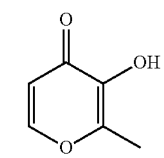 | 3-hydroxy-2-methyl-4H-pyran-4-one | | J. Biol. Inorg. Chem. 2006, 11, 131. Inorg. Chem. 2003, 42, 3423 |
| 66 | hydroxypyridinones/ hydroxypyranones | 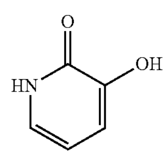 | 3-hydroxypyridin-2(1H)-one | | J. Biol. Inorg. Chem. 2006, 11, 131. Inorg. Chem. 2003, 42, 3423 |
| 67 | hydroxypyridinones/ hydroxypyranones | 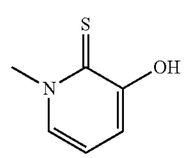 | 3-hydroxy-1-methylpyridine-2(1H)-thione | | J. Biol. Inorg. Chem. 2006, 11, 131. Inorg. Chem. 2003, 42, 3423 |
| 68 | hydroxypyridinones/ hydroxypyranones | 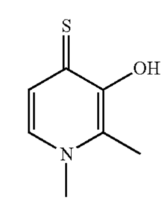 | 3-hydroxy-1,2-dimethylpyridine-4(1H)-thione | | J. Biol. 3423 Inorg. Chem. 2006, 11, 131. Inorg. Chem. 2003, 42, |
| 69 | hydroxypyridinones/ hydroxypyranones | 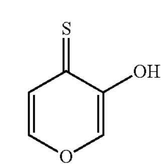 | 3-hydroxy-4H-pyran-4-thione | | J. Biol. Inorg. Chem. 2006, 11, 131. Inorg. Chem. 2003, 42, 3423 |

TABLE 1-continued

Examples of potential compounds

| No | Class | Structure | IUPAC names | Common Name(s) | References |
|---|---|---|---|---|---|
| 70 | hydroxypyridinones/ hydroxypyranones | 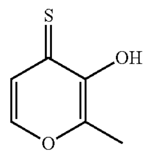 | 3-hydroxy-2-methyl-4H-pyran-4-thione | | *J. Biol. Inorg. Chem.* 2006, 11, 131. *Inorg. Chem.* 2003, 42, 3423 |
| 71 | hydroxysulfonamides | 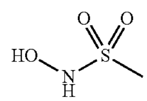 | N-hydroxymethane-sulfonamide | | *J. Med. Chem.* 2000, 43, 3677. |
| 72 | imidazoles | 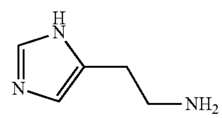 | Histamine | | *Biochemistry* 1997, 36, 10384 |
| 73 | ketone hydrates | 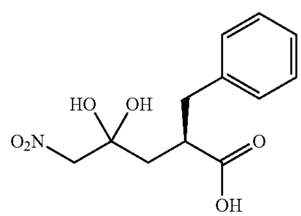 [SMILES: O=C(O)[C@H](Cc1ccccc1)CC(O)(O)C[N+](=O)[O-]] | (2r)-4,4-dihydroxy-5-nitro-2-(phenylmethyl) pentanoic acid | | *Bioorg. Med. Chem. Lett.* 2009, 19, 5009 |
| 74 | ketone hydrates | 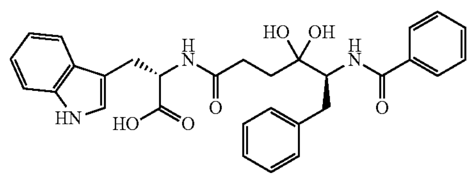 [SMILES: O=C(CCC(O)(O)[C@H](Cc1ccccc1)NC(=O)c1ccccc1)N[C@@H](Cc1c[nH]c2ccccc12)C(=O)O] | N-{(5s)-4,4-dihydroxy-6-phenyl-5-[(phenylcarbonyl) amino] hexanoyl}-1-tryptophan | | *Biochemistry* 2008, 47, 5942 |
| 75 | ketone hydrates | 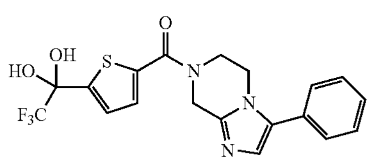 [SMILES: O=C(c1ccc(C(O)(O)C(F)(F)F)s1)N1CCn2c(-c3ccccc3)cnc2C1] | 2,2,2-trifluoro-1-{5-[(3-phenyl-5,6-dihydroimidazo [1,2-a]pyrazin-7(8h)-yl)carbonyl] thiophen-2-yl}ethane-1,1-diol | | *J. Biol. Chem.* 2008, 283, 26694 |
| 76 | N-acyl ortho-phenylenediamines | 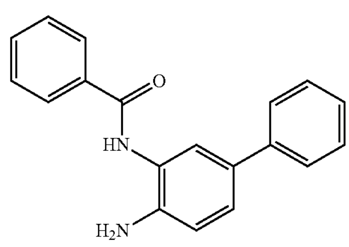 [SMILES: Nc1ccc(-c2ccccc2)cc1NC(=O)c1ccccc1] | N-(4-aminobiphenyl-3-yl)benzamide | | *Bioorg. Med. Chem. Lett.* 2010, 20, 3142 |
| 77 | N-hydroxyureas | 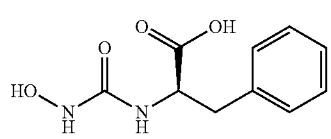 [SMILES: O=C(NO)N[C@H](Cc1ccccc1)C(=O)O] | D-[(n-hydroxyamino) carbonyl] phenylalanine | | *Bioorg. Med. Chem. Lett.* 2002, 10, 2015 |

TABLE 1-continued

Examples of potential compounds

| No | Class | Structure | IUPAC names | Common Name(s) | References |
|---|---|---|---|---|---|
| 78 | O-substituted phosphamates | 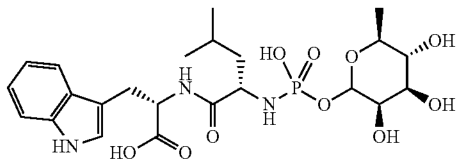 [SMILES: CC(C)C[C@H](NP(=O)(O)OC1O[C@@H](C)[C@H](O)[C@@H](O)[C@H]1O)C(=O)N[C@@H](Cc1c[nH]c2ccccc12)C(=O)O] | N-alpha-1-rhamno-pyranosyloxy (hydroxy-phosphinyl)-1-leucyl-1-tryptophan | | Eur. J. Biochem. 1986, 157, 261 |
| 79 | O-substituted phosphonates | 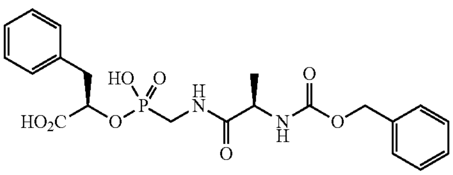 [SMILES: C[C@@H](NC(=O)OCc1ccccc1)C(=O)NCP(=O)(O)O[C@H](Cc1ccccc1)C(=O)O] | O-(((1r)-((n-(phenyl-methoxy-carbonyl)-alanyl)-amino)methyl) hydroxyphosphinyl) 3-1-phenyllactate | | Bio-chemistry 1991, 30, 8171 |
| 80 | phosphamates | 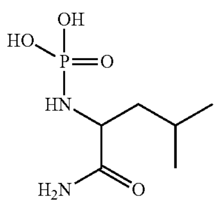 | $N^2$-phosphono-1-leucinamide | | Eur. J. Biochem. 1986, 157, 261 |
| 81 | phosphones | 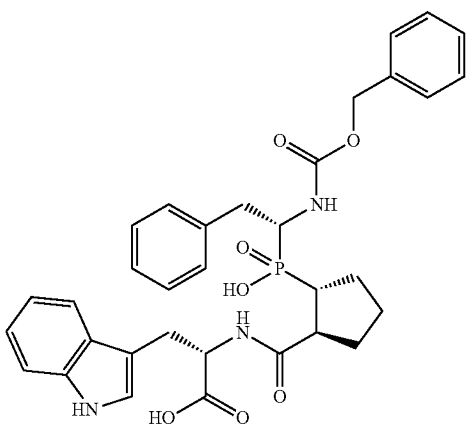 [SMILES: O=C(N[C@@H](Cc1ccccc1)P(=O)(O)[C@@H]1CCC[C@H]1C(=O)N[C@@H](Cc1c[nH]c2ccccc12)C(=O)O)OCc1ccccc1] | N-({(1s,2r)-2-[(s)-[(1r)-1-{[(benzyloxy) carbonyl] amino}-2-phenylethyl] (hydroxy) phosphoryl] cyclopentyl} carbonyl)-1-tryptophan | | J. Mol. Biol. 2010, 400, 502 |
| 82 | sulfamates | 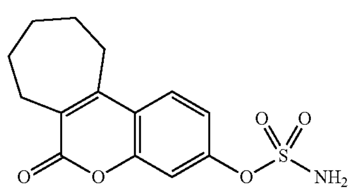 [SMILES: NS(=O)(=O)Oc1ccc2c3c(c(=O)oc2c1)CCCCC3] | 6-oxo-8,9,10,11-tetrahydro-7h-cyclohepta[c][1] benzopyran-3-o-sulfamate | | Biochem. J. 2005, 385, 715 |
| 83 | sulfamides | 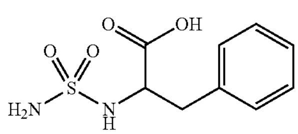 [SMILES: NS(=O)(=O)NC(Cc1ccccc1)C(=O)O] | Phenylalanine-n-sulfonamide | | J. Med. Chem. 2002, 45, 5295 |
| 84 | sulfodiimines | 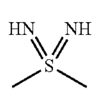 | Dimethyl-$\lambda^6$-sulfanediimine | | Bio-chemistry 1995, 34, 6602 |

TABLE 1-continued

Examples of potential compounds

| No | Class | Structure | IUPAC names | Common Name(s) | References |
|----|-------|-----------|-------------|----------------|------------|
| 85 | sulfodiimines | 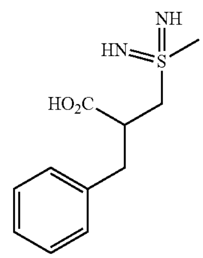 [SMILES: CS(=N)(=N)CC(Cc1ccccc1)C(=O)O] | S-(2-carboxy-3-phenylpropyl) thiodiimine-s-methane | | J. Biol. Chem. 1992, 267, 19192 |
| 86 | sulfonamides | 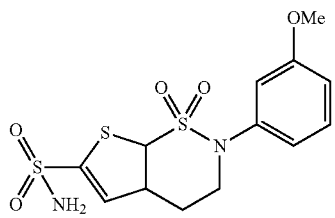 [SMILES: COc1cccc(N2CCC3C=C(S(N)(=O)=O)SC3S2(=O)=O)c1] | 3,,4-dihydro-2-(3-methoxyphenyl)-2h-thieno-[3,2-e]-1,2-thiazine-6-sulfonamide-1,1-dioxide | | Protein Sci. 1998, 7, 2483 |
| 87 | sulfonamides | 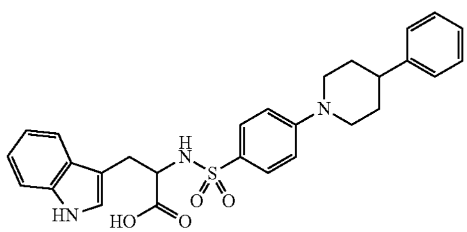 [SMILES: O=C(O)C(Cc1c[nH]c2ccccc12)NS(=O)(=O)c1ccc(N2CCC(c3ccccc3)CC2)cc1] | 3-(1h-indol-3-yl)-2-[4-(4-phenyl-piperidin-1-yl)-benzene-sulfonylamino]-propionic acid | | Protein Sci. 1999, 8, 1455 |
| 88 | thiadiazines | 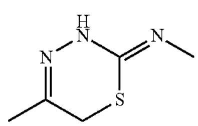 | (Z)-N,5-dimethyl-3,6-dihydro-2H-1,3,4-thiadiazin-2-imine | | J. Med. Chem. 2001, 44, 3231. |
| 89 | thiadiazolothiones | 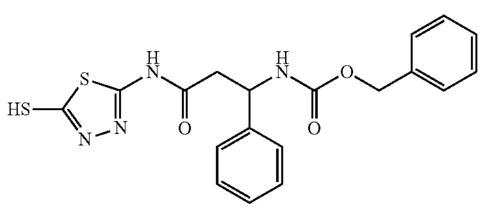 [SMILES: O=C(CC(NC(=O)OCc1ccccc1)c1ccccc1)Nc1nnc(S)s1] | [2-(5-mercapto-[1,3,4]thiadiazol-2-ylcarbamoyl)-1-phenyl-ethyl]-carbamic acid benzyl ester | | Protein Sci. 1998, 7, 2118 |
| 90 | thiols | 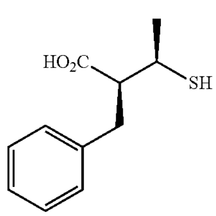 | (2s,3r)-2-benzyl-3-sulfanyl-butanoic acid | | Chem. Biol. Drug Des. 2010, 75, 29 |

TABLE 2

Examples of potential compounds

| No. | COMPOUND STRUCTURE | NAME |
| --- | --- | --- |
| 1 | 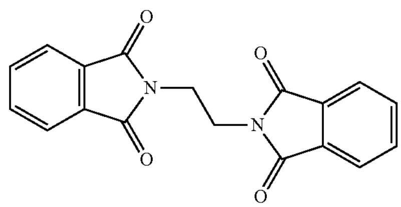 [SMILES: O=C1c2ccccc2C(=O)N1CCN1C(=O)c2ccccc2C1=O] | 2,2'-(ethane-1,2-diyl)bis(isoindoline-1,3-dione) |
| 2 | 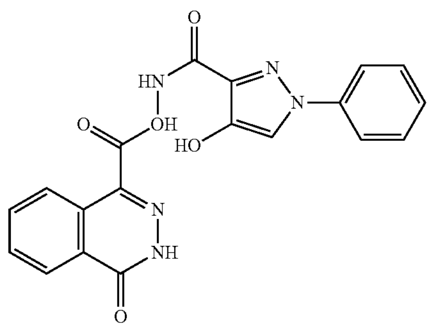 [SMILES: O=C(NOC(=O)c1n[nH]c(=O)c2ccccc12)c1nn(-c2ccccc2)cc1O] | N'-(4-hydroxy-1-phenyl-1H-pyrazole-3-carbonyl)-4-oxo-3,4-dihydrophthalazine-1-carbohydrazide |
| 3 | 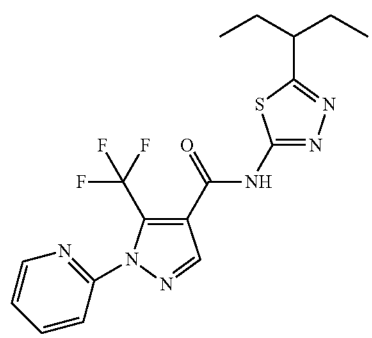 [SMILES: CCC(CC)c1nnc(NC(=O)c2cnn(-c3ccccn3)c2C(F)(F)F)s1] | N-(5-(pentan-3-yl)-1,3,4-thiadiazol-2-yl)-1-(pyridin-2-yl)-5-(trifluoromethyl)-1H-pyrazole-4-carboxamide |
| 4 | 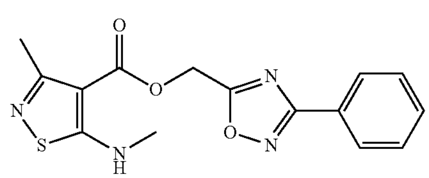 [SMILES: CNc1snc(C)c1C(=O)OCc1nc(-c2ccccc2)no1] | (3-phenyl-1,2,4-oxadiazol-5-yl)methyl 3-methyl-5-(methylamino)isothiazole-4-carboxylate |
| 5 | 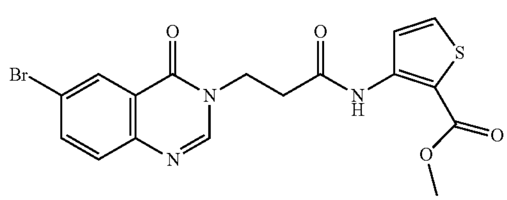 [SMILES: COC(=O)c1sccc1NC(=O)CCn1cnc2ccc(Br)cc2c1=O] | methyl 3-(3-(6-bromo-4-oxoquinazolin-3(4H)-yl)propanamido)thiophene-2-carboxylate |
| 6 | 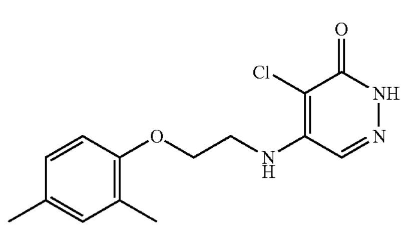 [SMILES: Cc1ccc(OCCNc2cn[nH]c(=O)c2Cl)c(C)c1] | 4-chloro-5-((2-(2,4-dimethylphenoxy)ethyl)amino)pyridazin-3(2H)-one |

TABLE 2-continued

Examples of potential compounds

| No. | COMPOUND STRUCTURE | NAME |
|---|---|---|
| 7 | 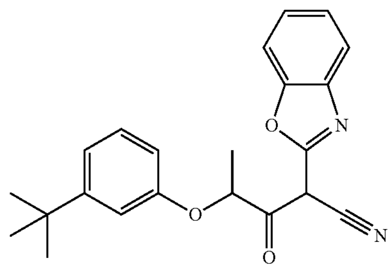 [SMILES: CC(Oc1cccc(C(C)(C)C)c1)C(=O)C(C#N)c1nc2ccccc2o1] | 2-(benzo[d]oxazol-2-yl)-4-(3-(tert-butyl)phenoxy)-3-oxopentanenitrile |
| 8 | 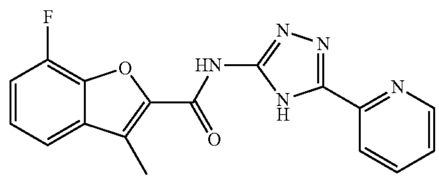 [SMILES: Cc1c(C(=O)Nc2nnc(-c3ccccn3)[nH]2)oc2c(F)cccc12] | 7-fluoro-3-methyl-N-(5-(pyridin-2-yl)-4H-1,2,4-triazol-3-yl)benzofuran-2-carboxamide |
| 9 | 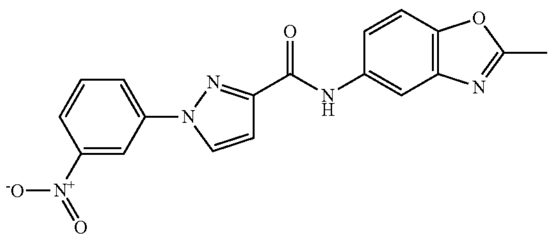 | N-(2-methylbenzo[d]oxazol-5-yl)-1-(3-nitrophenyl)-1H-pyrazole-3-carboxamide |
| 10 | 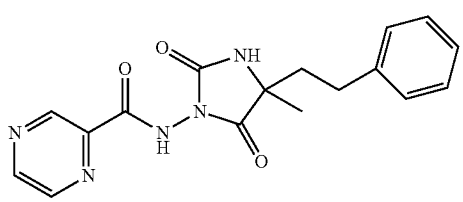 [SMILES: CC1(CCc2ccccc2)NC(=O)N(NC(=O)c2cnccn2)C1=O] | N-(4-methyl-2,5-dioxo-4-phenethylimidazolidin-1-yl)pyrazine-2-carboxamide |
| 11 | 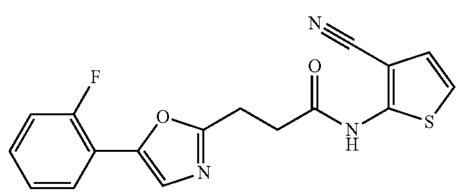 [SMILES: N#Cc1ccsc1NC(=O)CCc1ncc(-c2ccccc2F)o1] | N-(3-cyanothiophen-2-yl)-3-(5-(2-fluorophenyl)oxazol-2-yl)propanamide |
| 12 | 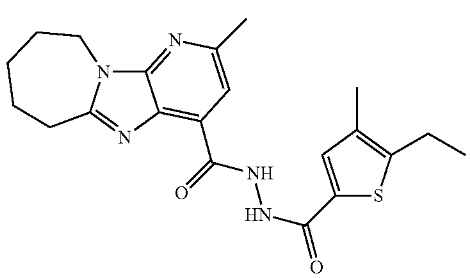 [SMILES: CCc1sc(C(=O)NNC(=O)c2cc(C)nc3c2nc2n3CCCCC2)cc1C] | N'-(5-ethyl-4-methylthiophene-2-carbonyl)-2-methyl-7,8,9,10-tetrahydro-6H-pyrido[3',2':4,5]imidazo[1,2-a]azepine-4-carbohydrazide |
| 13 | 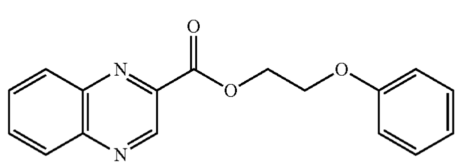 [SMILES: O=C(OCCOc1ccccc1)c1cnc2ccccc2n1] | 2-phenoxyethyl quinoxaline-2-carboxylate |

TABLE 2-continued

Examples of potential compounds

| No. | COMPOUND STRUCTURE | NAME |
|---|---|---|
| 14 | 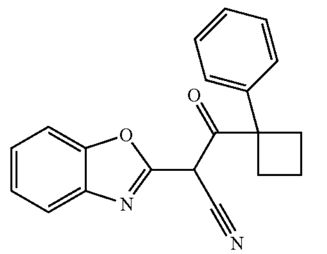 [SMILES: N#CC(C(=O)C1(c2ccccc2)CCC1)c1nc2ccccc2o1] | 2-(benzo[d]oxazol-2-yl)-3-oxo-3-(1-phenylcyclobutyl)propanenitrile |
| 15 | 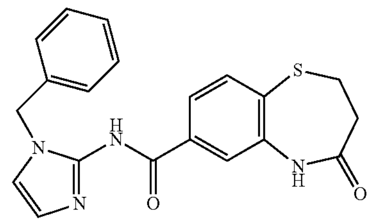 [SMILES: O=C1CCSc2ccc(C(=O)Nc3nccn3Cc3ccccc3)cc2N1] | N-(1-benzyl-1H-imidazol-2-yl)-4-oxo-2,3,4,5-tetrahydrobenzo[b][1,4]thiazepine-7-carboxamide |
| 16 | 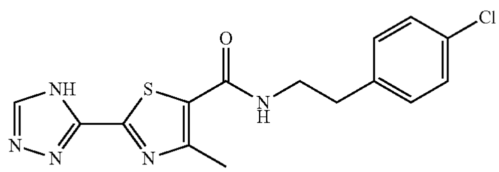 [SMILES: Cc1nc(-c2nnc[nH]2)sc1C(=O)NCCc1ccc(Cl)cc1] | N-(4-chlorophenethyl)-4-methyl-2-(4H-1,2,4-triazol-3-yl)thiazole-5-carboxamide |
| 17 | 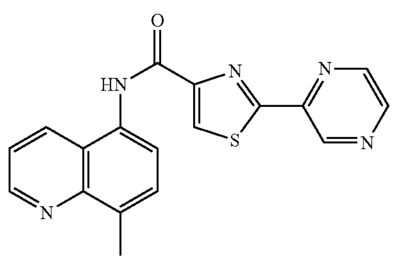 [SMILES: Cc1ccc(NC(=O)c2csc(-c3cnccn3)n2)c2cccnc12] | N-(8-methylquinolin-5-yl)-2-(pyrazin-2-yl)thiazole-4-carboxamide |
| 18 | 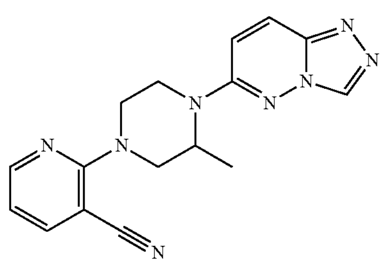 [SMILES: CC1CN(c2ncccc2C#N)CCN1c1ccc2nncn2n1] | 2-(4-([1,2,4]triazolo[4,3-b]pyridazin-6-yl)-3-methylpiperazin-1-yl)nicotinonitrile |
| 19 | 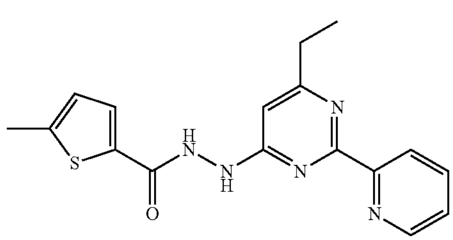 [SMILES: CCc1cc(NNC(=O)c2ccc(C)s2)nc(-c2ccccn2)n1] | N'-(6-ethyl-2-(pyridin-2-yl)pyrimidin-4-yl)-5-methylthiophene-2-carbohydrazide |

TABLE 2-continued

Examples of potential compounds

| No. | COMPOUND STRUCTURE | NAME |
|---|---|---|
| 20 | 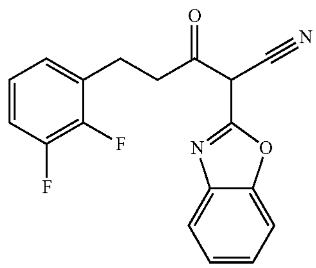 [SMILES: N#CC(C(=O)CCc1cccc(F)c1F)c1nc2ccccc2o1] | 2-(benzo[d]oxazol-2-yl)-5-(2,3-difluorophenyl)-3-oxopentanenitrile |
| 21 | 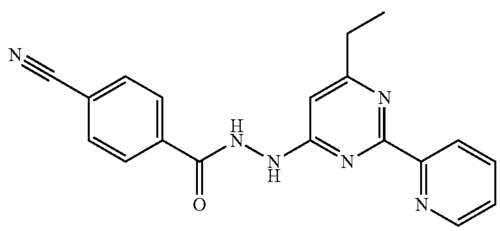 [SMILES: CCc1cc(NNC(=O)c2ccc(C#N)cc2)nc(-c2ccccn2)n1] | 4-cyano-N'-(6-ethyl-2-(pyridin-2-yl)pyrimidin-4-yl)benzohydrazide |
| 22 | 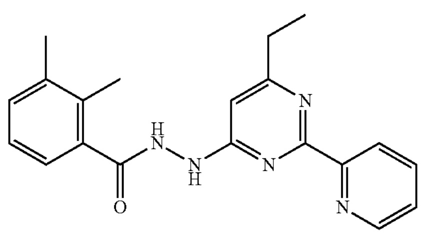 [SMILES: CCc1cc(NNC(=O)c2cccc(C)c2C)nc(-c2ccccn2)n1] | N'-(6-ethyl-2-(pyridin-2-yl)pyrimidin-4-yl)-2,3-dimethylbenzohydrazide |
| 23 | 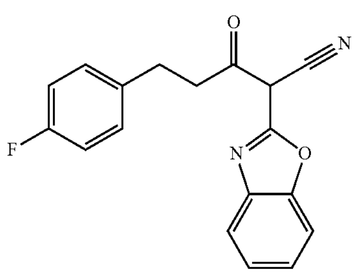 [SMILES: N#CC(C(=O)CCc1ccc(F)cc1)c1nc2ccccc2o1] | 2-(benzo[d]oxazol-2-yl)-5-(4-fluorophenyl)-3-oxopentanenitrile |
| 24 | 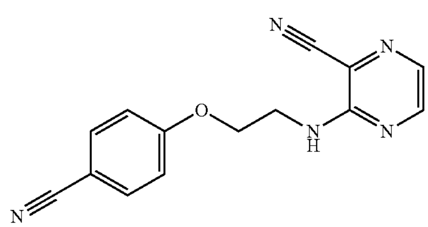 [SMILES: N#Cc1ccc(OCCNc2nccnc2C#N)cc1] | 3-((2-(4-cyanophenoxy)ethyl)amino)pyrazine-2-carbonitrile |
| 25 | 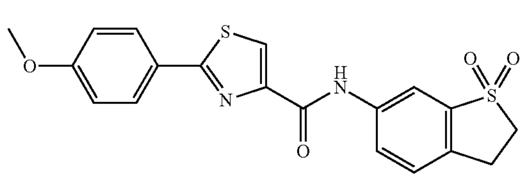 [SMILES: COc1ccc(-c2nc(C(=O)Nc3ccc4c(c3)S(=O)(=O)CC4)cs2)cc1] | N-(1,1-dioxido-2,3-dihydrobenzo[b]thiophen-6-yl)-2-(4-methoxyphenyl)thiazole-4-carboxamide |

| No. | COMPOUND STRUCTURE | NAME |
|---|---|---|
| 26 | 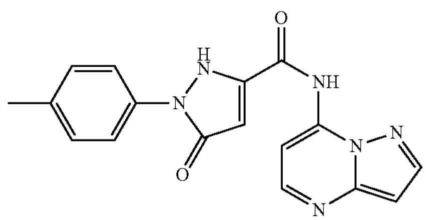 [SMILES: Cc1ccc(-n2[nH]c(C(=O)Nc3ccnc4ccnn34)cc2=O)cc1] | 5-oxo-N-(pyrazolo[1,5-a]pyrimidin-7-yl)-1-(p-tolyl)-2,5-dihydro-1H-pyrazole-3-carboxamide |
| 27 | 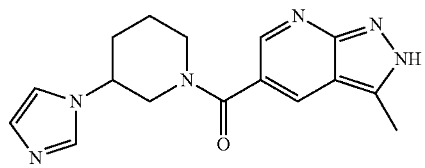 [SMILES: Cc1[nH]nc2ncc(C(=O)N3CCCC(n4ccnc4)C3)cc12] | (3-(1H-imidazol-1-yl)piperidin-1-yl)(3-methyl-2H-pyrazolo[3,4-b]pyridin-5-yl)methanone |
| 28 | 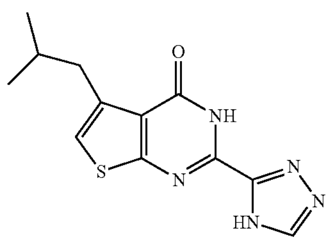 [SMILES: CC(C)Cc1csc2nc(-c3nnc[nH]3)[nH]c(=O)c12] | 5-isobutyl-2-(4H-1,2,4-triazol-3-yl)thieno[2,3-d]pyrimidin-4(3H)-one |
| 29 | 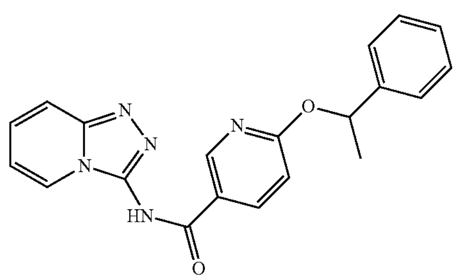 [SMILES: CC(Oc1ccc(C(=O)Nc2nnc3ccccn23)cn1)c1ccccc1] | N-([1,2,4]triazolo[4,3-a]pyridin-3-yl)-6-(1-phenylethoxy)nicotinamide |
| 30 | 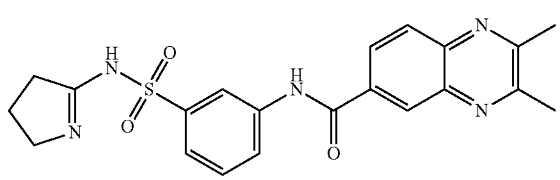 [SMILES: Cc1nc2ccc(C(=O)Nc3cccc(S(=O)(=O)NC4=NCCC4)c3)cc2nc1C] | N-(3-(N-(3,4-dihydro-2H-pyrrol-5-yl)sulfamoyl)phenyl)-2,3-dimethylquinoxaline-6-carboxamide |
| 31 | 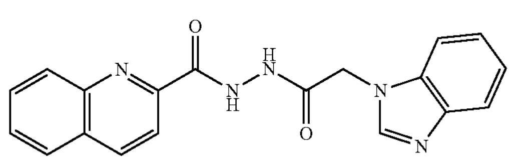 [SMILES: O=C(Cn1cnc2ccccc21)NNC(=O)c1ccc2ccccc2n1] | N'-(2-(1H-benzo[d]imidazol-1-yl)acetyl)quinoline-2-carbohydrazide |
| 32 | 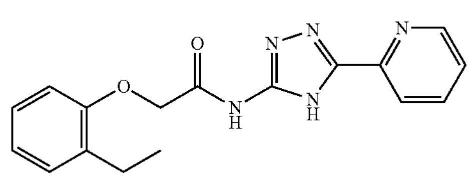 [SMILES: CCc1ccccc1OCC(=O)Nc1nnc(-c2ccccn2)[nH]1] | 2-(2-ethylphenoxy)-N-(5-(pyridin-2-yl)-4H-1,2,4-triazol-3-yl)acetamide |

TABLE 2-continued

| No. | COMPOUND STRUCTURE | NAME |
|---|---|---|
| 33 | 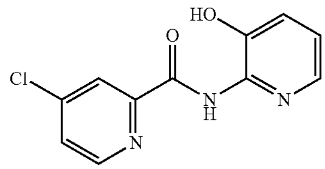 [SMILES: O=C(Nc1ncccc1O)c1cc(Cl)ccn1] | 4-chloro-N-(3-hydroxypyridin-2-yl)picolinamide |
| 34 | 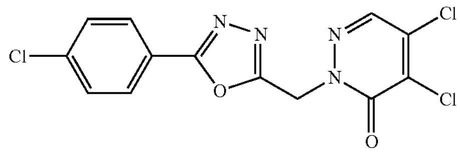 [SMILES: O=c1c(Cl)c(Cl)cnn1Cc1nnc(-c2ccc(Cl)cc2)o1] | 4,5-dichloro-2-((5-(4-chlorophenyl)-1,3,4-oxadiazol-2-yl)methyl)pyridazin-3(2H)-one |
| 35 | 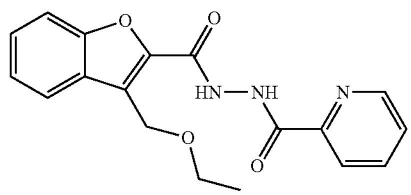 [SMILES: CCOCc1c(C(=O)NNC(=O)c2ccccn2)oc2ccccc12] | N'-(3-(ethoxymethyl)benzofuran-2-carbonyl)picolinohydrazide |
| 36 | 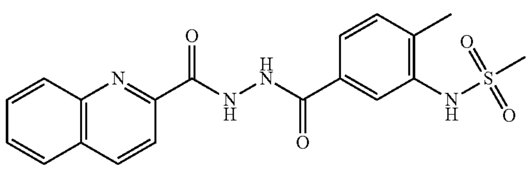 [SMILES: Cc1ccc(C(=O)NNC(=O)c2ccc3ccccc3n2)cc1NS(C)(=O)=O] | N-(2-methyl-5-(2-(quinoline-2-carbonyl)hydrazine-1-carbonyl)phenyl)methanesulfonamide |
| 37 | 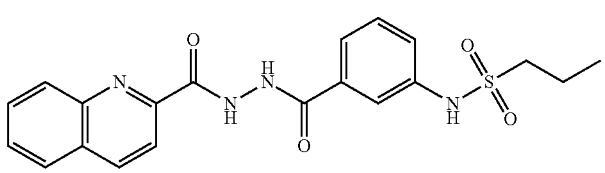 [SMILES: CCCS(=O)(=O)Nc1cccc(C(=O)NNC(=O)c2ccc3ccccc3n2)c1] | N-(3-(2-(quinoline-2-carbonyl)hydrazine-1-carbonyl)phenyl)propane-1-sulfonamide |
| 38 | 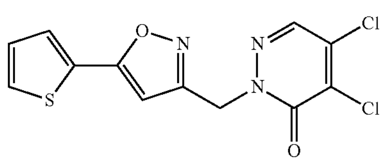 [SMILES: O=c1c(Cl)c(Cl)cnn1Cc1cc(-c2cccs2)on1] | 4,5-dichloro-2-((5-(thiophen-2-yl)isoxazol-3-yl)methyl)pyridazin-3(2H)-one |
| 39 | 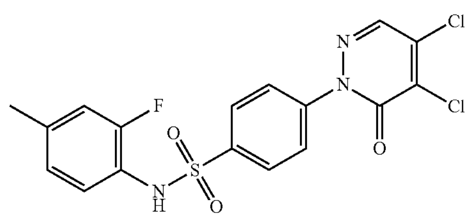 [SMILES: Cc1ccc(NS(=O)(=O)c2ccc(-n3ncc(Cl)c(Cl)c3=O)cc2)c(F)c1] | 4-(4,5-dichloro-6-oxopyridazin-1(6H)-yl)-N-(2-fluoro-4-methylphenyl)benzenesulfonamide |
| 40 | 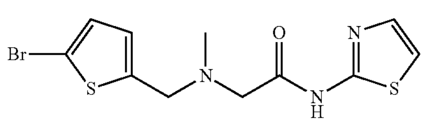 [SMILES: CN(CC(=O)Nc1nccs1)Cc1ccc(Br)s1] | 2-(((5-bromothiophen-2-yl)methyl)(methyl)amino)-N-(thiazol-2-yl)acetamide |

TABLE 2-continued

Examples of potential compounds

| No. | COMPOUND STRUCTURE | NAME |
|---|---|---|
| 41 | 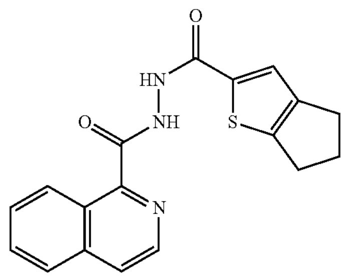 [SMILES: O=C(NNC(=O)c1nccc2ccccc12)c1cc2c(s1)CCC2] | N'-(5,6-dihydro-4H-cyclopenta[b]thiophene-2-carbonyl)isoquinoline-1-carbohydrazide |
| 42 | 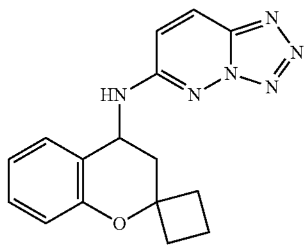 [SMILES: c1ccc2c(c1)OC1(CCC1)CC2Nc1ccc2nnnn2n1] | N-(spiro[chromane-2,1'-cyclobutan]-4-yl)tetrazolo[1,5-b]pyridazin-6-amine |
| 43 | 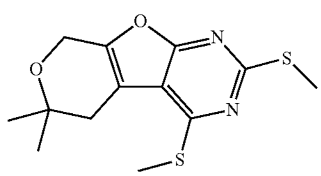 | 6,6-dimethyl-2,4-bis(methylthio)-5,8-dihydro-6H-pyrano[4',3':4,5]furo[2,3-d]pyrimidine |
| 44 | 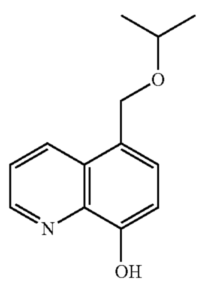 [SMILES: CC(C)OCc1ccc(O)c2ncccc12] | 5-(isopropoxymethyl)quinolin-8-ol |
| 45 | 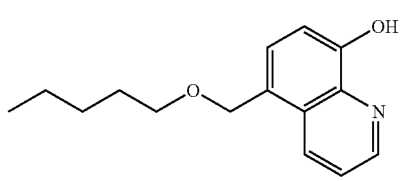 [SMILES: CCCCCOCc1ccc(O)c2ncccc12] | 5-((pentyloxy)methyl)quinolin-8-ol |
| 46 | 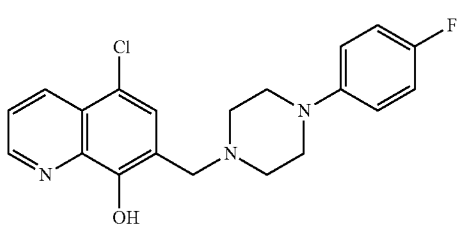 [SMILES: Oc1c(CN2CCN(c3ccc(F)cc3)CC2)cc(Cl)c2cccnc12] | 5-chloro-7-((4-(4-fluorophenyl)piperazin-1-yl)methyl)quinolin-8-ol |

TABLE 2-continued

Examples of potential compounds

| No. | COMPOUND STRUCTURE | NAME |
|---|---|---|
| 47 | 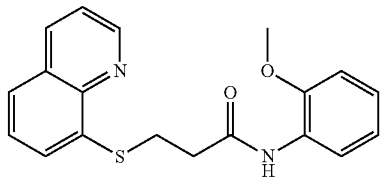 [SMILES: COc1ccccc1NC(=O)CCSc1cccc2cccnc12] | N-(2-methoxyphenyl)-3-(quinolin-8-ylthio)propanamide |
| 48 | 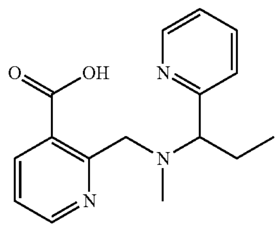 [SMILES: CCC(c1ccccn1)N(C)Cc1ncccc1C(=O)O] | 2-((methyl(1-(pyridin-2-yl)propyl)amino)methyl)nicotinic acid |
| 49 | 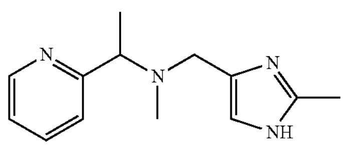 [SMILES: Cc1nc(CN(C)C(C)c2ccccn2)c[nH]1] | N-methyl-N-((2-methyl-1H-imidazol-4-yl)methyl)-1-(pyridin-2-yl)ethan-1-amine |
| 50 | 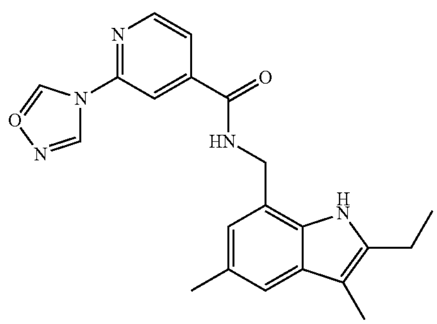 | N-((2-ethyl-3,5-dimethyl-1H-indol-7-yl)methyl)-2-(4H-1,2,4-triazol-4-yl)isonicotinamide |
| 51 | 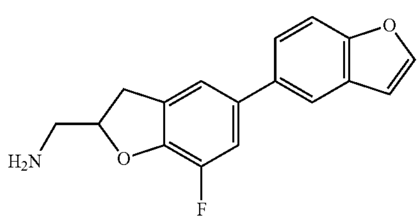 [SMILES: NCC1Cc2cc(-c3ccc4occc4c3)cc(F)c2O1] | (7-fluoro-2,3-dihydro-[5,5'-bibenzofuran]-2-yl)methanamine |
| 52 | 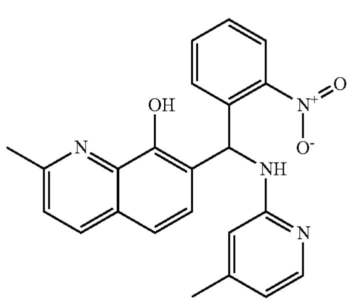 [SMILES: Cc1ccnc(NC(c2ccccc2[N+](=O)[O-])c2ccc3ccc(C)nc3c2O)c1] | 2-methyl-7-(((4-methylpyridin-2-yl)amino)(2-nitrophenyl)methyl)quinolin-8-ol |

TABLE 2-continued

Examples of potential compounds

| No. | COMPOUND STRUCTURE | NAME |
|---|---|---|
| 53 | 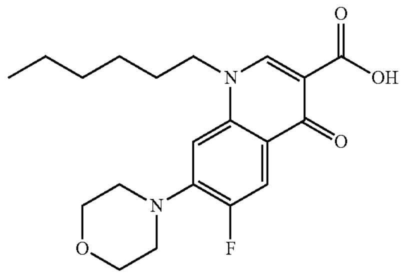 [SMILES: CCCCCCn1cc(C(=O)O)c(=O)c2cc(F)c(N3CCOCC3)cc21] | 6-fluoro-1-hexyl-7-morpholino-4-oxo-1,4-dihydroquinoline-3-carboxylic acid |
| 54 | 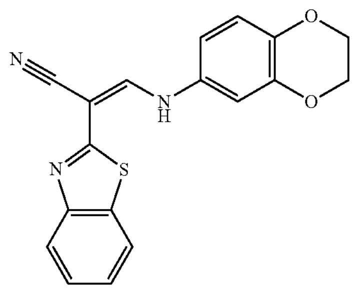 [SMILES: N#C/C(=C/Nc1ccc2c(c1)OCCO2)c1nc2ccccc2s1] | (Z)-2-(benzo[d]thiazol-2-yl)-3-((2,3-dihydrobenzo[b][1,4]dioxin-6-yl)amino)acrylonitrile |
| 55 | 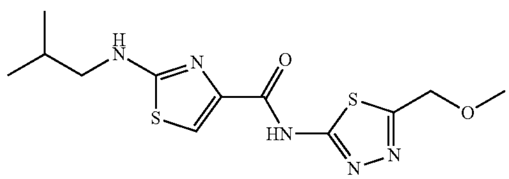 [SMILES: COCc1nnc(NC(=O)c2csc(NCC(C)C)n2)s1] | 2-(isobutylamino)-N-(5-(methoxymethyl)-1,3,4-thiadiazol-2-yl)thiazole-4-carboxamide |
| 56 | 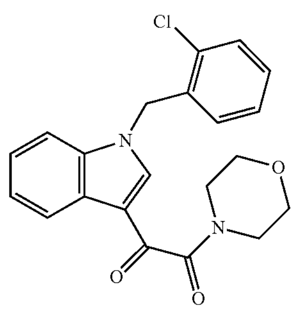 [SMILES: O=C(C(=O)N1CCOCC1)c1cn(Cc2ccccc2Cl)c2ccccc12] | 1-(1-(2-chlorobenzyl)-1H-indol-3-yl)-2-morpholinoethane-1,2-dione |
| 57 | 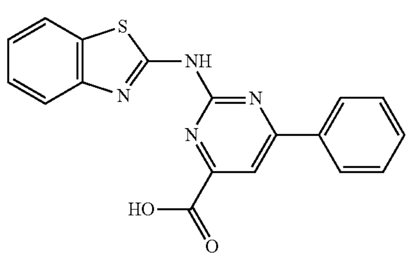 [SMILES: O=C(O)c1cc(-c2ccccc2)nc(Nc2nc3ccccc3s2)n1] | 2-(benzo[d]thiazol-2-ylamino)-6-phenylpyrimidine-4-carboxylic acid |
| 58 | 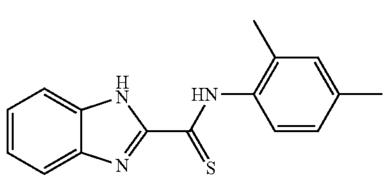 [SMILES: Cc1ccc(NC(=S)c2nc3ccccc3[nH]2)c(C)c1] | N-(2,4-dimethylphenyl)-1H-benzo[d]imidazole-2-carbothioamide |

TABLE 2-continued

Examples of potential compounds

| No. | COMPOUND STRUCTURE | NAME |
|---|---|---|
| 59 | 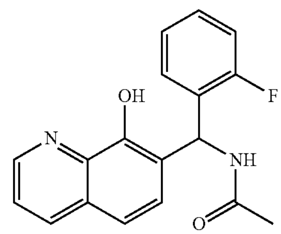 [SMILES: CC(=O)NC(c1ccccc1F)c1ccc2cccnc2c1O] | N-((2-fluorophenyl)(8-hydroxyquinolin-7-yl)methyl)acetamide |
| 60 | 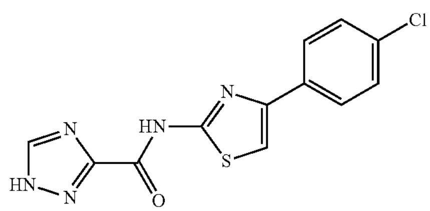 [SMILES: O=C(Nc1nc(-c2ccc(Cl)cc2)cs1)c1nc[nH]n1] | N-(4-(4-chlorophenyl)thiazol-2-yl)-1H-1,2,4-triazole-3-carboxamide |
| 61 | 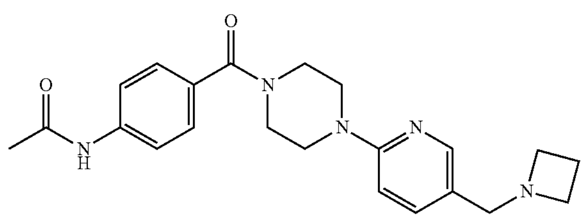 [SMILES: CC(=O)Nc1ccc(C(=O)N2CCN(c3ccc(CN4CCC4)cn3)CC2)cc1] | N-(4-(4-(5-(azetidin-1-ylmethyl)pyridin-2-yl)piperazine-1-carbonyl)phenyl)acetamide |
| 62 | 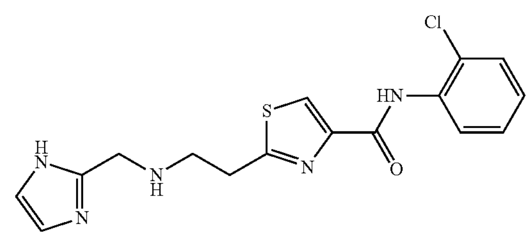 [SMILES: O=C(Nc1ccccc1Cl)c1csc(CCNCc2ncc[nH]2)n1] | 2-(2-(((1H-imidazol-2-yl)methyl)amino)ethyl)-N-(2-chlorophenyl)thiazole-4-carboxamide |
| 63 | 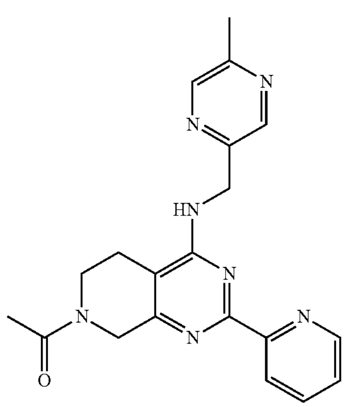 [SMILES: CC(=O)N1CCc2c(nc(-c3ccccn3)nc2NCc2cnc(C)cn2)C1] | 1-(4-(((5-methylpyrazin-2-yl)methyl)amino)-2-(pyridin-2-yl)-5,8-dihydropyrido[3,4-d]pyrimidin-7(6H)-yl)ethan-1-one |
| 64 | 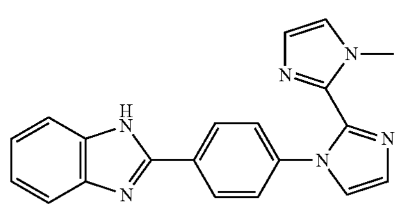 [SMILES: Cn1ccnc1-c1nccn1-c1ccc(-c2nc3ccccc3[nH]2)cc1] | 2-(4-(1'-methyl-1H,1'H-[2,2'-biimidazol]-1-yl)phenyl)-1H-benzo[d]imidazole |

TABLE 2-continued

Examples of potential compounds

| No. | COMPOUND STRUCTURE | NAME |
| --- | --- | --- |
| 65 | 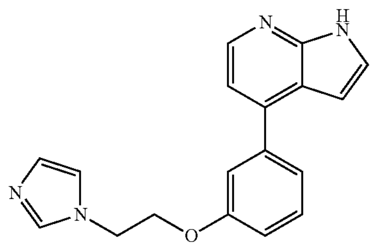 [SMILES: c1cc(OCCn2ccnc2)cc(-c2ccnc3[nH]ccc23)c1] | 4-(3-(2-(1H-imidazol-1-yl)ethoxy)phenyl)-1H-pyrrolo[2,3-b]pyridine |
| 66 | 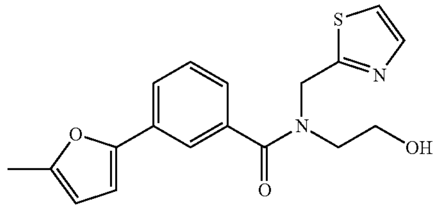 [SMILES: Cc1ccc(-c2cccc(C(=O)N(CCO)Cc3nccs3)c2)o1] | N-(2-hydroxyethyl)-3-(5-methylfuran-2-yl)-N-(thiazol-2-ylmethyl)benzamide |
| 67 | 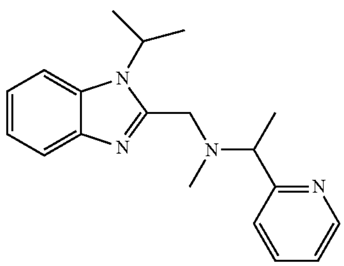 [SMILES: CC(c1ccccn1)N(C)Cc1nc2ccccc2n1C(C)C] | N-((1-isopropyl-1H-benzo[d]imidazol-2-yl)methyl)-N-methyl-1-(pyridin-2-yl)ethan-1-amine |
| 68 | 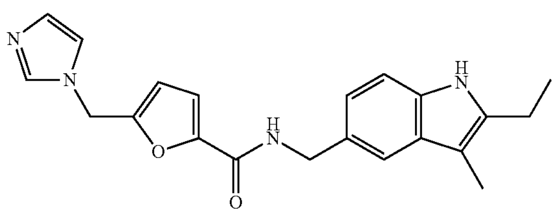 [SMILES: CCc1[nH]c2ccc(CNC(=O)c3ccc(Cn4ccnc4)o3)cc2c1C] | 5-((1H-imidazol-l-yl)methyl)-N-((2-ethyl-3-methyl-1H-indol-5-yl)methyl)furan-2-carboxamide |
| 69 | 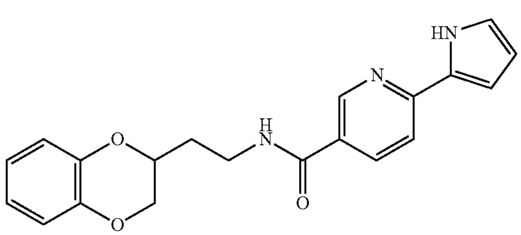 [SMILES: O=C(NCCC1COc2ccccc2O1)c1ccc(-c2ccc[nH]2)nc1] | N-(2-(2,3-dihydrobenzo[b][1,4]dioxin-2-yl)ethyl)-6-(1H-pyrrol-2-yl)nicotinamide |
| 70 | 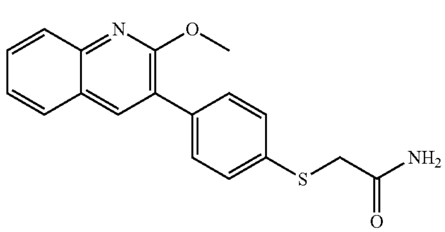 [SMILES: COc1nc2ccccc2cc1-c1ccc(SCC(N)=O)cc1] | 2-((4-(2-methoxyquinolin-3-yl)phenyl)thio)acetamide |

TABLE 2-continued

Examples of potential compounds

| No. | COMPOUND STRUCTURE | NAME |
| --- | --- | --- |
| 71 | 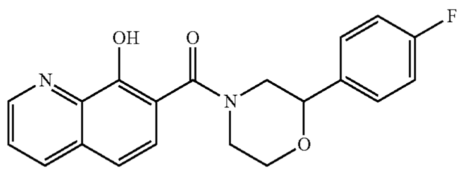 [SMILES: O=C(c1ccc2cccnc2c1O)N1CCOC(c2ccc(F)cc2)C1] | (2-(4-fluorophenyl)morpholino)(8-hydroxyquinolin-7-yl)methanone |
| 72 | 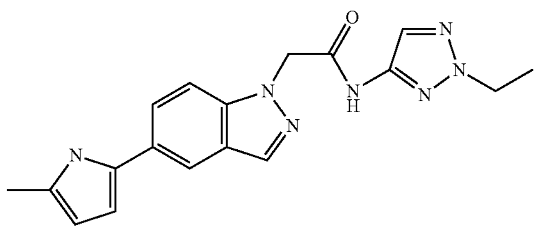 [SMILES: CCn1ncc(NC(=O)Cn2ncc3cc(-c4ccc(C)[nH]4)ccc32)n1] | N-(2-ethyl-2H-1,2,3-triazol-4-yl)-2-(5-(5-methylfuran-2-yl)-1H-indazol-1-yl)acetamide |
| 73 | 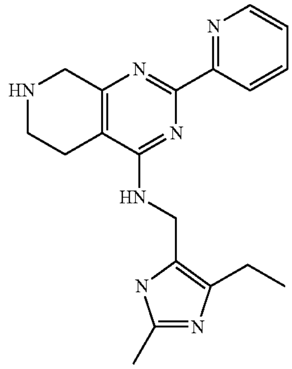 [SMILES: CCc1nc(C)[nH]c1CNc1nc(-c2ccccn2)nc2c1CCNC2] | N-((4-ethyl-2-methylthiazol-5-yl)methyl)-2-(pyridin-2-yl)-5,6,7,8-tetrahydropyrido[3,4-d]pyrimidin-4-amine |
| 74 | 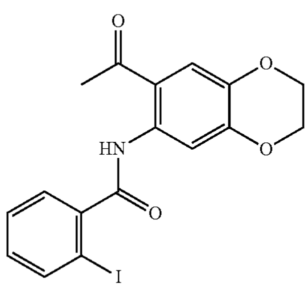 [SMILES: CC(=O)c1cc2c(cc1NC(=O)c1ccccc1I)OCCO2] | N-(7-acetyl-2,3-dihydrobenzo[b][1,4]dioxin-6-yl)-2-iodobenzamide |
| 75 | 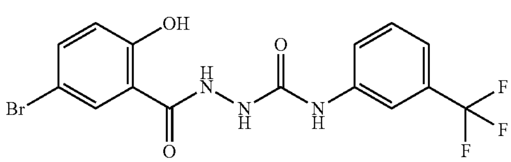 [SMILES: O=C(NNC(=O)c1cc(Br)ccc1O)Nc1cccc(C(F)(F)F)c1] | 2-(5-bromo-2-hydroxybenzoyl)-N-(3-(trifluoromethyl)phenyl)hydrazine-1-carbothioamide |
| 76 | 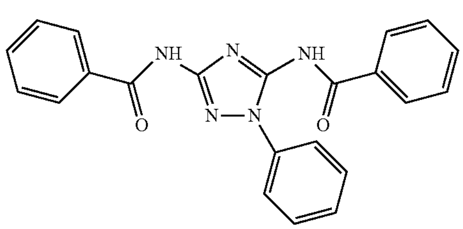 [SMILES: O=C(Nc1nc(NC(=O)c2ccccc2)n(-c2ccccc2)n1)c1ccccc1] | N,N'-(1-phenyl-1H-1,2,4-triazole-3,5-diyl)dibenzamide |

TABLE 2-continued

Examples of potential compounds

| No. | COMPOUND STRUCTURE | NAME |
|---|---|---|
| 77 | 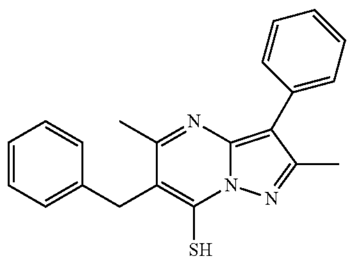 [SMILES: Cc1nc2c(-c3ccccc3)c(C)nn2c(S)c1Cc1ccccc1] | 6-benzyl-2,5-dimethyl-3-phenylpyrazolo[1,5-a]pyrimidine-7-thiol |
| 78 | 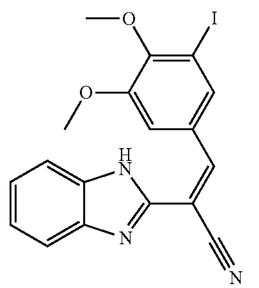 [SMILES: COc1cc(/C=C(/C#N)c2nc3ccccc3[nH]2)cc(I)c1OC] | (Z)-2-(1H-benzo[d]imidazol-2-yl)-3-(3-iodo-4,5-dimethoxyphenyl)acrylonitrile |
| 79 | 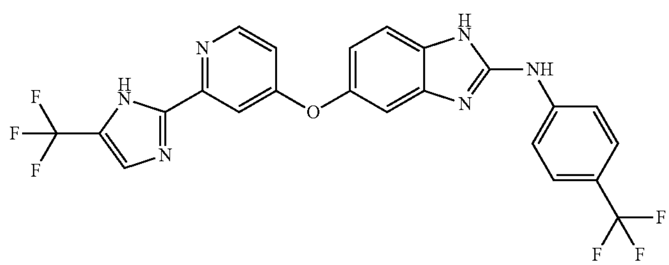 [SMILES: FC(F)(F)c1ccc(Nc2nc3cc(Oc4ccnc(-c5ncc(C(F)(F)F)[nH]5)c4)ccc3[nH]2)cc1] | 5-((2-(5-(trifluoromethyl)-1H-imidazol-2-yl)pyridin-4-yl)oxy)-N-(4-(trifluoromethyl)phenyl)-1H-benzo[d]imidazol-2-amine |
| 80 | 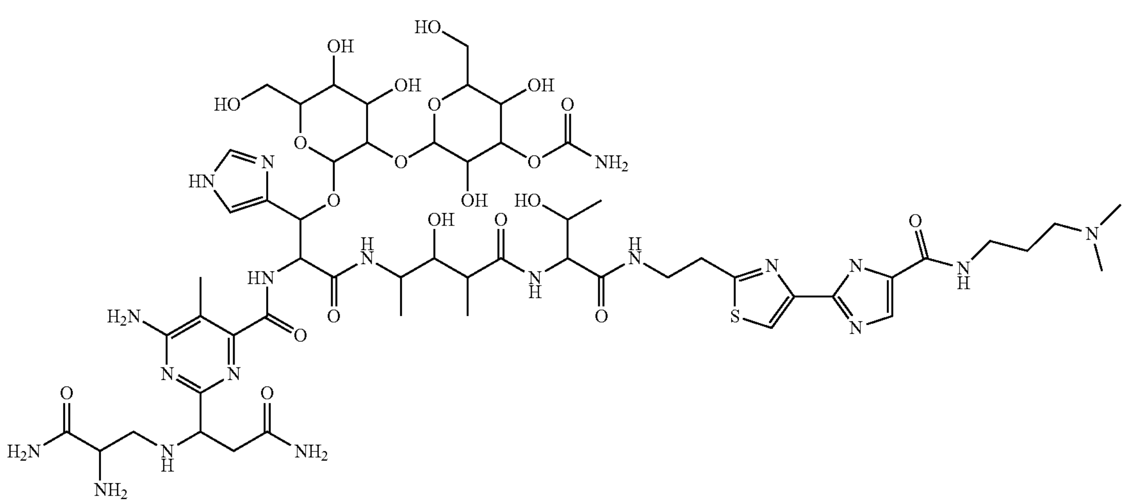 [SMILES: Cc1c(N)nc(C(CC(N)=O)NCC(N)C(N)=O)nc1C(=O)NC(C(=O)NC(C)C(O)C(C)C(=O)NC(C(=O)NCCc1nc(-c2ncc(C(=O)NCCCN(C)C)[nH]2)cs1)C(C)O)C(OC1OC(CO)C(O)C(O)C1OC1OC(CO)C(O)C(OC(N)=O)C1O)c1c[nH]cn1] | |

TABLE 2-continued

Examples of potential compounds

| No. | COMPOUND STRUCTURE | NAME |
|---|---|---|
| 81 | 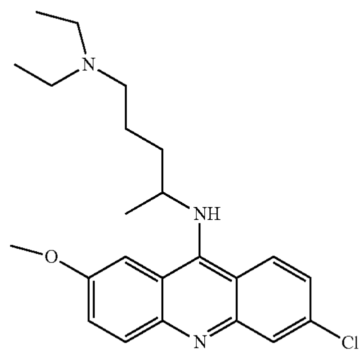 [SMILES: CCN(CC)CCCC(C)Nc1c2ccc(Cl)cc2nc2ccc(OC)cc12] | $N^4$-(6-chloro-2-methoxyacridin-9-yl)-$N^1,N^1$-diethylpentane-1,4-diamine |
| 82 | 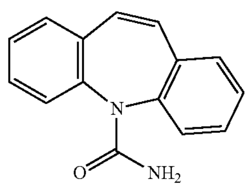 [SMILES: NC(=O)N1c2ccccc2C=Cc2ccccc21] | 5H-dibenzo[b,f]azepine-5-carboxamides |
| 83 | 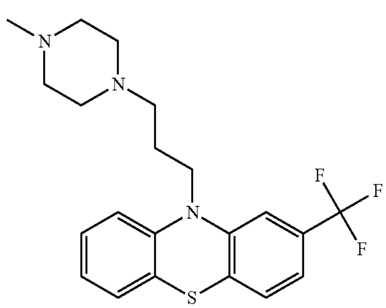 [SMILES: CN1CCN(CCCN2c3ccccc3Sc3ccc(C(F)(F)F)cc32)CC1] | 10-(3-(4-methylpiperazin-1-yl)propyl)-2-(trifluoromethyl)-10H-phenothiazine |
| 84 | 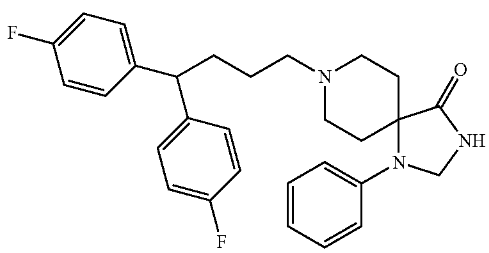 [SMILES: O=C1NCN(c2ccccc2)C12CCN(CCCC(c1ccc(F)cc1)c1ccc(F)cc1)CC2] | 8-(4,4-bis(4-fluorophenyl)butyl)-1-phenyl-1,3,8-triazaspiro[4.5]decan-4-one |
| 85 | 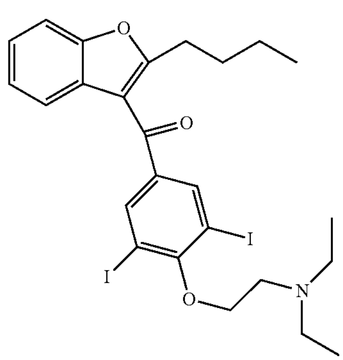 [SMILES: CCCCc1oc2ccccc2c1C(=O)c1cc(I)c(OCCN(CC)CC)c(I)c1] | (2-butylbenzofuran-3-yl)(4-(2-(diethylamino)ethoxy)-3,5-diiodophenyl)methanone |

TABLE 2-continued

Examples of potential compounds

| No. | COMPOUND STRUCTURE | NAME |
|---|---|---|
| 86 | 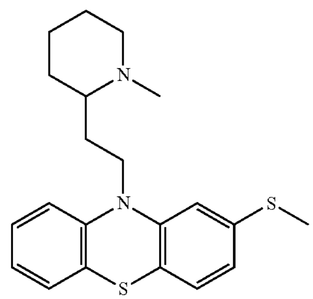 [SMILES: CSc1ccc2c(c1)N(CCC1CCCCN1C)c1ccccc1S2] | 10-(2-(1-methylpiperidin-2-yl)ethyl)-2-(methylthio)-10H-phenothiazine |
| 87 | 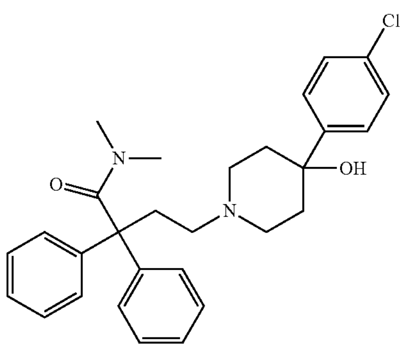 [SMILES: CN(C)C(=O)C(CCN1CCC(O)(c2ccc(Cl)cc2)CC1)(c1ccccc1)c1ccccc1] | 4-(4-(4-chlorophenyl)-4-hydroxypiperidin-1-yl)-N,N-dimethyl-2,2-diphenylbutanamide |
| 88 | 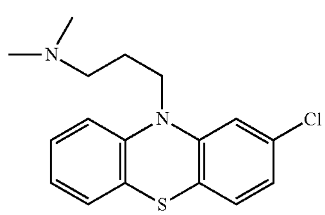 [SMILES: CN(C)CCCN1c2ccccc2Sc2ccc(Cl)cc21] | 3-(2-chloro-10H-phenothiazin-10-yl)-N,N-dimethylpropan-1-amine |
| 89 | 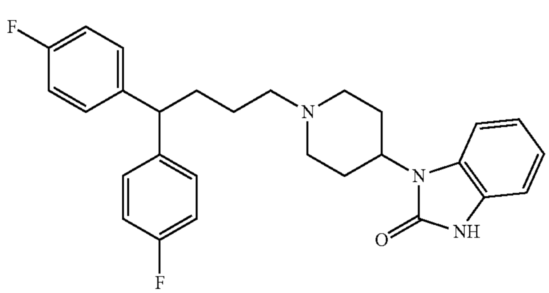 [SMILES: O=c1[nH]c2ccccc2n1C1CCN(CCCC(c2ccc(F)cc2)c2ccc(F)cc2)CC1] | 1-(1-(4,4-bis(4-fluorophenyl)butyl)piperidin-4-yl)-1,3-dihydro-2H-benzo[d]imidazol-2-one |
| 90 | 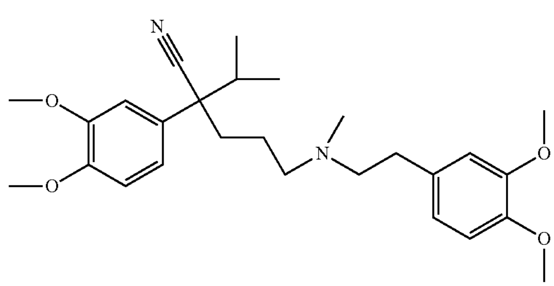 | 5-((3,4-dimethoxyphenethyl)(methyl)amino)-2-(3,4-dimethoxyphenyl)-2-isopropylpentanenitrile |

TABLE 2-continued

Examples of potential compounds

| No. | COMPOUND STRUCTURE | NAME |
|---|---|---|
| 91 | 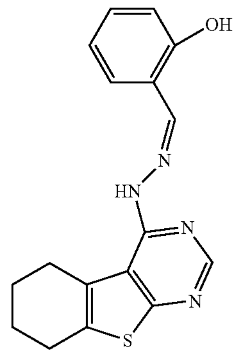 [SMILES: Oc1ccccc1/C=N\Nc1ncnc2sc3c(c12)CCCC3] | (Z)-2-((2-(5,6,7,8-tetrahydrobenzo[4,5]thieno[2,3-d]pyrimidin-4-yl)hydrazono)methyl)phenol |
| 92 | 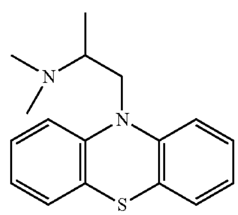 [SMILES: CC(CN1c2ccccc2Sc2ccccc21)N(C)C] | N,N-dimethyl-1-(10H-phenothiazin-10-yl)propan-2-amine |
| 93 | 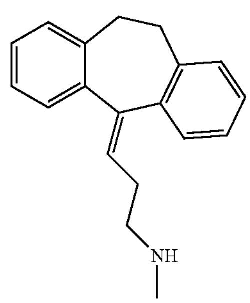 [SMILES: CNCCC=C1c2ccccc2CCc2ccccc21] | 3-(10,11-dihydro-5H-dibenzo[a,d][7]annulen-5-ylidene)-N-methylpropan-1-amine |
| 94 | 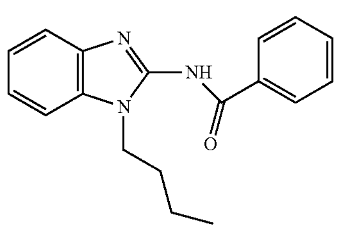 [SMILES: CCCCn1c(NC(=O)c2ccccc2)nc2ccccc21] | N-(1-butyl-1H-benzo[d]imidazol-2-yl)benzamide |
| 95 | 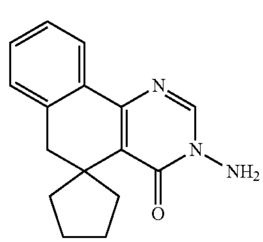 [SMILES: Nn1cnc2c(c1=O)C1(CCCC1)Cc1ccccc1-2] | 3-amino-3H-spiro[benzo[h]quinazoline-5,1'-cyclopentan]-4(6H)-one |

TABLE 2-continued

Examples of potential compounds

| No. | COMPOUND STRUCTURE | NAME |
|---|---|---|
| 96 | 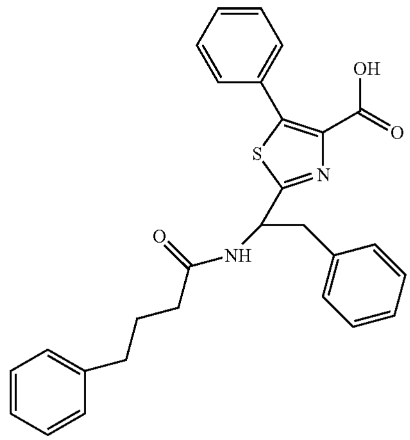 [SMILES: O=C(CCCc1ccccc1)NC(Cc1ccccc1)c1nc(C(=O)O)c(-c2ccccc2)s1] | 5-phenyl-2-(2-phenyl-1-(4-phenylbutanamido)ethyl)thiazole-4-carboxylic acid |
| 97 | 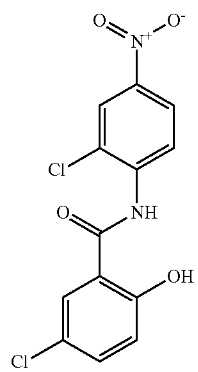 [SMILES: O=C(Nc1ccc([N+](=O)[O-])cc1Cl)c1cc(Cl)ccc1O] | 5-chloro-N-(2-chloro-4-nitrophenyl)-2-hydroxybenzamide |
| 98 | 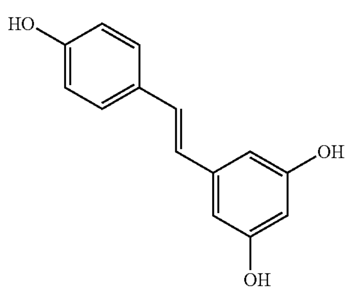 [SMILES: Oc1ccc(/C=C/c2cc(O)cc(O)c2)cc1] | (E)-5-(4-hydroxystyryl)benzene-1,3-diol |
| 99 | 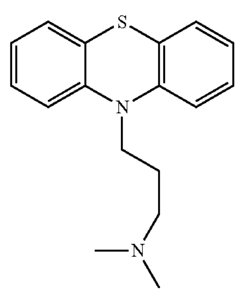 [SMILES: CN(C)CCCN1c2ccccc2Sc2ccccc21] | N,N-dimethyl-3-(10H-phenothiazin-10-yl)propan-1-amine |

TABLE 2-continued
Examples of potential compounds
| No. | COMPOUND STRUCTURE | NAME |
|---|---|---|
| 100 | 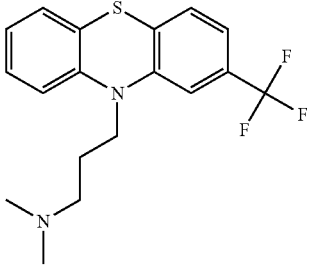 [SMILES: CN(C)CCCN1c2ccccc2Sc2ccc(C(F)(F)F)cc21] | N,N-dimethyl-3-(2-(trifluoromethyl)-10H-phenothiazin-10-yl)propan-1-aminen |
| 101 | 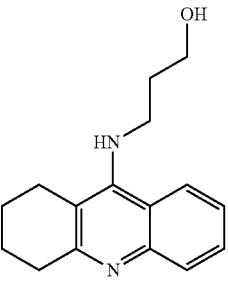 [SMILES: OCCCNc1c2c(nc3ccccc13)CCCC2] | 3-((1,2,3,4-tetrahydroacridin-9-yl)amino)propan-1-olo |
| 102 | 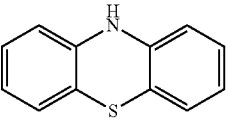 [SMILES: c1ccc2c(c1)Nc1ccccc1S2] | 10H-phenothiazine |
| 103 | 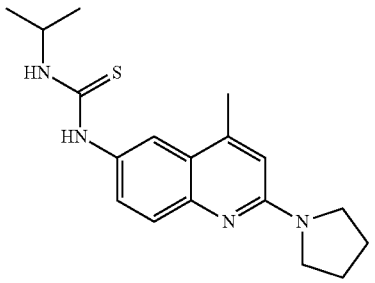 [SMILES: Cc1cc(N2CCCC2)nc2ccc(NC(=S)NC(C)C)cc12] | 1-isopropyl-3-(4-methyl-2-(pyrrolidin-1-yl)quinolin-6-yl)thiourea |
| 104 | 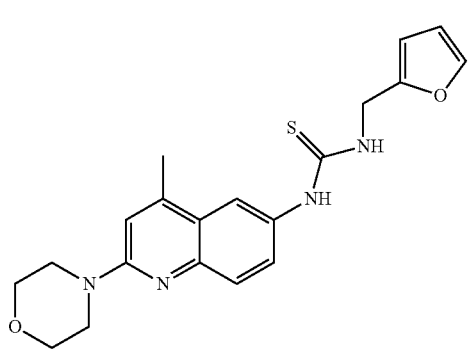 [SMILES: Cc1cc(N2CCOCC2)nc2ccc(NC(=S)NCc3ccco3)cc12] | 1-(furan-2-ylmethyl)-3-(4-methyl-2-morpholinoquinolin-6-yl)thiourea |
| 105 | 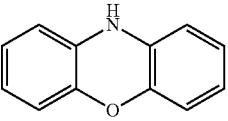 [SMILES: c1ccc2c(c1)Nc1ccccc1O2] | 10H-phenoxazine |

TABLE 2-continued

Examples of potential compounds

| No. | COMPOUND STRUCTURE | NAME |
|---|---|---|
| 106 | 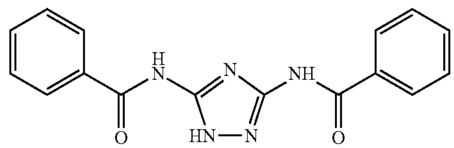 [SMILES: O=C(Nc1n[nH]c(NC(=O)c2ccccc2)n1)c1ccccc1] | N,N'-(1H-1,2,4-triazole-3,5-diyl)dibenzamide |
| 107 | 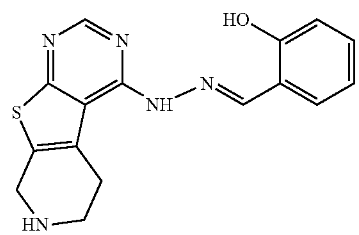 [SMILES: Oc1ccccc1/C=N/Nc1ncnc2sc3c(c12)CCNC3] | (E)-2-((2-(5,6,7,8-tetrahydropyrido[4',3':4,5]thieno[2,3-d]pyrimidin-4-yl)hydrazono)methyl)phenol |
| 108 | 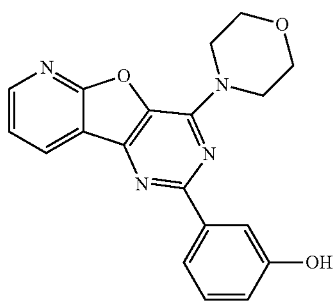 [SMILES: Oc1cccc(-c2nc(N3CCOCC3)c3oc4ncccc4c3n2)c1] | 3-(4-morpholinopyrido[3',2':4,5]furo[3,2-d]pyrimidin-2-yl)phenol |
| 109 | 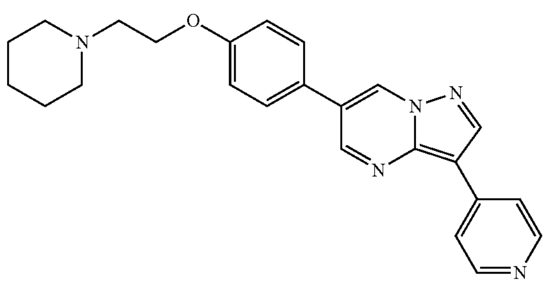 [SMILES: c1cc(-c2cnn3cc(-c4ccc(OCCN5CCCCC5)cc4)cnc23)ccn1] | 6-(4-(2-(piperidin-1-yl)ethoxy)phenyl)-3-(pyridin-4-yl)pyrazolo[1,5-a]pyrimidine |
| 110 | 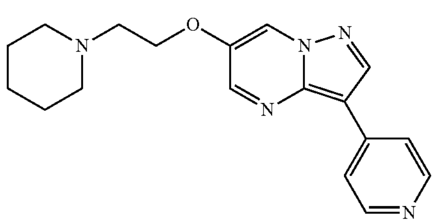 [SMILES: c1cc(-c2cnn3cc(OCCN4CCCCC4)cnc23)ccn1] | 6-(2-(piperidin-1-yl)ethoxy)-3-(pyridin-4-yl)pyrazolo[1,5-a]pyrimidine |
| 111 | 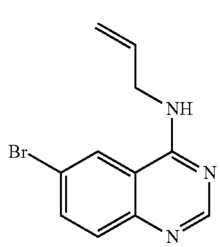 | N-allyl-6-bromoquinazolin-4-amine |

TABLE 2-continued

Examples of potential compounds

| No. | COMPOUND STRUCTURE | NAME |
|---|---|---|
| 112 | 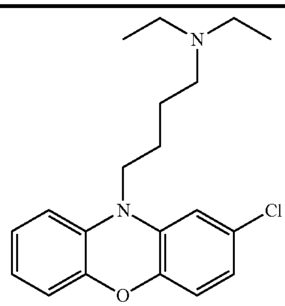 | 4-(2-chloro-10H-phenoxazin-10-yl)-N,N-diethylbutan-1-amine |
| 113 | 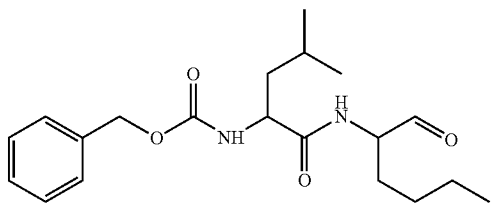 [SMILES: CCCCC(C=O)NC(=O)C(CC(C)C)NC(=O)OCc1ccccc1] | benzyl (4-methyl-1-oxo-1-((1-oxohexan-2-yl)amino)pentan-2-yl)carbamate |
| 114 | 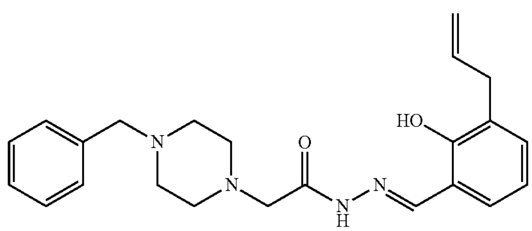 [SMILES: C=CCc1cccc(/C=N/NC(=O)CN2CCN(Cc3ccccc3)CC2)c1O] | 2-(4-benzylpiperazin-1-yl)-N-[(2-hydroxy-3-prop-2-enyl-phenyl)methylideneamino]acetamide |

TABLE 3

Amino Acid Sequence of Human Parkin Ligase (SEQ ID NO: 1)

MIVFVRRNSSHGFPVEVDSDTSIFQLKEVVAKRQGVPADQLRVIFAGKEL

RNDWTVQNCDLDQQSIVHIVQRPWRKGQEMNATGGDDPRNAAGGCEREPQ

SLTRVDLSSSVLPGDSVGLAVILHTDSRKDSPPAGSPAGRSIYNSFYVYC

KGPCQRVQPGKLRVQCSTCRQATLTLTQGPSCWDDVLIPNRMSGECQSPH

CPGTSAEFFFKCGAHPTSDKETSVALHLIATNSRNITCITCTDVRSPVLV

FQCNSRHVICLDCFHLYCVTRLNDRQFVHDPQLGYSLPCVAGCPNSLIKE

LHHFRILGEEQYNRYQQYGAEECVLQMGGVLCPRPGCGAGLLPEPDQRKV

TCEGGNGLGCGFAFCRECKEAYHEGECSAVFEASGTTTQAYRVDERAAEQ

ARWEAASKETIKKTTKPCPRCHVPVEKNGGCMHMKCPQPQCRLEWCWNCG

CEWNRVCMGDHWFDV

The present invention also relates to the pharmaceutical formulations for activating Parkin ligase in a subject comprising an effective does of an agent that disrupts at least one Parkin ligase zinc finger, wherein the agent or the compound that can coordinate a zinc ion, or the agent or the compound that can react with the thiol group in a cysteine.

Further embodiments of the present invention are directed to the pharmaceutical formulations further comprising a pharmaceutically acceptable excipient or adjuvant.

The methods of the present invention include any clinically-acceptable route of administration of the composition to the subject. In various aspects, the route of administration is systemic, e.g., oral or by injection. The agents or compounds, or pharmaceutically acceptable salts or derivatives thereof, are administered orally, nasally, transdermally, pulmonary, inhalationally, buccally, sublingually, intraperintoneally, subcutaneously, intramuscularly, intravenously, rectally, intrapleurally, intrathecally, intraportally, and parenterally. Alternatively or in addition, the route of administration is local, e.g., topical, intra-tumor and peri-tumor. In some embodiments, the compound is administered orally.

In other embodiments the agents disclosed herein are administered by the intravenous route. In further embodiments, the parenteral administration may be provided in a bolus or by infusion.

The manner in which the composition is administered is dependent, in part, upon the cause and/or location. One skilled in the art will recognize the advantages of certain routes of administration.

The method includes administering an effective amount of the agent or compound (or composition comprising the agent or compound) to achieve a desired biological response, e.g., an amount effective to alleviate, ameliorate, or prevent, in whole or in part, a symptom of a condition to be treated, e.g., oncology and neurology disorders.

In various aspects, the amount of the compound of any one of structural formulas shown in Table 1 and or Table 2, or salt or ester thereof administered is about 0.001 mg/kg to about 100 mg/kg body weight (e.g., about 0.01 mg/kg to about 10 mg/kg or about 0.1 mg/kg to about 5 mg/kg).

The concentration of a disclosed compound in a pharmaceutically acceptable mixture will vary depending on several factors, including the dosage of the compound to be administered, the pharmacokinetic characteristics of the compound(s) employed, and the route of administration. The agent may be administered in a single dose or in repeat doses. The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. Treatments may be administered daily or more frequently depending upon a number of factors, including the overall health of a patient, and the formulation and route of administration of the selected compound(s). An ordinarily skilled physician or veterinarian can readily determine and prescribe the effective amount of the drug required to prevent, counter or arrest the progress of the condition.

The compound or composition of the invention may be manufactured and/or administered in single or multiple unit dose forms.

Further embodiments of the present invention relate to the composition comprising the compound of any one of structural formulas shown in Table 1, and or Table 2 and a pharmaceutically-acceptable carrier, e.g., a pharmaceutically-acceptable excipient, carrier, binder, and/or diluent.

Techniques for formulation and administration of the disclosed compounds of the invention can be found in *Remington: the Science and Practice of Pharmacy,* 19th edition, Mack Publishing Co., Easton, Pa. (1995).

In other embodiments, the compounds described herein, and the pharmaceutically acceptable salts, solvates, hydrates, and prodrugs thereof, are used in pharmaceutical preparations in combination with a pharmaceutically acceptable carrier or diluent. Suitable pharmaceutically acceptable carriers include inert solid fillers or diluents and sterile aqueous or organic solutions. Optionally, the composition comprises one or more additional therapeutic agents. The compounds will be present in such pharmaceutical compositions in amounts sufficient to provide the desired dosage amount in the range described herein.

In certain embodiments, the compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

In certain embodiments, pharmaceutical compositions of the present invention comprise one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tableting processes.

Additional embodiments relate to the pharmaceutical formulations wherein the formulation is selected from the group consisting of a solid, powder, liquid and a gel.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, tablet, and/or capsule). In certain of such embodiments, a solid pharmaceutical composition comprising one or more ingredients known in the art, including, but not limited to, starches, sugars, diluents, granulating agents, lubricants, binders, and disintegrating agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80 and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers.

In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more agents and pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppository or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more compounds of the present invention are formulated as a prodrug. In certain embodiments, upon in vivo administration, a prodrug is chemically converted to the biologically, pharmaceutically or therapeutically more active form. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Having now generally described the invention, the same will be more readily understood through reference to the following examples, which are provided by way of illustration and are not intended to be limiting of the present invention.

EXAMPLES

Example 1: Identification of Parkin Activators

Assay Principle:

The assay based on the irreversible reaction of an Activity-Based Probe (ABP) with the active site cysteine in the enzyme. ABP consists of a ubiquitin moiety with an epitope tag (e.g. HA tag) at the N-terminus, and a reactive group at the C-terminus. The activity of Parkin-RBR (w/o the R0 inhibitory domain) is significantly higher than the activity of Parkin-R0RBR or the activity of full-length Parkin. The covalent attachment of ABP to Parkin can be monitored by Time Resolved Fluorescence Resonance Energy Transfer (TR-FRET)

Parkin-R0RBR, full-length Parkin→low TR-FRET signal (negative control)

Parkin RBR→high TR-FRET signal (positive control)

Compounds increasing the activity of Parkin-R0RBR or the activity of full-length—Parkin can be identified by an increase in TR-FRET signal.

Strategy: use of N-terminal His-SUMO tagged constructs of Parkin-R0RBR, full-length Parkin and Parkin-RBR. (from Evotec Slides; Based on Riley et al. 2013. *Nat Commun*. 4:1982 & on information provided by E3x Bio; grant Application)

Constructs:

Full-length Parkin (1-465), R0RBR (141-465) and RBR (238-465) expression with N-terminal $His_6$-SUMO-tag (can potentially be removed during purification using SENP1 protease) in *E. coli* as described by Riley et al.

N-terminal $His_6$-tag enabling TR-FRET-assay→use of the purified protein that still have the N-terminal $His_6$-SUMO-tags on.

Small scale tests are conducted for all constructs to evaluate which construct, full-length Parkin or R0RBR, give better yield to facilitate an HTS-assay.

Phase 1: Protein Production

Initiate gene synthesis through third party for full-length Parkin with N-terminal $His_6$-SUMO, $His_6$-SUMO-R0RBR and $His_6$-SUMO-RBR, codon-optimized for expression in *E. coli* and subcloning into a suitable expression vector Small scale test expression evaluated by Western Blotting to estimate the yield of soluble protein Transform the RBR construct as well as either the full-length Parkin construct or the R0RBR construct into BL21 (DE3) and express as outlined in Riley et al., in the scale of 6-24 L (depending on outcome of small scale test expression)

Purification of ~10 mg of the RBR construct as well as either the full-length Parkin construct or the R0RBR construct as described by Riley et al. *, i.e. IMAC, MonoQ and size exclusion.

Phase 2: Assay Development

Goal: Set-up robust primary screening assays in 1,536-well assay plate format

Establish assays in 384-well format with a reasonable dynamic range (e.g. using Parkin +/− the R0 inhibitory domain)

Optimize assay (e.g. in terms of concentrations of assay components, buffer, additives, order of addition of reagents, and incubation temperature)

Run time course experiments to define optimal incubation times

Demonstrate assay robustness (goal: Z'>0.5)

Demonstrate readout stability

Test DMSO tolerance

Demonstrate specificity of the assay signal obtained using the Parkin RBR domain (w/o the R0 inhibitory domain) by titration of Ub (competing with ABP)

Transfer assay from 384- to final 1,536-well screening plate format; adapt the assay to the EVOscreen™ Mark III HTS platform If necessary, fine-tune the assay conditions in order to optimize assay robustness in this high density plate format (goal: Z'>0.5) and to demonstrate assay suitability for high-throughput screening (HTS)

Confirm stability of assay reagents under screening conditions over time

Demonstrate plate-to-plate and day-to-day assay robustness

Estimate and procure the amounts of all assay reagents required for screening and hit profiling.

Phase 3: Screening

Marker Library Screen (MLS):

Pre-screening of a diverse marker library of approximately 2.5 k representative lead-like compounds against the primary screening assay at two concentrations in triplicate Statistical analysis of the MLS and hit definition using the 3-sigma-method (plate-based, based on the scatter of compound-free DMSO wells)

Selection of the optimal compound concentration for primary screening

Primary Screen (PS):

Screening of approximately 75,000 lead-like compounds against the primary screening assay at one uniform compound concentration (n=1); re-screening of compound plates that do not meet an agreed re-screen criterion (e.g. Z'>0.5)

Hit definition for the primary screen using the 3-sigma-method (plate-based, based on the scatter of compound-free DMSO wells)

Statistical analysis of the primary screen→Primary Hit Compounds (Parkin activators)

Hit Confirmation (HC):

Selection of a set of up to approximately 750 primary hits for Hit Confirmation

Cherry picking of the selected compounds and reformatting for testing

Retesting of the selected cpds against the primary screening assay at the compound screening concentration (n=3)

Statistical analysis of the Hit Confirmation campaign→Identification of confirmed small molecule Parkin activators.

Phase 4: HitProfiling (HP):

Selection of a set of up to approximately 250 confirmed hit compounds for Hit Profiling Cherry picking of the selected compounds and reformatting for concentration-response testing Concentration-response testing as 11-point compound dilution series against the primary screening assay (n=2)

Automated data fitting of the concentration response curves and calculation of the resulting IC50 values LC/MS inspection of the hit compounds to confirm compound identity and purity Structure-activity relationship analysis (SAR) of the active hit compounds Confirmed & profiled small molecule Parkin activators.

Example 2: Activity-Based Probe Assay Using an Ubiquitin Vinyl Sulfone Probe A Ubiquitin vinyl sulfone probe can be used that irreversibly binds to the active site cysteine of Parkin ligase. Covalent attachment of the probe to the Parkin can be monitored by TR-FRET. Candidate activator compounds can be identified by increasing the activity of Parkin ligase due to an increase in TR-FRET signal. Screening for activating compounds can be distinguished from the controls as follows:

100% activation signal=Heat activated Parkin+100 nM control activator in DMSO. 0% activation signal=Heat activated Parkin+DMSO only. Parkin activators can be identified by an increase of the 0% activation signal TR-FRET signal.

Assay Conditions:
Materials:
Assay Plate: White 384 well plate (Corning 3572)
Enzyme: Parkin-His tagged 203 μM (10.5 mg/ml)
Probe: Ubiquitin vinyl-sulfone (HA-Ub-VS Boston Biochem U-212)
DMSO: DMSO (Sigma cat #D4540-100ML)
Reaction Buffer: 50 mM HEPES (pH 8.5), 150 mM NaCl, 0.01% Tween 20, 0.1% BSA
Detection Buffer: 50 mM HEPES (pH 8.5), 150 mM NaCl, 0.01% Tween 20, 0.1% BSA, 800 mM KF
Detection Reagent A: 2.6 nM Anti-6HIS-Eu cryptate and 40 nM Anti-HA-XL665 in detection buffer
Eu cryptate: Anti-6HIS-Eu cryptate (CisBio 61HISKLA)
XL665: Anti-HA-XL665 (CisBio 610HAXLA)
Enzyme Reaction (15 Min Pre Incubation Parkin with Activator Only)
Parkin: 40 nM
HA-Ub-VS Probe: 70 nM
Activator/DMSO: 2× Activator candidates/2% DMSO
Reaction time: 60 minutes
Temperature: 22° C.
Total volume: 10 μl reaction
Detection Reaction
Take 10 μl of Enzyme Reaction above and add 10 μl detection Reagent A under the following conditions:
Reaction time: 60 minutes
Temperature: 22° C.
Total volume: 20 μl Assay Procedure:
1) Heat activate Parkin in Enzyme reaction buffer (500 μl/1.5 ml tube: Eppendorf Thermomixer 5 minutes, 400 rpm at 58° C. and put on ice until needed).
2) Load assay plate wells with 4.8 μl 84.5 nM Parkin in reaction buffer by use of Bravo.
3) Deliver 0.2 μl 200× activator candidates in DMSO by use of HP D-300 compound dispenser. Highest 200× concentration=20 μm and then twofold dilutions.
4) Spin 1000 rpm, 2 minutes, at room temp.
5) Incubate plate for 15 minutes at room temp.
6) Add 5 μl 140 nM HA-Ub-VS Probe in reaction buffer by use of Bravo.
7) Spin 1000 rpm, 2 minutes, at room temp.
8) Incubate plate for 60 minutes at room temp.
9) Add 10 μl 2.6 nM Anti-6HIS-Eu cryptate and 40 nM Anti-HA-XL665 in detection buffer.
10) Spin 1000 rpm, 2 minutes, at room temp.
11) Incubate plate for 60 minutes at room temp.
12) Read plates on Perkin Elmer Envision instrument.

Data Analysis: The Data can be read in CSV files. There are two tables in those CSV files, which are the values of 655 nm (channel 1) and 615 nm (channel 2) wavelengths respectively. The data is converted to an HTRF Ratio=(Channel 1/Channel 2)*10,000

The average of all the 0 uM controls (DMSO only)= BKGD (Background—0% activation). Subtract BKGD from each HTRF Ratio value=HTRF−BKGD. The average of all the 100 uM 100 nM control activator in DMSO controls=Max (100% activation). The following equation is then used to calculate % Activation for each well/candidate as follows: % Activation=(HTRF−BKGD/Max)*100.

The % Activation of compound titration can then be used to find activation EC50 or highest % Activation if less than 75% activation is seen for the candidate compound.

Example 3: Activity-Based Probe Assay with Candidate Electrophile and Chelator Compounds The Activity-Based Probe Assay was performed as in Example 2 above with various compounds in Table 1 and/or Table 2. At least two compounds indicated increasing Parkin activity with the activity-based probe Ubiquitin-vinyl sulfone. As demonstrated in FIG. 1, compound N,N'-(1-phenyl-1H-1,2,4-triazole-3,5-diyl)dibenzamide, a chelator compound (AH001) increases the Parkin Ligase reaction with the Activity-based Ubituitin vinyl sulfone probe.

Figure 2:
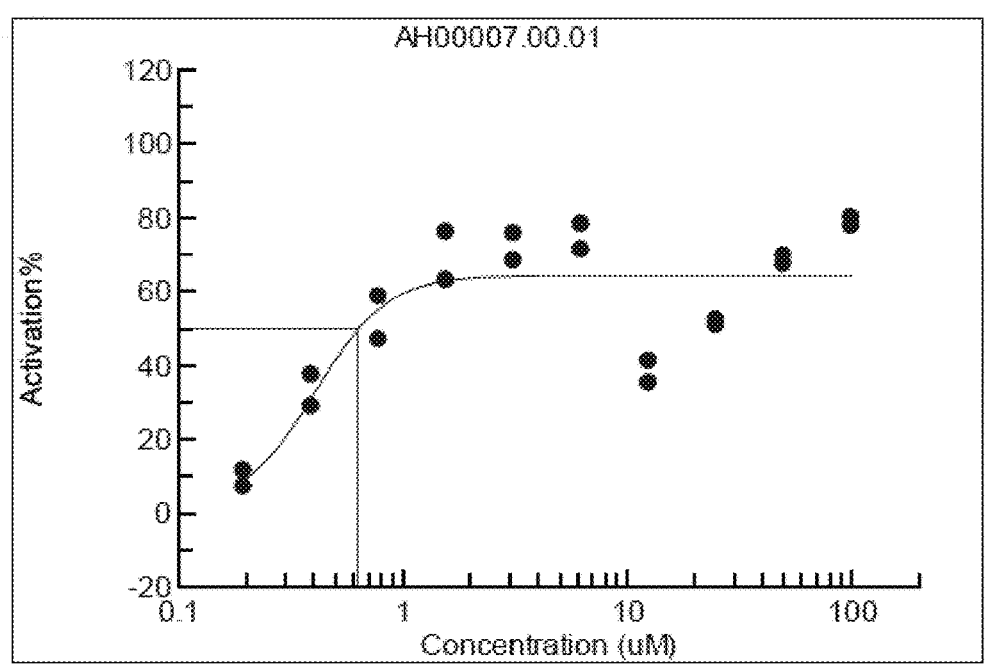
FIG. 2 indicates that 6-benzyl-2,5-dimethyl-3-phenylpyrazolo[1,5-a]pyrimidine-7-thiol, an electrophile and chelator compound (identified as AH007 or compound 77 in Table 2) increases the Parkin Ligase reaction with the Activity-based Ubiquitin vinyl sulfone probe.

Similarly, as indicated in FIG. 2, 6-benzyl-2,5-dimethyl-3-phenylpyrazolo[1,5-a]pyrimidine-7-thiol, an electrophile and chelator compound (AH007) increases the Parkin Ligase reaction with the Activity-based Ubituitin vinyl sulfone probe. This example indicates that both chelators and electrophiles can both regulate and/or increase Parkin ligase activity.

Example 4: Parkin pUB Auto-Ubiquitinylation Assay

A Parkin pUB Auto-ubiquitinylation Assay is used to evaluate a candidate compound's potency to activate Parkin's ability to Auto-ubiquitinylate itself.

The principle of this assay is that the E3 Ligase Parkin catalyzes the transfer of Ubiquitin to target proteins, but also has the ability to auto-ubiquitinylate itself. The phospho-Ubiquition (pUb) added to the assay alters the Parkin to a state where small molecule activators can enable the Parkin to auto-ubiquitinylate though the E1-E2 cascade reaction.

The use of a Eu cryptate Ubiquition and anti 6His-d2 that binds to the His tagged Parkin will give a signal when the Eu cryptate Ubiquition is auto-ubiquitinylate onto the Parkin which can be monitored by TR-FRET.

Similar to the Activity-based probe assay in Examples 2 and 3, screening for activating compounds can be distinguished from the controls as follows:
100% activation signal=pUb activated Parkin+40 nM control activator in DMSO.
0% activation signal=pUb activated Parkin+DMSO only.
Parkin activators can be identified by an increase of the 0% activation signal TR-FRET signal.

Materials:
Assay Plate: White 384 well plate (Corning 3572)
Enzyme 1: 5 µM E1 (Ubiquitin-activating enzyme/UBE1 Boston Biochem E-305)
Enzyme 2: 25 µM E2 (UBcH7/Ube2L3 Boston Biochem E2-640)
Enzyme 3: Parkin-His tagged 203 µM (10.5 mg/ml) Supplied by An2H
pUb: 230 µM (2 mg/ml) Phospho-Ubiquitin (S65) (Boston Biochem U-102)
Supplied by An2H.
Eu Cryptate Reagent: 1.77 µM Ubiquitin Eu (CisBio 61UBIKLA) Reconstitute with 250 µl distilled water.
DMSO: DMSO (Sigma cat #D4540-100ML)
PF-127: Pluronic F-127 (Fisher Scientific 50-310-494)
Reaction Buffer: 50 mM HEPES, 50 mM NaCl, 1 mM $MgCl_2$, 0.005% Tween20, 0.1% PF-127, pH 8.5
Detection Buffer: 50 mM HEPES, 50 mM NaCl, 800 mM KF, 5 mM EDTA, 0.005% Tween20, 0.1% PF-127, pH 8.5
Detection Reagent Z: 13.4 nM Anti-6His-d2 in detection buffer
d2 Reagent: 2.67 µM Anti-6His-d2 (CisBio 61HISDLA) Reconstitute with 250 µl distilled water.
Assay Conditions:
10 µl Enzyme Reaction (15 min pre incubation Parkin, pUb and activator only)
Parkin: 196 nM
pUb: 392 nM
Activator/DMSO: 1× Activator/1% DMSO
E1: 5 nM
E2: 50 nM
Ubiquitin Eu: 8.8 nM
Reaction time: 120 minutes
Temperature: 22° C.
Total volume: 10 µl reaction
Detection Reaction
Take 10 µl of Enzyme Reaction above and add 10 µl detection Reagent Z under the following conditions:
Reaction time: 60 minutes
Temperature: 22° C.
Total volume: 20 µl
Assay Procedure:
1) Load assay plate wells with 4.9 µl 400.0 nM Parkin, 800 nM pUb in reaction buffer by use of Bravo.
2) Deliver 0.1 µl 100× activator candidates in DMSO by use of HP D-300 compound dispenser. Highest 100× concentration=100 µm and then twofold dilutions. Add each compound and control in duplicate wells.
3) Spin 1000 rpm, 2 minutes, at room temp.
4) Incubate plate for 15 minutes at room temp.
5) Add 5 µl 10 nM E1, 100 nM E2, 17.6 nM Ubiquitin Eu and 2 mM ATP in Reaction Buffer by use of Bravo.
6) Spin 1000 rpm, 2 minutes, at room temp.
7) Incubate plate for 120 minutes at room temp.
8) Add 10 µl 13.4 nM anti his d2 in detection buffer by use of Bravo.
9) Spin 1000 rpm, 2 minutes, at room temp.
10) Incubate plate for 60 minutes at room temp.
11) Read plates on Perkin Elmer Envision instrument.

Data Analysis: The Data can be read in CSV files. There are two tables in those CSV files, which are the values of 655 nm (channel 1) and 615 nm (channel 2) wavelengths respectively. The data is converted to an HTRF Ratio=(Channel 1/Channel 2)*10,000

The average of all the 0 uM controls (DMSO only)= BKGD (Background—0% activation). Subtract BKGD from each HTRF Ratio value=HTRF−BKGD. The average of all the 100 uM control activator in DMSO controls=Max (100% activation). The following equation is then used to calculate % Activation for each well/candidate as follows: % Activation=(HTRF−BKGD/Max)*100.

The % Activation of compound titration can then be used to find activation EC50 or highest % activation if less than 75% activation is seen for the candidate compound.

Figure 3:
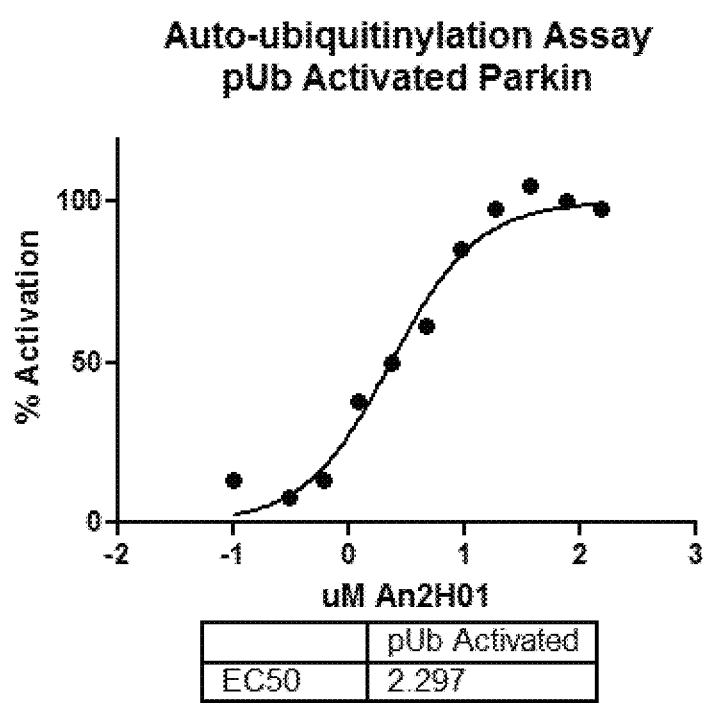
FIG. 3 indicates that compound N,N'-(1-phenyl-1H-1,2,4-triazole-3,5-diyl)dibenzamide, a chelator compound (AH001) increases Parkin activity in an auto-ubiquitination assay.
Figure 4A:
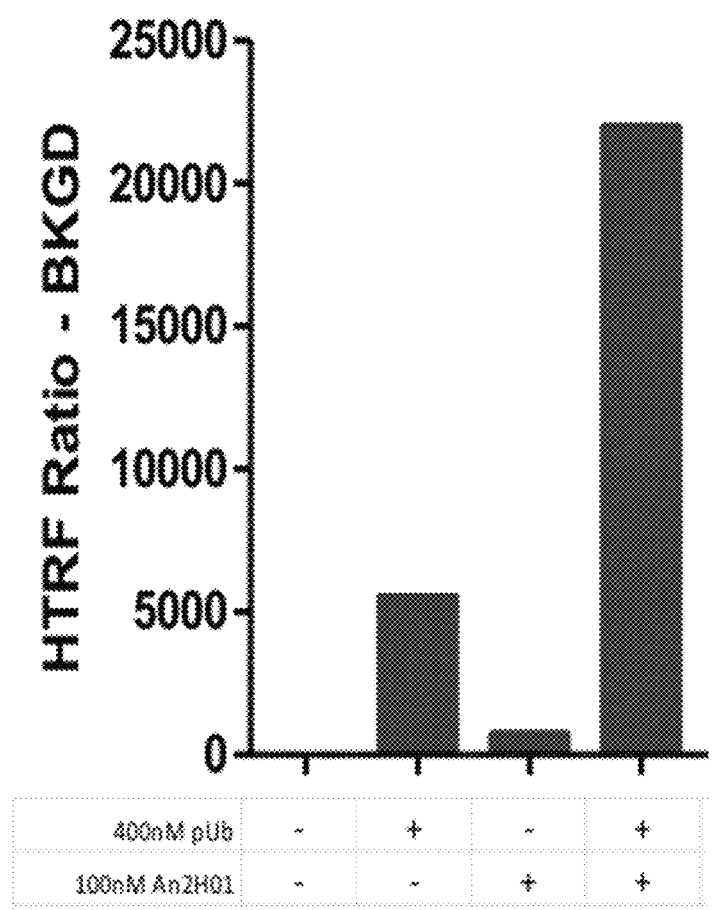
FIGS. 4A and 4B indicate that N,N'-(1-phenyl-1H-1,2,4-triazole-3,5-diyl)dibenzamide (AH001) with pUB synergistically increases parkin activation in an auto-ubiquitination assay and allows for a lower concentration of pUB to activate parkin.
Figure 4B:
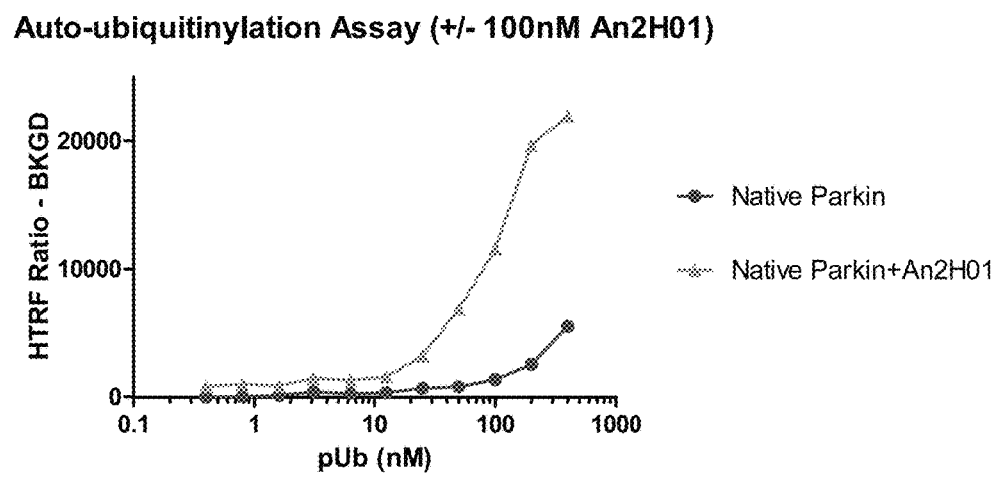

Example 5: Parkin pUB Auto-Ubiquitinylation Assay with Candidate Electrophile and Chelator Compounds The Parkin pUB auto-ubiquitinylation Assay was performed as in Example 4 above with various compounds in Table 1 and/or Table 2. At least two compounds indicated increasing Parkin activity with the activity-based probe Ubiquitin-vinyl sulfone. As demonstrated in FIG. 3, compound N,N'-(1-phenyl-1H-1,2,4-triazole-3,5-diyl)dibenzamide, a chelator compound (AH001) increases Parkin activity in an auto-ubiquitination assay. Furthermore, as indicated in FIG. 4A, N,N'-(1-phenyl-1H-1,2,4-triazole-3,5-diyl)dibenzamide (AH001) with pUB synergistically increases parkin activation in an auto-ubiquitination assay.

Figure 5:
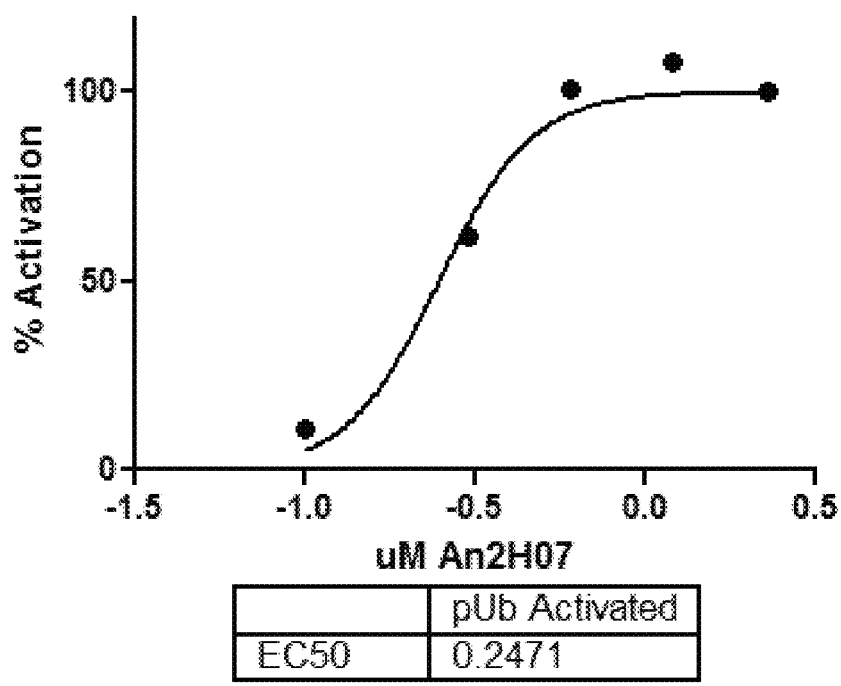
FIG. 5 indicates that 6-benzyl-2,5-dimethyl-3-phenylpyrazolo[1,5-a]pyrimidine-7-thiol, an electrophile compound (AH007) increases Parkin activity in an auto-ubiquitination assay.

Similarly, as indicated in FIG. 5, 6-benzyl-2,5-dimethyl-3-phenylpyrazolo[1,5-a]pyrimidine-7-thiol, an electrophile compound (AH007) increases Parkin activity in an auto-ubiquitination assay. This example indicates that both chelators and electrophiles can both regulate and/or increase Parkin ligase activity in an auto-ubiquitination assay.

Example 6: Residues C59 and C377 are Critical for Modulator Binding to Parkin

Parkin ligase was incubated with AH007 compound, and the mixture was then subject to tandem mass spectometry analysis after proteolytic digestion to produce fragments of Parkin ligase. The goal was to identify specific fragments of Parkin that contain compound bound AH007, revealing the specific binding residues of Parkin for the compound. Compound An2H07 is also fragmented when analyzed by mass spectrometry. Therefore, characteristic pieces of the compound AH007 that are attached to specific residues of Parkin can also be identified.

These fragments were characterized for alterations in fragment size indicative of bound small molecule of the predicted molecular weight of AH007. The mass spectrometry data identified three specific fragments of AH007 at two specific residues of Parkin ligase. The data identified a fragment of 253.08-256.09 of AH007 compound attached to cysteine residue 377 of Parkin ligase (C377) and a fragment of 343.14-346.14 of AH007 compound attached to C377. The data also identified a fragment of 253.08-256.09 of AH007 compound attached to cysteine residue 59 of Parkin ligase (C59). The mass spectrometry data of Parkin ligase incubated with AH007 compound thus indicates that the compound binds and/or attaches to two specific sites in Parkin ligase: C59 and C377. Residues C59 and C377 were the only two consistent sites observed, even when the concentration of AH007 compound was dramatically increased in the mixture with Parkin ligase, suggesting specificity for these sites over numerous other sites of potential attachment. It is also believed that at least C377 is included in ZnF domains of human Parkin Ligase, and thus accords with the theory that cysteine residues in the flexible Parkin ligase ZnF domains are vulnerable for attachment and/or interruption by small molecule candidates. Peptide fragments of Parkin comprising C59 and/or C377 will be useful to design further binding assays and selection of additional modulating agents.

The publications discussed herein are provided solely for their disclosure prior to the filing date of the present application. Nothing herein is to be construed as an admission that the present invention is not entitled to antedate such publication by virtue of prior invention.

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

```
                        SEQUENCE LISTING

<160> NUMBER OF SEQ ID NOS: 1

<210> SEQ ID NO 1
<211> LENGTH: 465
<212> TYPE: PRT
<213> ORGANISM: Homo sapiens

<400> SEQUENCE: 1

Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45

Glu Leu Arg Asn Asp Trp Thr Val Gln Asn Cys Asp Leu Asp Gln Gln
    50                  55                  60

Ser Ile Val His Ile Val Gln Arg Pro Trp Arg Lys Gly Gln Glu Met
65                  70                  75                  80

Asn Ala Thr Gly Gly Asp Asp Pro Arg Asn Ala Ala Gly Gly Cys Glu
                85                  90                  95

Arg Glu Pro Gln Ser Leu Thr Arg Val Asp Leu Ser Ser Ser Val Leu
            100                 105                 110

Pro Gly Asp Ser Val Gly Leu Ala Val Ile Leu His Thr Asp Ser Arg
        115                 120                 125

Lys Asp Ser Pro Pro Ala Gly Ser Pro Ala Gly Arg Ser Ile Tyr Asn
    130                 135                 140

Ser Phe Tyr Val Tyr Cys Lys Gly Pro Cys Gln Arg Val Gln Pro Gly
145                 150                 155                 160

Lys Leu Arg Val Gln Cys Ser Thr Cys Arg Gln Ala Thr Leu Thr Leu
                165                 170                 175

Thr Gln Gly Pro Ser Cys Trp Asp Asp Val Leu Ile Pro Asn Arg Met
            180                 185                 190

Ser Gly Glu Cys Gln Ser Pro His Cys Pro Gly Thr Ser Ala Glu Phe
        195                 200                 205

Phe Phe Lys Cys Gly Ala His Pro Thr Ser Asp Lys Glu Thr Ser Val
    210                 215                 220

Ala Leu His Leu Ile Ala Thr Asn Ser Arg Asn Ile Thr Cys Ile Thr
225                 230                 235                 240

Cys Thr Asp Val Arg Ser Pro Val Leu Val Phe Gln Cys Asn Ser Arg
                245                 250                 255

His Val Ile Cys Leu Asp Cys Phe His Leu Tyr Cys Val Thr Arg Leu
```

|  | 260 |  |  |  | 265 |  |  |  | 270 |  |  |  |
|---|---|---|---|---|---|---|---|---|---|---|---|---|
| Asn | Asp | Arg<br>275 | Gln | Phe | Val | His | Asp<br>280 | Pro | Gln | Leu | Gly | Tyr<br>285 | Ser | Leu | Pro |
| Cys | Val<br>290 | Ala | Gly | Cys | Pro | Asn<br>295 | Ser | Leu | Ile | Lys | Glu<br>300 | Leu | His | His | Phe |
| Arg<br>305 | Ile | Leu | Gly | Glu | Glu<br>310 | Gln | Tyr | Asn | Arg | Tyr<br>315 | Gln | Gln | Tyr | Gly | Ala<br>320 |
| Glu | Glu | Cys | Val | Leu<br>325 | Gln | Met | Gly | Gly | Val<br>330 | Leu | Cys | Pro | Arg | Pro<br>335 | Gly |
| Cys | Gly | Ala | Gly<br>340 | Leu | Leu | Pro | Glu | Pro<br>345 | Asp | Gln | Arg | Lys | Val<br>350 | Thr | Cys |
| Glu | Gly | Gly<br>355 | Asn | Gly | Leu | Gly | Cys<br>360 | Gly | Phe | Ala | Phe | Cys<br>365 | Arg | Glu | Cys |
| Lys | Glu<br>370 | Ala | Tyr | His | Glu | Gly<br>375 | Gly | Cys | Ser | Ala | Val<br>380 | Phe | Glu | Ala | Ser |
| Gly<br>385 | Thr | Thr | Thr | Gln | Ala<br>390 | Tyr | Arg | Val | Asp | Glu<br>395 | Arg | Ala | Ala | Glu | Gln<br>400 |
| Ala | Arg | Trp | Glu | Ala<br>405 | Ala | Ser | Lys | Glu | Thr<br>410 | Ile | Lys | Lys | Thr | Thr<br>415 | Lys |
| Pro | Cys | Pro | Arg<br>420 | Cys | His | Val | Pro | Val<br>425 | Glu | Lys | Asn | Gly | Gly<br>430 | Cys | Met |
| His | Met | Lys<br>435 | Cys | Pro | Gln | Pro | Gln<br>440 | Cys | Arg | Leu | Glu | Trp<br>445 | Cys | Trp | Asn |
| Cys | Gly<br>450 | Cys | Glu | Trp | Asn | Arg<br>455 | Val | Cys | Met | Gly | Asp<br>460 | His | Trp | Phe | Asp |
| Val<br>465 |

What is claimed is:

1. A method of activating a Parkin ligase to treat a patient in need thereof, comprising administering to the patient a therapeutically effective amount of a compound of formula:

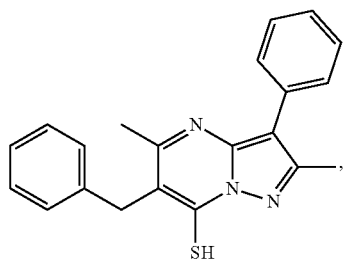

or a pharmaceutically acceptable salt thereof.

2. The method of claim 1, wherein the compound disrupts at least one Parkin ligase zinc finger, wherein the compound can coordinate with a zinc ion, and/or bind or react with a cysteine.

3. The method of claim 2, wherein the amino acid residues of at least one zinc finger corresponds to or aligns within one or more domains selected from the group consisting R0 amino acids 141-216, IBR amino acids 328-377, and R2 amino acids 415-465 of human Parkin Ligase.

4. The method of claim 3, wherein at least one zinc finger comprises four cysteine residues.

5. The method of claim 1, wherein Parkin ligase activation alters ubiquitination.

6. The method of claim 1, wherein the compound substantially disrupts the structure of at least one zinc finger in the Parkin ligase.

7. The method of claim 6, wherein the amino acid residues of at least one zinc finger corresponds to or aligns within one or more domains selected from the group consisting R0 amino acids 141-216, IBR amino acids 328-377, and R2 amino acids 415-465 of human Parkin Ligase.

8. The method of claim 2, wherein the compound binds or reacts with the thiol group in a cysteine.

9. The method of claim 2, wherein the cysteine is selected from one or more of the group consisting of C59 and C377 of human Parkin ligase.

10. The method of claim 2, wherein the cysteine is C377 of human Parkin ligase.

11. The method of claim 6, wherein the amino acid residues of at least one zinc finger corresponds to or aligns within one or more amino acids selected from the group consisting of C59 and C377 of human Parkin Ligase.

12. The method of claim 6, wherein the amino acid residues of at least one zinc finger corresponds to or aligns with C377 of human Parkin Ligase.

13. The method of claim 7, wherein the compound substantially disrupts the structure of at least one zinc finger located in the IBR domain (amino acids 328-377).

14. The method of claim 1, wherein the compound is an electrophile and/or chelator.

* * * * *